(12) United States Patent
Brigham

(10) Patent No.: US 11,147,250 B2
(45) Date of Patent: *Oct. 19, 2021

(54) METHODS, COMPOSITIONS AND SYSTEMS FOR PRODUCTION OF RECOMBINANT SPIDER SILK POLYPEPTIDES

(71) Applicant: EGI-LENDERS, LLC, Potomac, MD (US)

(72) Inventor: David L. Brigham, Charlotte, NC (US)

(73) Assignee: EGI-LENDERS, LLC, Potomac, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/104,469

(22) Filed: Aug. 17, 2018

(65) Prior Publication Data

US 2019/0116768 A1  Apr. 25, 2019

Related U.S. Application Data

(60) Continuation of application No. 14/843,363, filed on Sep. 2, 2015, now Pat. No. 10,051,846, which is a division of application No. 12/363,326, filed on Jan. 30, 2009, now Pat. No. 9,131,671.

(60) Provisional application No. 61/025,616, filed on Feb. 1, 2008, provisional application No. 61/037,937, filed on Mar. 19, 2008.

(51) Int. Cl.
| | |
|---|---|
| A01K 67/033 | (2006.01) |
| C07K 14/435 | (2006.01) |
| C12N 15/90 | (2006.01) |
| C12N 15/85 | (2006.01) |
| C07K 14/78 | (2006.01) |

(52) U.S. Cl.
CPC ...... *A01K 67/0339* (2013.01); *A01K 67/0335* (2013.01); *C07K 14/43518* (2013.01); *C07K 14/43586* (2013.01); *C07K 14/78* (2013.01); *C12N 15/8509* (2013.01); *C12N 15/902* (2013.01); *A01K 2217/05* (2013.01); *A01K 2217/15* (2013.01); *A01K 2227/703* (2013.01); *A01K 2227/706* (2013.01); *A01K 2267/01* (2013.01); *C07K 2319/00* (2013.01); *C12N 2015/8518* (2013.01)

(58) Field of Classification Search
CPC .................................................... A01K 67/04
See application file for complete search history.

(56) References Cited

U.S. PATENT DOCUMENTS

| | | | |
|---|---|---|---|
| 5,243,038 A | 9/1993 | Ferrari et al. | |
| 5,728,810 A | 3/1998 | Lewis et al. | |
| 5,733,771 A | 3/1998 | Lewis et al. | |
| 5,756,677 A | 5/1998 | Lewis et al. | |
| 5,830,713 A | 11/1998 | Ferrari et al. | |
| 5,989,894 A | 11/1999 | Lewis et al. | |
| 6,018,030 A | 1/2000 | Ferrari et al. | |
| 6,268,169 B1 | 7/2001 | Fahnestock | |
| 6,355,776 B1 | 3/2002 | Ferrari et al. | |
| 6,608,242 B1 | 8/2003 | Yang | |
| 6,765,086 B2 | 7/2004 | Rothstein et al. | |
| 6,872,869 B2 | 3/2005 | Liu et al. | |
| 6,965,060 B2 | 11/2005 | Yang | |
| 7,033,603 B2 | 4/2006 | Nelson et al. | |
| 7,041,797 B2 | 5/2006 | Vollrath | |
| 7,048,963 B2 | 5/2006 | Braithwaite et al. | |
| 7,049,405 B2 | 5/2006 | Gosline et al. | |
| 7,057,023 B2 | 6/2006 | Islam et al. | |
| 7,060,260 B2 | 6/2006 | Fahnestock et al. | |
| 7,100,490 B2 | 9/2006 | Muller, Jr. | |
| 9,131,671 B2 * | 9/2015 | Brigham ............ | C12N 15/8509 |
| 9,826,723 B2 | 11/2017 | Brigham | |
| 10,051,846 B2 | 8/2018 | Brigham | |
| 2001/0042255 A1 | 11/2001 | Karatzas et al. | |
| 2003/0166846 A1 | 9/2003 | Rothstein et al. | |
| 2003/0213005 A1 | 11/2003 | Alphey et al. | |

(Continued)

FOREIGN PATENT DOCUMENTS

| | | |
|---|---|---|
| CN | 1910196 A | 2/2007 |
| EP | 1712561 A1 | 10/2006 |

(Continued)

OTHER PUBLICATIONS

Tomita et al. (2007, Transgenic Res., vol. 16, pp. 449-465). (Year: 2007).*
"European Office Action Issued in European Application No. 09706973.6 dated Nov. 25, 2011", 5 pages.
"European Summons to Attend Oral Proceedings Issued in European Application No. 09706973.6 dated Sep. 20, 2017", 7 pages.
"European Office Action Issued in European Application No. 09706973.6 dated Dec. 1, 2015", 4 pages.

(Continued)

*Primary Examiner* — Thaian N. Ton
*Assistant Examiner* — David A Montanari
(74) *Attorney, Agent, or Firm* — Johnson, Marcou, Isaacs & Nix, LLC; F. Brent Nix, Esq.; Rachel D. Rutledge, Esq.

(57) ABSTRACT

Disclosed are methods, compositions, and systems for transforming silkworms to produce spider silk and analogs of spider silk. In certain embodiments, the method may include inserting a DNA sequence coding for at least a portion of a spider silk fibroin polypeptide, or an analog of a spider silk fibroin polypeptide, positioned between at least a portion of the 5' and 3' ends of a silkworm fibroin gene to generate a fusion gene construct having a sequence that encodes for a polypeptide comprising both spider silk fibroin and silkworm silk fibroin sequences. In certain embodiments, the fused gene is able to replace a native gene present in the silkworm such that the transformed silkworm expresses a polypeptide comprising a spider silk fibroin polypeptide, or an analog thereof, and expresses significantly less of the native silkworm silk.

12 Claims, 31 Drawing Sheets

Specification includes a Sequence Listing.

(56) References Cited

U.S. PATENT DOCUMENTS

| | | |
|---|---|---|
| 2004/0117874 A1 | 6/2004 | Yang |
| 2005/0010035 A1 | 1/2005 | Lewis et al. |
| 2005/0034280 A1 | 2/2005 | Gosline et al. |
| 2005/0090641 A1 | 4/2005 | Valluzzi et al. |
| 2008/0287651 A1 | 11/2008 | Hiramatsu et al. |
| 2009/0205059 A1 | 8/2009 | Brigham |
| 2015/0373956 A1 | 12/2015 | Brigham |
| 2015/0376263 A1 | 12/2015 | Brigham |
| 2016/0345555 A1 | 12/2016 | Brigham |

FOREIGN PATENT DOCUMENTS

| | | |
|---|---|---|
| WO | 92/22653 A1 | 12/1992 |
| WO | 02/40528 A1 | 5/2002 |

OTHER PUBLICATIONS

"European Office Action Issued in European Application No. 09706973.6 dated Jun. 13, 2014", 7 pages.

"European Office Action Issued in European Application No. 09706973.6 dated Mar. 10, 2015", 5 pages.

"European Application No. 09706973.6, "Response to Office Action", dated Dec. 23, 2014", 6 pages.

"European Application No. 09706973.6, "Response to Office Action", dated Mar. 10, 2014", 9 pages.

"European Office Action Issued in European Application No. 09706973.6 dated Aug. 29, 2013", 7 pages.

"European Application No. 09706973.6, "Response to Office Action", dated Jun. 1, 2012", 14 pages.

"Indian Office Action Issued in Indian Patent Application No. 2924/KOLNP/2010 dated Nov. 29, 2016", 10 pages.

"International Search Report & Written Opinion of the International Searching Authority Issued in International Application No. PCT/US2009/032660 dated May 8, 2009", 10 pages.

"U.S. Final Office Action Issued in U.S. Appl. No. 12/363,326 dated Apr. 22, 2014", 6 pages.

"U.S. Office Action Issued in U.S. Appl. No. 12/363,326 dated Aug. 9, 2013", 22 pages.

"U.S. Office Action Issued in U.S. Appl. No. 12/363,326 dated Aug. 20, 2014", 18 pages.

"U.S. Notice of Allowance Issued in U.S. Appl. No. 12/363,326 dated Jul. 30, 2015", 8 pages.

"U.S. Notice of Allowance Issued in U.S. Appl. No. 12/363,326 dated Jun. 25, 2015", 9 pages.

"U.S. Office Action Issued in U.S. Appl. No. 12/363,326 dated Dec. 19, 2012", 18 pages.

"U.S. Restriction Requirement Issued in U.S. Appl. No. 14/833,740 dated Nov. 30, 2016", 6 pages.

"U.S. Office Action Issued in U.S. Appl. No. 14/843,363 dated Jul. 19, 2017", 9 pages.

"U.S. U.S. Restriction Requirement Issued in U.S. Appl. No. 14/843,363 dated Jan. 13, 2016", 8 pages.

"U.S. Final Office Action Issued in U.S. Appl. No. 14/843,535 dated Sep. 21, 2016", 16 pages.

"U.S. Office Action Issued in U.S. Appl. No. 14/843,535 dated Dec. 16, 2015", 11 pages.

"U.S. Notice of Allowance Action Issued in U.S. Appl. No. 14/843,535 dated Sep. 21, 2017", 7 pages.

Denny, Mark, "The Physical Properties of Spider's Silk and their Role in the Design of Orb-Webs", The Journal of Experimental Biology, vol. 65, 1976, 483-506.

Fahnestock, et al., "Microbial Production of Spider Silk Proteins", Reviews in Molecular Biotechnology, vol. 74, 2000, 105-119.

Gosline, et al., "The Mechanical Design of Spider Silks: From Fibroin Sequence to Mechanical Function", Journal of Experimental Biology, vol. 202, 1999, 3295-3303.

Guinea, et al., "Minor Ampullate Silks from Nephila and Argiope Spiders: Tensile Properties and Microstructural Characterization", Biomacromolecules, vol. 13, No. 7, 2012, 2087-2098.

Hyodo, et al., "Linkage Analysis of the Fibroin Gene in the Silkworm", The Japanese Journal of Genetics, vol. 55, 1980, 297-300.

Kojima, et al., "Secondary Structure Analysis of Genetically Modified Silk with Spider Fiber Protein", CA Registry, vol. 148, No. 193429, 2007, 1 page.

Lewis, R., "Spider Silk: Ancient Ideas for New Biomaterials", Chemical Reviews, vol. 106, 2006, 3762-3774.

Miao et al., "Report on Construction of Gene-Targeting Vector for Homologous Recombination and Transformation in Silkworm *Bombyx mori* L.", Journal of Experimental Medicine, vol. 129, 2005, 129-133.

Parry, R., "Coming Soon—Spider Socks (in Packs of 8)", Timesonline, as Printed from: http://www.timesonline.co.uk/tol/news/world/asia/article3026488.ece?print=yes&randnu, Dec. 10, 2007, 1 page.

Pearson, et al., "Improved Tools for Biological Sequence Comparison", Proceedings of the National Academy of Sciences of the United States of America, vol. 85, Apr. 1988, 2444-2448.

Prudhomme, et al., "Perspectives in Silkworm (*Bombyx mori*) Transgenesis", Current Science, vol. 83, No. 4, Aug. 25, 2002, 432-438.

Rubnitz, et al., "The Minimum Amount of Homology Required for Homologous Recombination in Mammalian Cells", Molecular and Cellular Biology, vol. 4, 1984, 2253-2258.

Takei, et al., "Genetic Analysis of the Nd-S Mutation in the Silkworm, *Bombyx mori*", The Japanese Journal of Genetics, vol. 59, 1984, 307-313.

Takei, et al., "Reduced Level of Secretion and Absence of Subunit Combination for the Fibroin Synthesized by a Mutant Silkworm", Journal of Cell Biology, vol. 99, 1984, 2005-2010.

Takyia, et al., "Transcriptional Regulatory Elements in the Upstream and Intron of the Fibroin Gene Bind Three Specific Factors POU-M1, Bm Fkh and FMBP-1", Biochemical Journal, vol. 321, 1997, 645-653.

Wen et al. "Transgenic Silkworms (*Bombyx morr*) Produce Recombinant Spider Dragline Silk in Cocoons", Molecular Biology Reports, vol. 37, 2010, 1815-1821.

Wilbur, et al., "Rapid Similarity Searches of Nucleic Acid and Protein Data Banks", Proceedings of the National Academy of Sciences of the United States of America, vol. 80, 1983, 726-730.

Winkler, et al., "Molecular Biology of Spider Silk", Reviews in Molecular Biotechnology, vol. 74, 2000, 85-93.

Work, et al., "Viscoelastic Behaviour and Wet Supercontraction of Major Ampullate Silk Fibres of Certain Orb-Web-Building Spiders (*Araneae*)", The Journal of Experimental Biology, vol. 118, 1985, 379-404.

\* cited by examiner

BspEI                                                                                                    (SEQ ID NO: 1)
tccggaTTGGGGGTCAGGGTGCTCAGCCGCTGCTGCTCAGCCGCTGCGGGAGGTGGGGGTCAA                                          (SEQ ID NO: 2)
 S   G   L   G   G   Q   Q   L   L   L   S   Q   P   L   R   E   V   G   V   Q
GGGGAGGATATGGAGGATTAGGTCGCAGGTCGCAGCTGCTGCTGCTGCTCAGCCGCTGCTGCTCAGCCGCTGCGGGAGGTGGGGGTCAA
 G   G   Y   G   G   L   G   S   Q   A   G   R   G   G   S   R   G   G   L
GGAGGACAAGGAGCTGCTGCGGCTGCTGCTGCTGCAAAAGGGGAGGAGGACAAGGCGGAGATATGGG
 G   G   Q   A   A   A   A   A   A   G   G   Q   Q   G   G   Y   G
GGTCAAGGTGCTGCGCTGCTGCTGCTGCTGCGGAGGAGGATTGGGGGACAAGGAGCT
 G   Q   G   A   A   A   A   A   A   G   G   Q   G   G   Y   G
GGTTTAGGAAGTCAGGCAGGAGTCAGGGAGGGGCGGGCTTGGGGGCAGCTTAGGAAGC
 G   L   G   S   Q   A   G   R   G   G   L   G   Q   G   A
GCTGCTGCTGCAGCCGCTGCTGCTGCTGCTGCGGAGGAGGATATGGGGATTAGGAAGC
 A   A   A   A   A   A   A   G   G   Q   G   G   Y   G   G   L   G   S
CAAGCTGGAAGGGAGGAGATTAGGAGGTGCTGCTGCAGCTGCTGCTGCTGCAAAGCTGAAGAGCTGGAGGATACGGTGGG
 Q   A   G   R   G   G   L   G   S   Q   A   G   R   G   G   L   G
CAGGGAGGTCAGGGAGGTGCTGCTGCAGCTGCTGCTGCTGCAAAGCTGAAGAGCTGAAGCTGAAGCTGGAGGATACGGTGGG
 Q   G   A   A   A   A   A   A   G   G   Q   G   G   Y   G   G
TTGGGGAGTCAAGCAGGAGGATTATGGAGGTTATGGAGGAGGAGGATTAGGAGG
 L   G   S   Q   A   G   R   G   G   Y   G   G   L   G   S   Q   R   G   G
GGTAGTGGTCAGGGAGGAGGATTAGGAGGAGGTGCTGCTGCTGCAAAAAGTCAAGCTGCTGCAGGTGGA
 G   G   Q   G   G   L   G   Q   G   G   Q   G   G   A   A   A   A   A   G   G
GCAGCCGCTGCTGCTGCTGCTGCTGCAAAAAAGGTTATGGAGGTTATGGAGGTCAAGCAGGAAGA
 G   A   A   A   A   A   A   A   G   G   L   G   S   Q   A   G   R
GGGGGATTAGGTGGTCAAGGAGTCAGAGAGGAGGTTAGGTcccggg
 G   G   L   G   G   Q   A   A   A   A   A   A   G   G   G   Q
GGTGGAAGTCAGGCAGGTAGAGAGGAGGTTAGGTcccggg
 G   G   S   Q   A   G   R   G   G   L   G   P   G
                                             XmaI         Alpha helix     Beta Sheet FIGURE 4A Internal Repeat Segment 948 bp

```
TCCGGATTGGGGGTCAGGGTGCTGGTGCTGCAGCCGCTGCTGCGGGAGGTGCGGGTCAA   (SEQ ID NO: 3)
 S  G  L  G  G  Q  G  A  G  A  A  A  A  A  G  G  A  G  G  Q
                      ↕                       ↕
TCCGGATTGGGGGTCAGGGTGCTGCTGCTGCAGCCGCTGCTGCGGGAGGTGGGGGTCAA   (SEQ ID NO: 4)
 S  G  L  G  G  Q  G  A  A  A  A  A  A  A  G  G  G  G  G  Q
```

Removal of Potential Supercontracting Motifs

FIGURE 4B

Start Codon                              Intron Start
ATGAGAGTCAAAACCTTTGTGATCTTGGTCTGCGCTCTGCAGGTGAGTTAATTATTTTACTATTATTTCAGAAGGTGGCCAGACGATATCACGGG
 M  R  V  K  T  F  V  I  L  V  C  A  L  Q (SEQ ID NO: 6)
CCACCTGATAATAAGTGGTCGCCAAAACGCACAGATATCGTAAATTGTGCCATTTGATTTGTCACGCCCTGGGGGCTACGGAATAAACTACATT
TATTTATTTAAAAAATGAACCTTAGATTATGTAACTTGTGATTTATTTGCGTCAAAAGTAGGCAAGATGAATCTATGTAAATACTGGGCAGACTT
GCAATATCCTATTTCACCGGTAAAATCAGCATTGCAATGCTAAAATTCAACAATATGTAAAACAATTCGTAAAGCATCATTAGAAAATA
GACGAAAGAAATTGCATAAAATTATAACCGCATTATTAATTTATTATGATATCTATTAACAATTGCTATTGCCTTTTTTTCGCAAATTATAATCA
TTTTCATAACCTCGAGGTAGCATTCTGTACATTTAATACATTGGTATGTGATTATAACACGAGCTGCCCACTGAGTTTCTCGCCAGATCTTCTC
AGTGGGTCGCGTTACCGATCACGTGATAGATTCTATGAAGCACTGCTCTTGTTAGGGCTAGTGTTAGTAAATTCTTTCAGGTTGAGTCTGAGAGC
TCACCTACCCATCGGAGCGTAGCTGGAATAGGCTACCAGCTGGTAGGAAACAAAGCTCGAAACAAGCTCAAGTAATAACAACATAATGTG
ACCATAAAATCTCGTGGTGTATGAGATACAATTATGTACTTCCCACAAATGTTACATAATTAGAATGTGTTCAACTTGCCTAACGCCCCAGC
TAGAACATTCAATTATTACTATTACCACTACTAAGGCAGTATGTCCTAACTCGTTCCAGATCAGCGCTAACTTCGATTGAATGTGCGAAATTTAT
                                                                            Intron End
AGCTCAATATTTAGCACTTATCGTATTGATTTAAGAAAAAATTGTTAACATTTGTTTCAGTATGTCGCTTATACAAATGCAAACATCAATGAT
                                                          Y  V  A  Y  T  N  A  N  I  N  D
BspEI
Tccgga      (SEQ ID NO: 5)
F D         (SEQ ID NO: 7)

5' Homologous Sequence 1051 bp

FIGURE 5

Xma.I cccgggGTGTCATCTCGCTTCATCTCGCAGTTACGACTATTCTCGTCGTAACGTCCGCAAAAACTGTGGAATTCCTAGAAGACAACTAGTTGTTAAA
 P  G  V  S  S  A  S  S  R  S  Y  D  Y  S  R  R  N  V  R  K  N  C  G  I  P  R  R  Q  L  V  V  K
TTCAGAGCACTGCCCTGTGTGAATTGCTAATTTTAATATAAAATAACCCCTGTTTCTTACTTCGTCCTGATACATCTATGTTTTTTTTCGTTA
 F  R  A  L  P  C  V  N  C  (SEQ ID NO: 9)
ATAAATGAGAGCATTTAAGTTATTGTTTTTAATTACTTTTTTTAGAAAACAGATTTCGGATTTTTTGTATGCATTTATTTGAATGTACTAATATA ATCAATTAATCAATGAATTCATTTATTTAAGGGATAACAATAATCCATGAATTCACATGCACATTTAAAACAAAACTAAATTACAATAGTTCATAT AAAAACAACAAGTATGCCTTCTCAACTAAGAATACTATATTGTTAAACCGTAAAAAAAGTCATATTTCTGTATATCAAACACATCTAATATTAAA AAAAACAGTCAGCAAGCACTTACAAGTGTGGGCTCGGACAGCAATTACCTGGTCTCAGGAGACACTTGAAGAACGAGAAGCACGTCTCTCTGTCGATT GCGAGGCTCATGCACTATCGCTTGAGTCTGAGACCTTTACTGATAGGGAAATCCGTTGAGCTCTCAGAGGGTTCGGACAGCAAAAGCTTGCCCGGT CTCAGGAGACATTAGAAGAACGGGAAGCATAACTCAATACCGATCGCGTTTCCATTGAGCCTATGCTTCGTGATAATAATAAATAAAGCCCAAGGTC

AGACGCTAAAA (SEQ ID NO: 8)

3' Homologous Sequence 786 bp

FIGURE 6 start codon　　　　　　　　　　　　　　　　　　　　　　　Intron Start

```
  1  atgagagtaa tagccttcgt gatcttgtgc tgcgctttgc aggtgagttc caacatttat
     M  R  V    I  A  F  V    I  L  C    C  A  L    Q  (SEQ ID NO: 11)
 61  ttaaatattt tcataatatg caaatgttcc acacgcttat aattttaaat aattattttt
121  taatggtgaa aataaagcaa tataaatttc aattacttac agtatgcaac tgctaaaaat
                                                  Intron End  Y  A  T    A  K  N
181  ttacgtcacc acgacgaata cgtagacaat catgggcaat tagtcgaacg attcacaacc
     L  R  H    H  D  E  Y    V  D  N    H  G  Q    L  V  E  R    F  T  T
241  cgtaaacatt ttgaaaggaa cgctgcaacg cgcccacatc tttctggtaa tgaacgatta
     R  K  H    F  E  R  N    A  A  T    R  P  H    L  S  G  N    E  R  L
301  gtcgagacta ttgtcctcga agaggatccg tatggtcatg aagatatcta cgaagaagat
     V  E  T    I  V  L  E    E  D  P    Y  G  H    E  D  I  Y    E  E  D
361  gttgttatca agagagtacc aggggctagt tctagcgctg ctgcagcgtc tagtgccagc
     V  V  I    K  R  V  P    G  A  S    S  S  A    A  A  A  S    S  A  S
421  gccgggtcag gacaaactat tatagttgaa agacaggctt cacatggtgc aggcggtgcc
     A  G  S    G  Q  T  I    I  V  E    R  Q  A    S  H  G  A    G  G  A
481  gcaggagctg cagcggggagc cgcagctggc tcaagtgcca gacgaggcgg tggatttac
     A  A  A    A  A  G  A    A  A  G    S  S  A    R  R  G  G    G  F  Y
541  gaaacacata atagttacag cagttacgga tcaggctcat catcagcagc agccggctca
     E  T  H    N  S  Y  S    S  Y  G    S  G  S    S  S  A  A    A  G  S
601  ggtgctggag gagtaggcgg tggttatgga tccgga (SEQ ID NO: 10)
     G  A  G    G  V  G  G    G  Y  G    S  G  (SEQ ID NO: 12)
                                         BspEI
```

*Antheraea pernyi* 5' homologous segment

FIGURE 7

```
      XmaI
  1   CCCGGgggtt  tcggacgagg  tgacggtggt  tatggttcag  gctcatcggc  agcagcagca
        P  G     F  G  R  G   D  G  G     Y  G  S    G  S  S  A   A  A  A 61   gcggcgggcgg cggcggcggc  tgcaagacga  gcaggtcacg  gacgttctgc  aggaagtgca
        A  A  A   A  A  A     A  R  R     A  G  H    G  R  S  A   G  S  A 121   gcagcagcag  cagcagctgc  agctgccagcg gctgcctcag  gtgctggtgg  atcaggcggt
        A  A  A   A  A  A     A  A  A  A  A  A  S    G  A  G  G   S  G  G 181   agttatggat  gggactatga  aagttacggt  tctggctcag  cggcagcagc  agctggctca
        S  Y  G   W  D  Y  E  S  Y  G     S  G  S    A  A  A  A   A  G  S 241   ggtgctggag  gatcaggcgg  tggttatgga  tggggtgacg  gcggttatgg  ttcaggttct
        G  A  G   G  S  G  G  G  Y  G    W  G  D     G  G  Y  G   S  G  S 301   tctgcggcag  cagcagcagc  agcggcggcg  gcggcaggat  caagacgctc  agggcatgat
        S  A  A   A  A  A  A  A  A  A     A  A  G     S  R  R  S   G  H  D 361   cgtgcatatg  gagcaggaag  tgctgcagcc  gcagcagcag  cagctgccgc  tggcgcaggg
        R  A  Y   G  A  G  S  A  A  A    A  A  A  A   A  A  A     G  A  G 421   gctagtcgac  aagtcggaat  ttatggaaca  gacgatggct  tcgtattaga  tggaggttac
        A  S  R   Q  V  G  I  Y  G  T    D  D  G     F  V  L  D   G  G  Y 481   gattcagagg  gatcagcggc  ggcggcggca  gcggcagcag  cagctgccgg  gtcatcaagt
        D  S  E   G  S  A  A  A  A  A    A  A  A     A  A  A  A   S  S  S 541   ggtagatcta  ctgaaggtca  tccacttctt  tcgatatgct  gcaggccgtg  ttctcacagt
        G  R  S   T  E  G  H  P  L  L    S  I  C     R  P  C     S  H  S 601   catagctatg  aagcttccag  aatttccgtc  cactaa            (SEQ ID NO: 13)
        H  S  Y   E  A  S  R  I  S  V    H STOP            (SEQ ID NO: 14)

Antheraea pernyi 3' homologous segment

FIGURE 8
``` start codon                                                                                              Intron Start

1  atgagagta acagccttcg tgatcttgtg ctgcgctttg caggtgagtt ccaacatta
     M  R  V   T  A  F    V  I  L  C   C  A  L                         Q (SEQ. ID NO: 16)

61  tttaaataat ttcatggaat aatataataa taaataaaaa aataaataat aataatattg 121  catacactta taattttaaa taattatttt ttaactggga aaataaagca atataaattt
     Intron End

181  caattactta cagtatgcaa ctgctaataa tttacatcaa cacgacgaat atgtagataa
                   Y  A   T  A  N  N   L  H  H   H  D  E   Y  V  D  N 241  tcatgggcaa ttagtcgaaa gattcacaac ccgtaaacat tatgaaagga acgccgcaac
     H  G  Q    L  V  E   R  F  T  T   R  K  H   Y  E  R   N  A  A  T 301  gcgtccacat ctttctggta atgaacgatt agtcgagact attgtcctcg aagaggatcc
     R  P  H    L  S  G   N  E  R  L   V  E  T   I  V  L   E  E  D  P 361  gtatggtcat gaagatatct acgaagaaga tgttgttatc aatagagtac caggggccag
     Y  G  H    E  D  I   Y  E  E  D   V  V  I   N  R  V   P  G  A  S 421  ttctagcgct gctgcagcgt ctagtgccag cgccgggtca ggacaaacta ttatagttga
     S  S  A    A  A  A   S  S  A  S   A  G  S   G  Q  T   I  I  V  E 481  aagacaggct tcacatggag caggaggtgc tgcaggcgct gcagcgggag ctgcagctgg
     R  Q  A    S  H  G   A  G  G  A   A  G  A   A  A  G   A  A  A  G 541  ctcaagtgcc agaggaggaa gtggatttta cgaaacacac gatagttata gcagttacgg
     S  S  A    R  G  G   S  G  F  Y   E  T  H   D  S  Y   S  S  Y  G 601  atcaggctcg tccgga      (SEQ ID NO: 15)
     S  G  S   S  G        (SEQ ID NO: 17)
              BspEI

*Antheraea yamamai* 5' homologous segment

FIGURE 9

```
      XmaI
  1  CCCGGGcag cagccggctc cggtgctgga ggacgaggcg acggcggtta tggttcaggc
        P  G  A   Q  P  A  S   R  V  L  E   D  E  G  R   T  A  V   W  F  Q  A
 61  tcttcggcag cagcagcagc ggcagcggca gcagcggctg caagacgagc gggccatgac
        S  S  A   A  A  A  A   A  A  A  A   A  A  A  A   Q  D  E   G  P  *  (H D?)
121  catgctgctg gaagttcagg cggtggttat agctgggatt atagtagtta tggttcagaa
        R  A  A   G  S  S  G   G  G  Y  S   W  D  Y   S  S  Y   G  S  E
181  tcagcggcag cagcagcagc agcagcagca gcaggctcag gtgctggagg agtaggtgga
        S  A  A   A  A  A  A   A  A  A  A   G  S  G   A  G  G   V  G  G
241  ggttacggag gaggtgacgg tggttatggt tcaggatctt ctgcggcagc agcagcagca
        G  Y  G   G  G  D  G   G  Y  G   S  G  S   S  A  A  A   A  A  A
301  gcggcggcag cagcagcgtc aagacgcgca gggcatgatc gtgcatatgg agctggaagt
        A  A  A   A  A  A  S   R  R  A   G  H  D   R  A  Y  G   A  G  S
361  gctgcagccg cagcagcagc agctgccgct ggcgcaggtg ctagtcgacc agtcggaatt
        A  A  A   A  A  A  A   A  A  A   G  A  G   A  S  R  P   V  G  I
421  tacggaacag acgatggctt cgtattagat ggcggttacg attcagaggg atcagcggcg
        Y  G  T   D  D  G  F   V  L  D   G  G  Y   D  S  E  G   S  A  A
481  gcggcggcag cagcagcggc agctgcggcg tcatcaagtg gtagatctac tgaaggtcat
        A  A  A   A  A  A  A   A  A  A   S  S  S   G  R  S  T   E  G  H
541  ccacttcttt cgatatgctg caggccgtgt tctcacagac atagctatga agcttccaga
        P  L  L   S  I  C   C  R  P  C   S  H  R   H  S  Y  E   A  S  R
601  atttccgtcc actaa     (SEQ ID NO: 18)
        I  S  V   H  STOP  (SEQ ID NO: 19)

Antheraea yamamai 3' homologous segment

FIGURE 10
```

```
tgcgcgcgca tcgtaaaact tcactctcat agattttca taacgcgcct aaagaagtat
aacttcaata atttaaattt aaaaaaaac atgcatagaa taattatatg aattatttaa
aatgtcattt accgacattg acataacaga cgacgttaac actacaaaac atttaattc
cacattgtta catattcaac agttaaattt gcgttaattc tcgatgcgaa caaatataag
aacaatcgga tcaattagat cgctttgttt cgaacaacac ttagtttaac tagaggcgta
caccctcaaga aatcatcttc attagaaact aaaccttaaa atcgcaataa taaagcatag
tcaatttaa ctgaaatgca aagtcttttg aacgttagat gctgtcagcg ttcgttggta
cagttgtttg atattattt taattgtctt tttatatata aatagtggaa cattaatcac
ggaatcctgt atagtatata ccgattggtc acataacaga ccactaaaat gaagcctata tttttggtat tactcgtcgc tacaTCCGGA   (SEQ ID NO: 20)
 F  L  V   L  L  V  A   T  S   G   (SEQ ID NO: 21)
                      BspEI
                                        M  K  P  I
```

Bombyx Light Chain Fibroin 5' segment

FIGURE 11

```
                XmaI
           CCCGGGctcctgagag gcgttggcaa cggtaatgac gcgaccggct
            P   G   L   L   R   G   V   G   N   G   N   D   A   T   G
tagttgctaa tgctcaaaga tatattgcac aagcagccag ccaggttcac gtcTAAataa
 L   V   A   N   A   Q   R   Y   I   A   Q   A   A   S   Q   V   H   V STOP (SEQ ID NO: 23)
gaactgtaaa taatgtatat atataattat ataaagata tatataacca tatacaaaca
tatatatcat tataagacaa tctacctata taaaaacaga ctaaaattaa taattatgta
tactttaatt gtgtttagga catttttatgc aaattgtgtt tgcgttagga tttttttttgg
aagttttttta gattatttat gaatatataa ataaatatac gttaatataa tatatattat
                                  Poly A
ataaatcaac gacacggctt ttcattttgg tgatgatcaa tcttattgtt cttctaattg
atttttttgt acaataaaga tgtatccagt tttccagata aagaatttag tttgttattt
ctggccccat taaaataagt acggtattcg acaataccac atagtatata cccaaagacg
gtggattgga cagtgggtac atggatttcg gtactgttgt catgct (SEQ ID NO: 22)
```

Bombyx Light Chain Fibroin 3' segment

FIGURE 12

```
     xhoI  Sericin 1 promotor
   1 ctcgagctca acgagccatg aataaattag aaatcaatta ataacataaa ataggcaaac
  61 aaataaaac cattacata gagaacgttt gttgaacaaa aacaataact tgtatacatt
 121 gtttgcacaa atgtttgaag cgaaaattta ttactctcta cgtaagcttg atcaaacttc
 181 gttttcgtat aaaacgcgtt ggcccaagca ctttggcata gtcgtcttat catcgggtct
                                                 eGFP
 241 ctaaggatca aacgatccaa agaccgccaa atggtgagca agggcgagga gctgttcacc
                                          M  V  S  K  G  E  E  L  F  T
 301 ggggtggtgc ccatcctggt cgagctggac ggcgacgtaa acggccacaa gttcagcgtg
      G  V  V  P  I  L  V  E  L  D  G  D  V  N  G  H  K  F  S  V
 361 tccggcgagg gcgagggcga tgccacctac ggcaagctga cccctgaagtt catctgcacc
      S  G  E  G  E  G  D  A  T  Y  G  K  L  T  L  K  F  I  C  T
 421 accggcaagc tgcccgtgcc ctggcccacc ctcgtgacca cccctcaccta cggcgtgcag
      T  G  K  L  P  V  P  W  P  T  L  V  T  T  L  T  Y  G  V  Q
 481 tgcttcagcc gctaccccga ccacatgaag cagcacgact tcttcaagtc cgccatgccc
      C  F  S  R  Y  P  D  H  M  K  Q  H  D  F  F  K  S  A  M  P
 541 gaaggctacg tccaggagcg caccatcttc ttcaaggacg acggcaacta caagacccgc
      E  G  Y  V  Q  E  R  T  I  F  F  K  D  D  G  N  Y  K  T  R
 601 gccgaggtga agttcgaggg cgacaccctg gtgaaccgca tcgagctgaa gggcatcgac
      A  E  V  K  F  E  G  D  T  L  V  N  R  I  E  L  K  G  I  D
 661 ttcaaggagg acggcaacat cctggggcac aagctggagt acaactacaa cagccacaac
      F  K  E  D  G  N  I  L  G  H  K  L  E  Y  N  Y  N  S  H  N
 721 gtctatatca tggccgacaa gcagaagaac ggcatcaagg tgaacttcaa gatccgccac
      V  Y  I  M  A  D  K  Q  K  N  G  I  K  V  N  F  K  I  R  H
 781 aacatcgagg acggcagcgt gcagctcgcc gaccactacc agcagaacac ccccatcggc
      N  I  E  D  G  S  V  Q  L  A  D  H  Y  Q  Q  N  T  P  I  G
 841 gacggccccg tgctgctgcc cgacaaccac tacctgagca cccagtccgc cctgagcaaa
      D  G  P  V  L  L  P  D  N  H  Y  L  S  T  Q  S  A  L  S  K
 901 gaccccaacg agaagcgcga tcacatggtc ctgctggagt tcgtgaccgc cgccgggatc
      D  P  N  E  K  R  D  H  M  V  L  L  E  F  V  T  A  A  G  I
 961 actctcggca tggacgagct gtacaagtaa atacaacaaa caggagtatt cctttgtagtg
      T  L  G  M  D  E  L  Y  K  stop (SEQ ID NO: 25) (Sericin 3' untranslated region)
        PolyA
1021 tttaagattt taaatcttac ttaatgactt cgaacgattt aacgataact ttctctttgt
1081 ttaactttaa tcagcataca taaaaagccc cggttttgta ccgggaagaa aaaaaatgta
1141 attgtgttgc ctagataata aacgtattat cagatct   (SEQ ID NO: 24)
                                  BglII
```

*Bombyx* Fibroin Intron GFP Insert

FIGURE 15

SEQ ID NO: 27

```
                                          amb   ocr   opl   amb
                       ocr   opl   amb    ocr   opl       Intron Start
Start Codon
ATGAGAGTCAAAACCTTTGTGATCTTGGTCtaatagtgagtaatagtgagtaatagtgagtgGCGCTCTGCAGGTGAGTTAATTATTTTACTATTATTT
 M  R  V  K  T  F  V  I  L  V                                   C  A  L  Q    (SEQ ID NO: 28)
CAGAAGGTGGCCAGACGATATCACGGGCCACCTGATAATAAGTGGTCGCCAAAACGCACAGATATCGTAAATTGTGCCATTTGATTTGTCACGCCCT GGGGGGCTACGGAATAAACTACATTTATTTATTAAAAAATGAACCTTAGATTATGTAACTTGTGATTATTTGCGTCAAAAGTAGGCAAGATGAAT CTATGTAAAATACTGGGCAGACTTGCAATATCCTATTTCACCGGTAAAATCAGCATTGCAATATGCTAAATTCAACAATATGTAAAACAATTC GTAAAGCATCATTAGAAAATAGACGAAAGAAATTGCATAAAATTATAACCGCATTATTAATTTATTGATATCTATTAACAATTGCTATTGCCTTT TTTTCGCAAATTATAATCATTTTCATAACCTCGAGGTAGCATTCTGTACATTTTAATACATTGGTATGTGATTATAACACGAGCTGCCCACTGAGTT TCTCGCCAGATCTTCTCAGTGGGTCGCGTTACCGATCACGTGATAGATTCTATGAAGCACTGCTCTTGTTAGGGCTAGTGTTAGTAAATTCTTTCAG GTTGAGTCTGAGAGCTCACCTACCCCATCGGAGCTGGAATAGGCTACCAGCTGGTAGGTAGGGAAACAAAGCTCGAAACAAGCTCAAGTAATA ACAACATAAATGTGACCATAAAATCTCGTGGTGTATGAGATACAATTATGTACTTTCCCACAAATGTTTACATAATTAGAATGTTGTTCAACTTGCCT AACGCCCCAGCTAGAACATTCAATTATTACTATTACCACTACTAAGGCAGTATGTCCTAACTCGTTCCAGATCAGCGCTAACTTCGATTGAATGTGC
                                                                                         Intron End
GAAATTTATAGCTCAATATTTAGCACTTATCGTATTGATTAAGAAAAAATTGTTAACATTTGTTTCAGTATGTCGCTTATACAAATGCAAACAT
 BspEI                                                                       Y  V  A  Y  T  N  A  N  I
CAATGATtccgga    (SEQ ID NO: 26)
 N  D  F  D      (SEQ ID NO: 29)
```

5' Homologous Sequence with Knockout insertion

FIGURE 16

FIG. 17 - SEQ ID NO: 30

ATGAGAGTCAAAACCTTTGTGATCTTGGTCTGCGCTCTGCAGGTGAGTTAATTATTTTACTATTATTTC
AGAAGGTGGCCAGACGATATCACGGGCCACCTGATAATAAGTGGTCGCCAAAACGCACAGATATCGT
AAATTGTGCCATTTGATTTGTCACGCCCTGGGGGGCTACGGAATAAACTACATTTATTTATTTAAAAAA
TGAACCTTAGATTATGTAACTTGTGATTTATTTGCGTCAAAAGTAGGCAAGATGAATCTATGTAAATAC
TGGGCAGACTTGCAATATCCTATTTCACCGGTAAAATCAGCATTGCAATATGCAATGCTAAATTCAAC
AATATGTAAAACAATTCGTAAAGCATCATTAGAAAATAGACGAAAGAAATTGCATAAAATTATAACC
GCATTATTAATTTATTATGATATCTATTAACAATTGCTATTGCCTTTTTTTCGCAAATTATAATCATTTT
CATAACCTCGAGGTAGCATTCTGTACATTTTAATACATTGGTATGTGATTATAACACGAGCTGCCCACT
GAGTTTCTCGCCAGATCTTCTCAGTGGGTCGCGTTACCGATCACGTGATAGATTCTATGAAGCACTGCT
CTTGTTAGGGCTAGTGTTAGTAAATTCTTTCAGGTTGAGTCTGAGAGCTCACCTACCCATCGGAGCGTA
GCTGGAATAGGCTACCAGCTGGTAGGTAGGGAAACAAAGCTCGAAACAAGCTCAAGTAATAACAACA
TAATGTGACCATAAAATCTCGTGGTGTATGAGATACAATTATGTACTTTCCCACAAATGTTTACATAAT
TAGAATGTTGTTCAACTTGCCTAACGCCCCAGCTAGAACATTCAATTATTACTATTACCACTACTAAGG
CAGTATGTCCTAACTCGTTCCAGATCAGCGCTAACTTCGATTGAATGTGCGAAATTTATAGCTCAATAT
TTTAGCACTTATCGTATTGATTTAAGAAAAAATTGTTAACATTTTGTTTCAGTATGTCGCTTATACAAAT
GCAAACATCAATGATTCCGGATTGGGGGGTCAGGGTGCTGCTGCTGCTGCAGCCGCTGCTGCGGGAGG
TGGGGGTCAAGGGGGAGGATATGGAGGATTAGGGTCGCAGGCTGGAAGAGGAGGAGGAAGCGGACG
AGGAGGATTAGGAGGACAAGGAGCTGCTGCTGCTGCAGCCGCTGCTGCTGGAGGAGGCGGACAAGGT
GGGTTAGGAGGTCAAGGTGCTGCGGCTGCTGCTGCTGCTGCTGCTGGAGGAGGAGGACAAGGCGGAG
GATATGGGGGTTTAGGAAGTCAGGCAGGAAGAGGAGGAGGGGGAAGAGGAGGATTGGGGGGACAAG
GAGCTGCTGCTGCTGCAGCCGCTGCTGCTGGAGGAGGAGGTCAGGGAGGAGGATATGGTGGATTAGG
AAGCCAAGCTGGAAGGGGAGGATTAGGAGGACAGGGTGCTGCAGCTGCTGCTGCGGCCGCGGCTGGA
GGGGGGGTCAGGGAGGTGGATATGGAGGATTAGGATCACAAGCTGGAAGAGGAGGATTAGGAGGA
CAGGGAGCTGCTGCAGCTGCTGCCGCTGCTGCTGGAGGAGGAGGACAAGGTGGAGGATACGGTGGGT
TGGGGAGTCAAGCAGGTAGAGGAGGAGGTTATGGAGGATTGGGAAGTCAAGCTGGAAGAGGGGGAG
GTAGTGGTCGAGGAGGAGGAGGACAAGGTGCGGCTGCTGCGGCCGCGGCTGCTGCAGGTGGAGGAGG
TCAGGGAGGATTAGGAGGTCAGGGTGGAGGACAGGGAGGTCAAGGTGCTGCTGCAGCCGCTGCAGCC
GCTGCTGGAGGGGAGGTCAGGGAGGTGGTTATGGAGGTTTAGGAAGTCAAGCAGGAAGAGGGGGAT
TAGGTGGTCAAGGAGCTGCTGCTGCTGCTGCCGCAGCGGGTGGAGGAGGGCAAGGTGGAAGTCA
GGCAGGTAGAGGAGGGTTAGGTCCCGGGGTGTCATCTGCTTCATCTCGCAGTTACGACTATTCTCGTC
GTAACGTCCGCAAAAACTGTGGAATTCCTAGAAGACAACTAGTTGTTAAATTCAGAGCACTGCCTTGT
GTGAATTGCTAATTTTTAATATAAAATAACCCTTGTTTCTTACTTCGTCCTGGATACATCTATGTTTTTT
TTTTCGTTAATAAATGAGAGCATTTAAGTTATTGTTTTTAATTACTTTTTTTTAGAAAACAGATTTCGGA
TTTTTTGTATGCATTTTATTTGAATGTACTAATATAATCAATTAATCAATGAATTCATTTATTTAAGGGA
TAACAATAATCCATGAATTCACATGCACATTTAAAACAAAACTAAATTACAATAGGTTCATATAAAAA
CAACAAGTATGCCTTCTCAACTAAGAATACTATATTGTTTAAACCGTAAAAAAAGTCATATTTCTGTAT
ATCAAAACACATCTAATATTAAAAAAACAGTCAGCAAGCACTTACAAGTGTGGGCTCGGACAGCAATT
ACCTGGTCTCAGGAGACACTTGAAGAACGAGAAGCACGTCTCTCTGTCGATTGCGAGGCTCATGCACT
ATCGCTTGAGTCTGAGACCTTTACTGATAGGGAAATCCGTTTGAGCTCTCAGAGGGTTCGGACAGCAA
AAGCTTGCCCGGTCTCAGGAGACATTAGAAGAACGGGAAGCATAACTCAATACCGATCGCGTTTCCAT
TGAGCCTATGCTTCGTGATAATAATAAATAAAGCCCAAGGTCAGACGCTAAAAGAAAGGAGATAGGA
TCCAAGCTTGGCGTAATCATGGTCATAGCTGTTTCCTGTGTGAAATTGTTATCCGCTCACAATTCCACA
CAACATACGAGCCGGAAGCATAAAGTGTAAAGCCTGGGGTGCCTAATGAGTGAGCTAACTCACATTA
ATTGCGTTGCGCTCACTGCCCGCTTTCCAGTCGGGAAACCTGTCGTGCCAGCTGCATTAATGAATCGGC
CAACGCGCGGGGAGAGGCGGTTTGCGTATTGGGCGCT

FIG. 18 - SEQ ID NO: 31

ATGAGAGTCAAAACCTTTGTGATCTTGGTCTGCGCTCTGCAGGTGAGTTAATTATTTTACTATTATTTC
AGAAGGTGGCCAGACGATATCACGGGCCACCTGATAATAAGTGGTCGCCAAAACGCACAGATATCGT
AAATTGTGCCATTTGATTTGTCACGCCCTGGGGGGCTACGGAATAAACTACATTTATTTATTTAAAAAA
TGAACCTTAGATTATGTAACTTGTGATTTATTTGCGTCAAAAGTAGGCAAGATGAATCTATGTAAATAC
TGGGCAGACTTGCAATATCCTATTTCACCGGTAAAATCAGCATTGCAATATGCAATGCTAAATTCAAC
AATATGTAAAACAATTCGTAAAGCATCATTAGAAAATAGACGAAAGAAATTGCATAAAATTATAACC
GCATTATTAATTTATTATGATATCTATTAACAATTGCTATTGCCTTTTTTTCGCAAATTATAATCATTTT
CATAACCTCGAGGTAGCATTCTGTACATTTTAATACATTGGTATGTGATTATAACACGAGCTGCCCACT
GAGTTTCTCGCCAGATCTTCTCAGTGGGTCGCGTTACCGATCACGTGATAGATTCTATGAAGCACTGCT
CTTGTTAGGGCTAGTGTTAGTAAATTCTTTCAGGTTGAGTCTGAGAGCTCACCTACCCATCGGAGCGTA
GCTGGAATAGGCTACCAGCTGGTAGGTAGGGAAACAAAGCTCGAAACAAGCTCAAGTAATAACAACA
TAATGTGACCATAAAATCTCGTGGTGTATGAGATACAATTATGTACTTTCCCACAAATGTTTACATAAT
TAGAATGTTGTTCAACTTGCCTAACGCCCCAGCTAGAACATTCAATTATTACTATTACCACTACTAAGG
CAGTATGTCCTAACTCGTTCCAGATCAGCGCTAACTTCGATTGAATGTGCGAAATTTATAGCTCAATAT
TTTAGCACTTATCGTATTGATTTAAGAAAAAATTGTTAACATTTTGTTTCAGTATGTCGCTTATACAAAT
GCAAACATCAATGATTCCGGATTGGGGGGTCAGGGTGCTGCTGCTGCTGCAGCCGCTGCTGCGGGAGG
TGGGGGTCAAGGGGGAGGATATGGAGGATTAGGGTCGCAGGCTGGAAGAGGAGGAGGAAGCGGACG
AGGAGGATTAGGAGGACAAGGAGCTGCTGCTGCTGCAGCCGCTGCTGCTGGAGGAGGCGGACAAGGT
GGGTTAGGAGGTCAAGGTGCTGCGGCTGCTGCTGCTGCTGCTGCTGGAGGAGGAGGACAAGGCGGAG
GATATGGGGGTTTAGGAAGTCAGGCAGGAAGAGGAGGAGGGGGAAGAGGAGGATTGGGGGGACAAG
GAGCTGCTGCTGCTGCAGCCGCTGCTGCTGGAGGAGGAGGTCAGGGAGGAGGATATGGTGGATTAGG
AAGCCAAGCTGGAAGGGGAGGATTAGGAGGACAGGGTGCTGCAGCTGCTGCTGCGGCCGCGGCTGGA
GGGGGGGGTCAGGGAGGTGGATATGGAGGATTAGGATCACAAGCTGGAAGAGGAGGATTAGGAGGA
CAGGGAGCTGCTGCAGCTGCTGCCGCTGCTGCTGGAGGAGGAGGACAAGGTGGAGGATACGGTGGGT
TGGGGAGTCAAGCAGGTAGAGGAGGAGGTTATGGAGGATTGGGAAGTCAAGCTGGAAGAGGGGGAG
GTAGTGGTCGAGGAGGAGGAGGACAAGGTGCGGCTGCTGCGGCCGCGGCTGCTGCAGGTGGAGGAGG
TCAGGGAGGATTAGGAGGTCAGGGTGGAGGACAGGGAGGTCAAGGTGCTGCTGCAGCCGCTGCAGCC
GCTGCTGGAGGGGGAGGTCAGGGAGGTGGTTATGGAGGTTTAGGAAGTCAAGCAGGAAGAGGGGGAT
TAGGTGGTCAAGGAGCTGCTGCTGCTGCTGCTGCCGCAGCGGGTGGAGGAGGGCAAGGTGGAAGTCA
GGCAGGTAGAGGAGGGTTAGGTCCCGGGATGGTGAGCAAGGGCGAGGAGCTGTTCACCGGGGTGGTG
CCCATCCTGGTCGAGCTGGACGGCGACGTAAACGGCCACAAGTTCAGCGTGTCCGGCGAGGGCGAGG
GCGATGCCACCTACGGCAAGCTGACCCTGAAGTTCATCTCCACCACCGGCAAGCTGCCCGTGCCCTGG
CCCACCCTCGTGACCACCCTCACCTACGGCGTGCAGGTCTTCAGCCGCTACCCCGACCACATGAAGCA
GCACGACTTCTTCAAGTCCGCCATGCCCGAAGGCTACGTCCAGGAGCGCACCATCTCTTTCAAGGACG
ACGGCAACTACAAGACCCGCGCCGAGGTGAAGTTCGAGGGCGACACCCTGGTGAACCGCATCGAGCT
GAAGGGCATCGACTTCAAGGAGGACGGCAACATCCTGGGGCACAAGCTGGAGTACAACTACAACCCC
CACAACGTCTATATCATGGCCGACAAGCAGAAGAACGGCATCAAGGTGAACTTCAAGACCGGTCACA
ACATCGAGGACGGCAGCGTGCAGCTCGCCGACCACTACCAGCAGAACACCCCCATCGGCGACGGCCC
CGTGCTGCTGCCCGACAACCACTACCTGAGCACCCAGTCCAAGCTGCTCAAAGACCCCAACGAGAAGC
GCGATCACATGGTCCTGCTGGAGTTCGTGACCGCCGCCGGGATCACTCTCGGCATGGACGAGCTGTAC
AAGGGTGTGTCATCTGCTTCATCTCGCAGTTACGACTATTCTCGTCGTAACGTCCGCAAAAACTGTGGA
ATTCCTAGAAGACAACTAGTTGTTAAATTCAGAGCACTGCCTTGTGTGAATTGCTAATTTTTAATATAA
AATAACCCTTGTTTCTTACTTCGTCCTGGATACATCTATGTTTTTTTTTCGTTAATAAATGAGAGCATT
TAAGTTATTGTTTTTAATTACTTTTTTTTAGAAAACAGATTTCGGATTTTTTGTATGCATTTTATTTGAAT
GTACTAATATAATCAATTAATCAATGAATTCATTTATTTAAGGGATAACAATAATCCATGAATTCACAT
GCACATTTAAAACAAAACTAAATTACAATAGGTTCATATAAAAACAACAAGTATGCCTTCTCAACTAA

FIG. 18 - SEQ ID NO: 31 Continued

GAATACTATATTGTTTAAACCGTAAAAAAAGTCATATTTCTGTATATCAAAACACATCTAATATTAAAA
AAACAGTCAGCAAGCACTTACAAGTGTGGGCTCGGACAGCAATTACCTGGTCTCAGGAGACACTTGAA
GAACGAGAAGCACGTCTCTCTGTCGATTGCGAGGCTCATGCACTATCGCTTGAGTCTGAGACCTTTACT
GATAGGGAAATCCGTTTGAGCTCTCAGAGGGTTCGGACAGCAAAAGCTTGCCCGGTCTCAGGAGACAT
TAGAAGAACGGGAAGCATAACTCAATACCGATCGCGTTTCCATTGAGCCTATGCTTCGTGATAATAAT
AAATAAAGCCCAAGGTCAGACGCTAAAAGAAAGGAGATAGGATCCAAGCTTGGCGTAATCATGGTCA
TAGCTGTTTCCTGTGTGAAATTGTTATCCGCTCACAATTCCACACAACATACGAGCCGGAAGCATAAA
GTGTAAAGCCTGGGGTGCCTAATGAGTGAGCTAACTCACATTAATTGCGTTGCGCTCACTGCCCGCTTT
CCAGTCGGGAAACCTGTCGTGCCAGCTGCATTAATGAATCGGCCAACGCGCGGGGAGAGGCGGTTTGC
GTATTGGGCGCT

FIG. 19 - SEQ ID NO: 32
ATGAGAGTCAAAACCTTTGTGATCTTGGTCTGCGCTCTGCAGGTGAGTTAATTATTTTACTATTATTTC
AGAAGGTGGCCAGACGATATCACGGGCCACCTGATAATAAGTGGTCGCCAAAACGCACAGATATCGT
AAATTGTGCCATTTGATTTGTCACGCCCTGGGGGGCTACGGAATAAACTACATTTATTTATTTAAAAAA
TGAACCTTAGATTATGTAACTTGTGATTTATTTGCGTCAAAAGTAGGCAAGATGAATCTATGTAAATAC
TGGGCAGACTTGCAATATCCTATTTCACCGGTAAAATCAGCATTGCAATATGCAATGCTAAATTCAAC
AATATGTAAAACAATTCGTAAAGCATCATTAGAAAATAGACGAAAGAAATTGCATAAAATTATAACC
GCATTATTAATTTATTATGATATCTATTAACAATTGCTATTGCCTTTTTTTCGCAAATTATAATCATTTT
CATAACCTCGAGGTAGCATTCTGTACATTTTAATACATTGGTATGTGATTATAACACGAGCTGCCCACT
GAGTTTCTCGCCAGATCTTCTCAGTGGGTCGCGTTACCGATCACGTGATAGATTCTATGAAGCACTGCT
CTTGTTAGGGCTAGTGTTAGTAAATTCTTTCAGGTTGAGTCTGAGAGCTCACCTACCCATCGGAGCGTA
GCTGGAATAGGCTACCAGCTGGTAGGTAGGGAAACAAAGCTCGAAACAAGCTCAAGTAATAACAACA
TAATGTGACCATAAAATCTCGTGGTGTATGAGATACAATTATGTACTTTCCCACAAATGTTTACATAAT
TAGAATGTTGTTCAACTTGCCTAACGCCCCAGCTAGAACATTCAATTATTACTATTACCACTACTAAGG
CAGTATGTCCTAACTCGTTCCAGATCAGCGCTAACTTCGATTGAATGTGCGAAATTTATAGCTCAATAT
TTTAGCACTTATCGTATTGATTTAAGAAAAAATTGTTAACATTTTGTTTCAGTATGTCGCTTATACAAAT
GCAAACATCAATGATTCCGGATTGGGGGGTCAGGGTGCTGCTGCTGCTGCAGCCGCTGCTGCGGGAGG
TGGGGGTCAAGGGGGAGGATATGGAGGATTAGGGTCGCAGGCTGGAAGAGGAGGAGGAAGCGGACG
AGGAGGATTAGGAGGACAAGGAGCTGCTGCTGCTGCAGCCGCTGCTGCTGGAGGAGGCGGACAAGGT
GGGTTAGGAGGTCAAGGTGCTGCGGCTGCTGCTGCTGCTGCTGCTGGAGGAGGAGGACAAGGCGGAG
GATATGGGGGTTTAGGAAGTCAGGCAGGAAGAGGAGGAGGGGGAAGAGGAGGATTGGGGGGACAAG
GAGCTGCTGCTGCTGCAGCCGCTGCTGCTGGAGGAGGAGGTCAGGGAGGAGGATATGGTGGATTAGG
AAGCCAAGCTGGAAGGGGAGGATTAGGAGGACAGGGTGCTGCAGCTGCTGCTGCGGCCGCGGCTGGA
GGGGGGGGTCAGGGAGGTGGATATGGAGGATTAGGATCACAAGCTGGAAGAGGAGGATTAGGAGGA
CAGGGAGCTGCTGCAGCTGCTGCCGCTGCTGCTGGAGGAGGAGGACAAGGTGGAGGATACGGTGGGT
TGGGGAGTCAAGCAGGTAGAGGAGGAGGTTATGGAGGATTGGGAAGTCAAGCTGGAAGAGGGGGAG
GTAGTGGTCGAGGAGGAGGAGGACAAGGTGCGGCTGCTGCGGCCGCGGCTGCTGCAGGTGGAGGAGG
TCAGGGAGGATTAGGAGGTCAGGGTGGAGGACAGGGAGGTCAAGGTGCTGCTGCAGCCGCTGCAGCC
GCTGCTGGAGGGGAGGTCAGGGAGGTGGTTATGGAGGTTTAGGAAGTCAAGCAGGAAGAGGGGGAT
TAGGTGGTCAAGGAGCTGCTGCTGCTGCTGCCGCAGCGGGTGGAGGAGGGCAAGGTGGAAGTCA
GGCAGGTAGAGGAGGGTTAGGTtcCgggTTGGGGGGTCAGGGTGCTGCTGCTGCTGCAGCCGCTGCTGC
GGGAGGTGGGGGTCAAGGGGGAGGATATGGAGGATTAGGGTCGCAGGCTGGAAGAGGAGGAGGAAG
CGGACGAGGAGGATTAGGAGGACAAGGAGCTGCTGCTGCTGCAGCCGCTGCTGCTGGAGGAGGCGGA
CAAGGTGGGTTAGGAGGTCAAGGTGCTGCGGCTGCTGCTGCTGCTGCTGGAGGAGGAGGACAAG
GCGGAGGATATGGGGGTTTAGGAAGTCAGGCAGGAAGAGGAGGAGGGGGAAGAGGAGGATTGGGGG
GACAAGGAGCTGCTGCTGCTGCAGCCGCTGCTGCTGGAGGAGGAGGTCAGGGAGGAGGATATGGTGG
ATTAGGAAGCCAAGCTGGAAGGGGAGGATTAGGAGGACAGGGTGCTGCAGCTGCTGCTGCGGCCGCG
GCTGGAGGGGGGGGTCAGGGAGGTGGATATGGAGGATTAGGATCACAAGCTGGAAGAGGAGGATTA
GGAGGACAGGGAGCTGCTGCAGCTGCTGCCGCTGCTGCTGGAGGAGGAGGACAAGGTGGAGGATACG
GTGGGTTGGGGAGTCAAGCAGGTAGAGGAGGAGGTTATGGAGGATTGGGAAGTCAAGCTGGAAGAG
GGGGAGGTAGTGGTCGAGGAGGAGGAGGACAAGGTGCGGCTGCTGCGGCCGCGGCTGCTGCAGGTGG
AGGAGGTCAGGGAGGATTAGGAGGTCAGGGTGGAGGACAGGGAGGTCAAGGTGCTGCTGCAGCCGCT
GCAGCCGCTGCTGGAGGGGAGGTCAGGGAGGTGGTTATGGAGGTTTAGGAAGTCAAGCAGGAAGAG
GGGGATTAGGTGGTCAAGGAGCTGCTGCTGCTGCTGCCGCAGCGGGTGGAGGAGGGCAAGGTGG
AAGTCAGGCAGGTAGAGGAGGGTTAGGTccCgggGTGTCATCTGCTTCATCTCGCAGTTACGACTATTCT
CGTCGTAACGTCCGCAAAAACTGTGGAATTCCTAGAAGACAACTAGTTGTTAAATTCAGAGCACTGCC

FIG. 19 - SEQ ID NO: 32 Continued

TTGTGTGAATTGCTAATTTTTAATATAAAATAACCCTTGTTTCTTACTTCGTCCTGGATACATCTATGTT
TTTTTTTCGTTAATAAATGAGAGCATTTAAGTTATTGTTTTTAATTACTTTTTTTTAGAAAACAGATTT
CGGATTTTTTGTATGCATTTTATTTGAATGTACTAATATAATCAATTAATCAATGAATTCATTTATTTAA
GGGATAACAATAATCCATGAATTCACATGCACATTTAAAACAAAACTAAATTACAATAGGTTCATATA
AAAACAACAAGTATGCCTTCTCAACTAAGAATACTATATTGTTTAAACCGTAAAAAAAGTCATATTTC
TGTATATCAAAACACATCTAATATTAAAAAAACAGTCAGCAAGCACTTACAAGTGTGGGCTCGGACAG
CAATTACCTGGTCTCAGGAGACACTTGAAGAACGAGAAGCACGTCTCTCTGTCGATTGCGAGGCTCAT
GCACTATCGCTTGAGTCTGAGACCTTTACTGATAGGGAAATCCGTTTGAGCTCTCAGAGGGTTCGGAC
AGCAAAAGCTTGCCCGGTCTCAGGAGACATTAGAAGAACGGGAAGCATAACTCAATACCGATCGCGT
TTCCATTGAGCCTATGCTTCGTGATAATAATAAATAAAGCCCAAGGTCAGACGCTAAAAGAAAGGAGA
TAGGATCCAAGCTTGGCGTAATCATGGTCATAGCTGTTTCCTGTGTGAAATTGTTATCCGCTCACAATT
CCACACAACATACGAGCCGGAAGCATAAAGTGTAAAGCCTGGGGTGCCTAATGAGTGAGCTAACTCA
CATTAATTGCGTTGCGCTCACTGCCCGCTTTCCAGTCGGGAAACCTGTCGTGCCAGCTGCATTAATGAA
TCGGCCAACGCGCGGGGAGAGGCGGTTTGCGTATTGGGCGCT

FIG. 20 - SEQ ID NO: 33
ATGAGAGTCAAAACCTTTGTGATCTTGGTCTGCGCTCTGCAGGTGAGTTAATTATTTTACTATTATTTC
AGAAGGTGGCCAGACGATATCACGGGCCACCTGATAATAAGTGGTCGCCAAAACGCACAGATATCGT
AAATTGTGCCATTTGATTTGTCACGCCCTGGGGGGCTACGGAATAAACTACATTTATTTATTTAAAAAA
TGAACCTTAGATTATGTAACTTGTGATTTATTTGCGTCAAAAGTAGGCAAGATGAATCTATGTAAATAC
TGGGCAGACTTGCAATATCCTATTTCACCGGTAAAATCAGCATTGCAATATGCAATGCTAAATTCAAC
AATATGTAAAACAATTCGTAAAGCATCATTAGAAAATAGACGAAAGAAATTGCATAAAATTATAACC
GCATTATTAATTTATTATGATATCTATTAACAATTGCTATTGCCTTTTTTTCGCAAATTATAATCATTTT
CATAACCTCGAGGTAGCATTCTGTACATTTTAATACATTGGTATGTGATTATAACACGAGCTGCCCACT
GAGTTTCTCGCCAGATCTTCTCAGTGGGTCGCGTTACCGATCACGTGATAGATTCTATGAAGCACTGCT
CTTGTTAGGGCTAGTGTTAGTAAATTCTTTCAGGTTGAGTCTGAGAGCTCACCTACCCATCGGAGCGTA
GCTGGAATAGGCTACCAGCTGGTAGGTAGGGAAACAAAGCTCGAAACAAGCTCAAGTAATAACAACA
TAATGTGACCATAAAATCTCGTGGTGTATGAGATACAATTATGTACTTTCCCACAAATGTTTACATAAT
TAGAATGTTGTTCAACTTGCCTAACGCCCCAGCTAGAACATTCAATTATTACTATTACCACTACTAAGG
CAGTATGTCCTAACTCGTTCCAGATCAGCGCTAACTTCGATTGAATGTGCGAAATTTATAGCTCAATAT
TTTAGCACTTATCGTATTGATTTAAGAAAAAATTGTTAACATTTTGTTTCAGTATGTCGCTTATACAAAT
GCAAACATCAATGATTCCGGATTGGGGGGTCAGGGTGCTGCTGCTGCTGCAGCCGCTGCTGCGGGAGG
TGGGGGTCAAGGGGGAGGATATGGAGGATTAGGGTCGCAGGCTGGAAGAGGAGGAGGAAGCGGACG
AGGAGGATTAGGAGGACAAGGAGCTGCTGCTGCTGCAGCCGCTGCTGCTGGAGGAGGCGGACAAGGT
GGGTTAGGAGGTCAAGGTGCTGCGGCTGCTGCTGCTGCTGCTGCTGGAGGAGGAGGACAAGGCGGAG
GATATGGGGGTTTAGGAAGTCAGGCAGGAAGAGGAGGAGGGGGAAGAGGAGGATTGGGGGGACAAG
GAGCTGCTGCTGCTGCAGCCGCTGCTGCTGGAGGAGGAGGTCAGGGAGGAGGATATGGTGGATTAGG
AAGCCAAGCTGGAAGGGGAGGATTAGGAGGACAGGGTGCTGCAGCTGCTGCTGCGGCCGCGGCTGGA
GGGGGGGGTCAGGGAGGTGGATATGGAGGATTAGGATCACAAGCTGGAAGAGGAGGATTAGGAGGA
CAGGGAGCTGCTGCAGCTGCTGCCGCTGCTGCTGGAGGAGGAGGACAAGGTGGAGGATACGGTGGGT
TGGGGAGTCAAGCAGGTAGAGGAGGAGGTTATGGAGGATTGGGAAGTCAAGCTGGAAGAGGGGGAG
GTAGTGGTCGAGGAGGAGGAGGACAAGGTGCGGCTGCTGCGGCCGCGGCTGCTGCAGGTGGAGGAGG
TCAGGGAGGATTAGGAGGTCAGGGTGGAGGACAGGGAGGTCAAGGTGCTGCTGCAGCCGCTGCAGCC
GCTGCTGGAGGGGAGGTCAGGGAGGTGGTTATGGAGGTTTAGGAAGTCAAGCAGGAAGAGGGGGAT
TAGGTGGTCAAGGAGCTGCTGCTGCTGCTGCCGCAGCGGGTGGAGGAGGGCAAGGTGGAAGTCA
GGCAGGTAGAGGAGGGTTAGGTtcCgggTTGGGGGGTCAGGGTGCTGCTGCTGCTGCAGCCGCTGCTGC
GGGAGGTGGGGGTCAAGGGGGAGGATATGGAGGATTAGGGTCGCAGGCTGGAAGAGGAGGAGGAAG
CGGACGAGGAGGATTAGGAGGACAAGGAGCTGCTGCTGCTGCAGCCGCTGCTGCTGGAGGAGGCGGA
CAAGGTGGGTTAGGAGGTCAAGGTGCTGCGGCTGCTGCTGCTGCTGCTGGAGGAGGAGGACAAG
GCGGAGGATATGGGGGTTTAGGAAGTCAGGCAGGAAGAGGAGGAGGGGGAAGAGGAGGATTGGGGG
GACAAGGAGCTGCTGCTGCTGCAGCCGCTGCTGCTGGAGGAGGAGGTCAGGGAGGAGGATATGGTGG
ATTAGGAAGCCAAGCTGGAAGGGGAGGATTAGGAGGACAGGGTGCTGCAGCTGCTGCTGCGGCCGCG
GCTGGAGGGGGGGTCAGGGAGGTGGATATGGAGGATTAGGATCACAAGCTGGAAGAGGAGGATTA
GGAGGACAGGGAGCTGCTGCAGCTGCTGCCGCTGCTGCTGGAGGAGGAGGACAAGGTGGAGGATACG
GTGGGTTGGGGAGTCAAGCAGGTAGAGGAGGAGGTTATGGAGGATTGGGAAGTCAAGCTGGAAGAG
GGGGAGGTAGTGGTCGAGGAGGAGGAGGACAAGGTGCGGCTGCTGCGGCCGCGGCTGCTGCAGGTGG
AGGAGGTCAGGGAGGATTAGGAGGTCAGGGTGGAGGACAGGGAGGTCAAGGTGCTGCTGCAGCCGCT
GCAGCCGCTGCTGGAGGGGAGGTCAGGGAGGTGGTTATGGAGGTTTAGGAAGTCAAGCAGGAAGAG
GGGGATTAGGTGGTCAAGGAGCTGCTGCTGCTGCTGCCGCAGCGGGTGGAGGAGGGCAAGGTGG
AAGTCAGGCAGGTAGAGGAGGGTTAGGTccCgggATGGTGAGCAAGGGCGAGGAGCTGTTCACCGGGG
TGGTGCCCATCCTGGTCGAGCTGGACGGCGACGTAAACGGCCACAAGTTCAGCGTGTCCGGCGAGGGC

FIG. 20 - SEQ ID NO: 33 Continued

GAGGGCGATGCCACCTACGGCAAGCTGACCCTGAAGTTCATCTCCACCACCGGCAAGCTGCCCGTGCC
CTGGCCCACCCTCGTGACCACCCTCACCTACGGCGTGCAGGTCTTCAGCCGCTACCCCGACCACATGA
AGCAGCACGACTTCTTCAAGTCCGCCATGCCCGAAGGCTACGTCCAGGAGCGCACCATCTCTTTCAAG
GACGACGGCAACTACAAGACCCGCGCCGAGGTGAAGTTCGAGGGCGACACCCTGGTGAACCGCATCG
AGCTGAAGGGCATCGACTTCAAGGAGGACGGCAACATCCTGGGGCACAAGCTGGAGTACAACTACAA
CCCCCACAACGTCTATATCATGGCCGACAAGCAGAAGAACGGCATCAAGGTGAACTTCAAGACCGGT
CACAACATCGAGGACGGCAGCGTGCAGCTCGCCGACCACTACCAGCAGAACACCCCCATCGGCGACG
GCCCCGTGCTGCTGCCCGACAACCACTACCTGAGCACCCAGTCCAAGCTGCTCAAAGACCCCAACGAG
AAGCGCGATCACATGGTCCTGCTGGAGTTCGTGACCGCCGCCGGGATCACTCTCGGCATGGACGAGCT
GTACAAGGGTGTGTCATCTGCTTCATCTCGCAGTTACGACTATTCTCGTCGTAACGTCCGCAAAAACTG
TGGAATTCCTAGAAGACAACTAGTTGTTAAATTCAGAGCACTGCCTTGTGTGAATTGCTAATTTTTAAT
ATAAAATAACCCTTGTTTCTTACTTCGTCCTGGATACATCTATGTTTTTTTTTCGTTAATAAATGAGAG
CATTTAAGTTATTGTTTTAATTACTTTTTTTTAGAAAACAGATTTCGGATTTTTTGTATGCATTTTATTT
GAATGTACTAATATAATCAATTAATCAATGAATTCATTTATTTAAGGGATAACAATAATCCATGAATTC
ACATGCACATTTAAAACAAAACTAAATTACAATAGGTTCATATAAAAACAACAAGTATGCCTTCTCAA
CTAAGAATACTATATTGTTTAAACCGTAAAAAAAGTCATATTTCTGTATATCAAAACACATCTAATATT
AAAAAAACAGTCAGCAAGCACTTACAAGTGTGGGCTCGGACAGCAATTACCTGGTCTCAGGAGACAC
TTGAAGAACGAGAAGCACGTCTCTCTGTCGATTGCGAGGCTCATGCACTATCGCTTGAGTCTGAGACC
TTTACTGATAGGGAAATCCGTTTGAGCTCTCAGAGGGTTCGGACAGCAAAAGCTTGCCCGGTCTCAGG
AGACATTAGAAGAACGGGAAGCATAACTCAATACCGATCGCGTTTCCATTGAGCCTATGCTTCGTGAT
AATAATAAATAAAGCCCAAGGTCAGACGCTAAAAGAAAGGAGATAGGATCCAAGCTTGGCGTAATCA
TGGTCATAGCTGTTTCCTGTGTGAAATTGTTATCCGCTCACAATTCCACACAACATACGAGCCGGAAGC
ATAAAGTGTAAAGCCTGGGGTGCCTAATGAGTGAGCTAACTCACATTAATTGCGTTGCGCTCACTGCC
CGCTTTCCAGTCGGGAAACCTGTCGTGCCAGCTGCATTAATGAATCGGCCAACGCGCGGGGAGAGGCG
GTTTGCGTATTGGGCGCT

FIG. 21 - SEQ ID NO: 34

ATGAGAGTCAAAACCTTTGTGATCTTGGTCTGCGCTCTGCAGGTGAGTTAATTATTTTACTATTATTTC
AGAAGGTGGCCAGACGATATCACGGGCCACCTGATAATAAGTGGTCGCCAAAACGCACAGATATCGT
AAATTGTGCCATTTGATTTGTCACGCCCTGGGGGGCTACGGAATAAACTACATTTATTTATTTAAAAAA
TGAACCTTAGATTATGTAACTTGTGATTTATTTGCGTCAAAAGTAGGCAAGATGAATCTATGTAAATAC
TGGGCAGACTTGCAATATCCTATTTCACCGGTAAAATCAGCATTGCAATATGCAATGCTAAATTCAAC
AATATGTAAAACAATTCGTAAAGCATCATTAGAAAATAGACGAAAGAAATTGCATAAAATTATAACC
GCATTATTAATTTATTATGATATCTATTAACAATTGCTATTGCCTTTTTTTCGCAAATTATAATCATTTT
CATAACCTCGAGGTAGCATTCTGTACATTTTAATACATTGGTATGTGATTATAACACGAGCTGCCCACT
GAGTTTCTCGCCAGATCTTCTCAGTGGGTCGCGTTACCGATCACGTGATAGATTCTATGAAGCACTGCT
CTTGTTAGGGCTAGTGTTAGTAAATTCTTTCAGGTTGAGTCTGAGAGCTCACCTACCCATCGGAGCGTA
GCTGGAATAGGCTACCAGCTGGTAGGTAGGGAAACAAAGCTCGAAACAAGCTCAAGTAATAACAACA
TAATGTGACCATAAAATCTCGTGGTGTATGAGATACAATTATGTACTTTCCCACAAATGTTTACATAAT
TAGAATGTTGTTCAACTTGCCTAACGCCCCAGCTAGAACATTCAATTATTACTATTACCACTACTAAGG
CAGTATGTCCTAACTCGTTCCAGATCAGCGCTAACTTCGATTGAATGTGCGAAATTTATAGCTCAATAT
TTTAGCACTTATCGTATTGATTTAAGAAAAAATTGTTAACATTTTGTTTCAGTATGTCGCTTATACAAAT
GCAAACATCAATGATTCCGGATTGGGGGGTCAGGGTGCTGCTGCTGCTGCAGCCGCTGCTGCGGGAGG
TGGGGGTCAAGGGGGAGGATATGGAGGATTAGGGTCGCAGGCTGGAAGAGGAGGAGGAAGCGGACG
AGGAGGATTAGGAGGACAAGGAGCTGCTGCTGCTGCAGCCGCTGCTGCTGGAGGAGGCGGACAAGGT
GGGTTAGGAGGTCAAGGTGCTGCGGCTGCTGCTGCTGCTGCTGCTGGAGGAGGAGGACAAGGCGGAG
GATATGGGGGTTTAGGAAGTCAGGCAGGAAGAGGAGGAGGGGGAAGAGGAGGATTGGGGGGACAAG
GAGCTGCTGCTGCTGCAGCCGCTGCTGCTGGAGGAGGAGGTCAGGGAGGAGGATATGGTGGATTAGG
AAGCCAAGCTGGAAGGGGAGGATTAGGAGGACAGGGTGCTGCAGCTGCTGCTGCGGCCGCGGCTGGA
GGGGGGGTCAGGGAGGTGGATATGGAGGATTAGGATCACAAGCTGGAAGAGGAGGATTAGGAGGA
CAGGGAGCTGCTGCAGCTGCTGCCGCTGCTGCTGGAGGAGGAGGACAAGGTGGAGGATACGGTGGGT
TGGGGAGTCAAGCAGGTAGAGGAGGAGGTTATGGAGGATTGGGAAGTCAAGCTGGAAGAGGGGGAG
GTAGTGGTCGAGGAGGAGGAGGACAAGGTGCGGCTGCTGCGGCCGCGGCTGCTGCAGGTGGAGGAGG
TCAGGGAGGATTAGGAGGTCAGGGTGGAGGACAGGGAGGTCAAGGTGCTGCTGCAGCCGCTGCAGCC
GCTGCTGGAGGGGAGGTCAGGGAGGTGGTTATGGAGGTTTAGGAAGTCAAGCAGGAAGAGGGGAT
TAGGTGGTCAAGGAGCTGCTGCTGCTGCTGCCGCAGCGGGTGGAGGAGGGCAAGGTGGAAGTCA
GGCAGGTAGAGGAGGGTTAGGTtcCgggTTGGGGGGTCAGGGTGCTGCTGCTGCTGCAGCCGCTGCTGC
GGGAGGTGGGGGTCAAGGGGGAGGATATGGAGGATTAGGGTCGCAGGCTGGAAGAGGAGGAGGAAG
CGGACGAGGAGGATTAGGAGGACAAGGAGCTGCTGCTGCTGCAGCCGCTGCTGCTGGAGGAGGCGGA
CAAGGTGGGTTAGGAGGTCAAGGTGCTGCGGCTGCTGCTGCTGCTGCTGGAGGAGGAGGACAAG
GCGGAGGATATGGGGGTTTAGGAAGTCAGGCAGGAAGAGGAGGAGGGGGAAGAGGAGGATTGGGGG
GACAAGGAGCTGCTGCTGCTGCAGCCGCTGCTGCTGGAGGAGGAGGTCAGGGAGGAGGATATGGTGG
ATTAGGAAGCCAAGCTGGAAGGGGAGGATTAGGAGGACAGGGTGCTGCAGCTGCTGCTGCGGCCGCG
GCTGGAGGGGGGGTCAGGGAGGTGGATATGGAGGATTAGGATCACAAGCTGGAAGAGGAGGATTA
GGAGGACAGGGAGCTGCTGCAGCTGCTGCCGCTGCTGCTGGAGGAGGAGGACAAGGTGGAGGATACG
GTGGGTTGGGGAGTCAAGCAGGTAGAGGAGGAGGTTATGGAGGATTGGGAAGTCAAGCTGGAAGAG
GGGGAGGTAGTGGTCGAGGAGGAGGAGGACAAGGTGCGGCTGCTGCGGCCGCGGCTGCTGCAGGTGG
AGGAGGTCAGGGAGGATTAGGAGGTCAGGGTGGAGGACAGGGAGGTCAAGGTGCTGCTGCAGCCGCT
GCAGCCGCTGCTGGAGGGGAGGTCAGGGAGGTGGTTATGGAGGTTTAGGAAGTCAAGCAGGAAGAG
GGGGATTAGGTGGTCAAGGAGCTGCTGCTGCTGCTGCCGCAGCGGGTGGAGGAGGGCAAGGTGG
AAGTCAGGCAGGTAGAGGAGGGTTAGGTtcCgggTTGGGGGGTCAGGGTGCTGCTGCTGCTGCAGCCGC
TGCTGCGGGAGGTGGGGGTCAAGGGGGAGGATATGGAGGATTAGGGTCGCAGGCTGGAAGAGGAGG

FIG. 21 - SEQ ID NO: 34 Continued

AGGAAGCGGACGAGGAGGATTAGGAGGACAAGGAGCTGCTGCTGCTGCAGCCGCTGCTGCTGGAGGA
GGCGGACAAGGTGGGTTAGGAGGTCAAGGTGCTGCGGCTGCTGCTGCTGCTGCTGGAGGAGGAG
GACAAGGCGGAGGATATGGGGGTTTAGGAAGTCAGGCAGGAAGAGGAGGAGGGGAAGAGGAGGAT
TGGGGGGACAAGGAGCTGCTGCTGCTGCAGCCGCTGCTGCTGGAGGAGGAGGTCAGGGAGGAGGATA
TGGTGGATTAGGAAGCCAAGCTGGAAGGGGAGGATTAGGAGGACAGGGTGCTGCAGCTGCTGCTGCG
GCCGCGGCTGGAGGGGGGGGTCAGGGAGGTGGATATGGAGGATTAGGATCACAAGCTGGAAGAGGA
GGATTAGGAGGACAGGGAGCTGCTGCAGCTGCTGCCGCTGCTGCTGGAGGAGGAGGACAAGGTGGAG
GATACGGTGGGTTGGGGAGTCAAGCAGGTAGAGGAGGAGGTTATGGAGGATTGGGAAGTCAAGCTGG
AAGAGGGGGAGGTAGTGGTCGAGGAGGAGGAGGACAAGGTGCGGCTGCTGCGGCCGCGGCTGCTGC
AGGTGGAGGAGGTCAGGGAGGATTAGGAGGTCAGGGTGGAGGACAGGGAGGTCAAGGTGCTGCTGC
AGCCGCTGCAGCCGCTGCTGGAGGGGGAGGTCAGGGAGGTGGTTATGGAGGTTTAGGAAGTCAAGCA
GGAAGAGGGGGATTAGGTGGTCAAGGAGCTGCTGCTGCTGCTGCTGCCGCAGCGGGTGGAGGAGGGC
AAGGTGGAAGTCAGGCAGGTAGAGGAGGGTTAGGTccCgggGTGTCATCTGCTTCATCTCGCAGTTACG
ACTATTCTCGTCGTAACGTCCGCAAAAACTGTGGAATTCCTAGAAGACAACTAGTTGTTAAATTCAGA
GCACTGCCTTGTGTGAATTGCTAATTTTTAATATAAAATAACCCTTGTTTCTTACTTCGTCCTGGATACA
TCTATGTTTTTTTTTCGTTAATAAATGAGAGCATTTAAGTTATTGTTTTTAATTACTTTTTTTTAGAAAA
CAGATTTCGGATTTTTTGTATGCATTTTATTTGAATGTACTAATATAATCAATTAATCAATGAATTCATT
TATTTAAGGGATAACAATAATCCATGAATTCACATGCACATTTAAAACAAAACTAAATTACAATAGGT
TCATATAAAAACAACAAGTATGCCTTCTCAACTAAGAATACTATATTGTTTAAACCGTAAAAAAAGTC
ATATTTCTGTATATCAAAACACATCTAATATTAAAAAAACAGTCAGCAAGCACTTACAAGTGTGGGCT
CGGACAGCAATTACCTGGTCTCAGGAGACACTTGAAGAACGAGAAGCACGTCTCTCTGTCGATTGCGA
GGCTCATGCACTATCGCTTGAGTCTGAGACCTTTACTGATAGGGAAATCCGTTTGAGCTCTCAGAGGGT
TCGGACAGCAAAAGCTTGCCCGGTCTCAGGAGACATTAGAAGAACGGGAAGCATAACTCAATACCGA
TCGCGTTTCCATTGAGCCTATGCTTCGTGATAATAATAAATAAAGCCCAAGGTCAGACGCTAAAAGAA
AGGAGATAGGATCCAAGCTTGGCGTAATCATGGTCATAGCTGTTTCCTGTGTGAAATTGTTATCCGCTC
ACAATTCCACACAACATACGAGCCGGAAGCATAAAGTGTAAAGCCTGGGGTGCCTAATGAGTGAGCT
AACTCACATTAATTGCGTTGCGCTCACTGCCCGCTTTCCAGTCGGGAAACCTGTCGTGCCAGCTGCATT
AATGAATCGGCCAACGCGCGGGGAGAGGCGGTTTGCGTATTGGGCGCT

FIG. 22 - SEQ ID NO: 35
ATGAGAGTCAAAACCTTTGTGATCTTGGTCTGCGCTCTGCAGGTGAGTTAATTATTTTACTATTATTTC
AGAAGGTGGCCAGACGATATCACGGGCCACCTGATAATAAGTGGTCGCCAAAACGCACAGATATCGT
AAATTGTGCCATTTGATTTGTCACGCCCTGGGGGGCTACGGAATAAACTACATTTATTTATTTAAAAAA
TGAACCTTAGATTATGTAACTTGTGATTTATTTGCGTCAAAAGTAGGCAAGATGAATCTATGTAAATAC
TGGGCAGACTTGCAATATCCTATTTCACCGGTAAAATCAGCATTGCAATATGCAATGCTAAATTCAAC
AATATGTAAAACAATTCGTAAAGCATCATTAGAAAATAGACGAAAGAAATTGCATAAAATTATAACC
GCATTATTAATTTATTATGATATCTATTAACAATTGCTATTGCCTTTTTTTCGCAAATTATAATCATTTT
CATAACCTCGAGGTAGCATTCTGTACATTTTAATACATTGGTATGTGATTATAACACGAGCTGCCCACT
GAGTTTCTCGCCAGATCTTCTCAGTGGGTCGCGTTACCGATCACGTGATAGATTCTATGAAGCACTGCT
CTTGTTAGGGCTAGTGTTAGTAAATTCTTTCAGGTTGAGTCTGAGAGCTCACCTACCCATCGGAGCGTA
GCTGGAATAGGCTACCAGCTGGTAGGTAGGGAAACAAAGCTCGAAACAAGCTCAAGTAATAACAACA
TAATGTGACCATAAAATCTCGTGGTGTATGAGATACAATTATGTACTTTCCCACAAATGTTTACATAAT
TAGAATGTTGTTCAACTTGCCTAACGCCCCAGCTAGAACATTCAATTATTACTATTACCACTACTAAGG
CAGTATGTCCTAACTCGTTCCAGATCAGCGCTAACTTCGATTGAATGTGCGAAATTTATAGCTCAATAT
TTTAGCACTTATCGTATTGATTTAAGAAAAAATTGTTAACATTTTGTTTCAGTATGTCGCTTATACAAAT
GCAAACATCAATGATTCCGGATTGGGGGGTCAGGGTGCTGCTGCTGCTGCAGCCGCTGCTGCGGGAGG
TGGGGGTCAAGGGGGAGGATATGGAGGATTAGGGTCGCAGGCTGGAAGAGGAGGAGGAAGCGGACG
AGGAGGATTAGGAGGACAAGGAGCTGCTGCTGCTGCAGCCGCTGCTGCTGGAGGAGGCGGACAAGGT
GGGTTAGGAGGTCAAGGTGCTGCGGCTGCTGCTGCTGCTGCTGCTGGAGGAGGAGGACAAGGCGGAG
GATATGGGGGTTTAGGAAGTCAGGCAGGAAGAGGAGGAGGGGGAAGAGGAGGATTGGGGGGACAAG
GAGCTGCTGCTGCTGCAGCCGCTGCTGCTGGAGGAGGAGGTCAGGGAGGAGGATATGGTGGATTAGG
AAGCCAAGCTGGAAGGGGAGGATTAGGAGGACAGGGTGCTGCAGCTGCTGCTGCGGCCGCGGCTGGA
GGGGGGGTCAGGGAGGTGGATATGGAGGATTAGGATCACAAGCTGGAAGAGGAGGATTAGGAGGA
CAGGGAGCTGCTGCAGCTGCTGCCGCTGCTGCTGGAGGAGGAGGACAAGGTGGAGGATACGGTGGGT
TGGGGAGTCAAGCAGGTAGAGGAGGAGGTTATGGAGGATTGGGAAGTCAAGCTGGAAGAGGGGGAG
GTAGTGGTCGAGGAGGAGGAGGACAAGGTGCGGCTGCTGCGGCCGCGGCTGCTGCAGGTGGAGGAGG
TCAGGGAGGATTAGGAGGTCAGGGTGGAGGACAGGGAGGTCAAGGTGCTGCTGCAGCCGCTGCAGCC
GCTGCTGGAGGGGAGGTCAGGGAGGTGGTTATGGAGGTTTAGGAAGTCAAGCAGGAAGAGGGGGAT
TAGGTGGTCAAGGAGCTGCTGCTGCTGCTGCCGCAGCGGGTGGAGGAGGGCAAGGTGGAAGTCA
GGCAGGTAGAGGAGGGTTAGGTtcCgggTTGGGGGGTCAGGGTGCTGCTGCTGCTGCAGCCGCTGCTGC
GGGAGGTGGGGGTCAAGGGGGAGGATATGGAGGATTAGGGTCGCAGGCTGGAAGAGGAGGAGGAAG
CGGACGAGGAGGATTAGGAGGACAAGGAGCTGCTGCTGCTGCAGCCGCTGCTGCTGGAGGAGGCGGA
CAAGGTGGGTTAGGAGGTCAAGGTGCTGCGGCTGCTGCTGCTGCTGCTGGAGGAGGAGGACAAG
GCGGAGGATATGGGGGTTTAGGAAGTCAGGCAGGAAGAGGAGGAGGGGGAAGAGGAGGATTGGGGG
GACAAGGAGCTGCTGCTGCTGCAGCCGCTGCTGCTGGAGGAGGAGGTCAGGGAGGAGGATATGGTGG
ATTAGGAAGCCAAGCTGGAAGGGGAGGATTAGGAGGACAGGGTGCTGCAGCTGCTGCTGCGGCCGCG
GCTGGAGGGGGGGTCAGGGAGGTGGATATGGAGGATTAGGATCACAAGCTGGAAGAGGAGGATTA
GGAGGACAGGGAGCTGCTGCAGCTGCTGCCGCTGCTGCTGGAGGAGGAGGACAAGGTGGAGGATACG
GTGGGTTGGGGAGTCAAGCAGGTAGAGGAGGAGGTTATGGAGGATTGGGAAGTCAAGCTGGAAGAG
GGGGAGGTAGTGGTCGAGGAGGAGGAGGACAAGGTGCGGCTGCTGCGGCCGCGGCTGCTGCAGGTGG
AGGAGGTCAGGGAGGATTAGGAGGTCAGGGTGGAGGACAGGGAGGTCAAGGTGCTGCTGCAGCCGCT
GCAGCCGCTGCTGGAGGGGAGGTCAGGGAGGTGGTTATGGAGGTTTAGGAAGTCAAGCAGGAAGAG
GGGGATTAGGTGGTCAAGGAGCTGCTGCTGCTGCTGCCGCAGCGGGTGGAGGAGGGCAAGGTGG
AAGTCAGGCAGGTAGAGGAGGGTTAGGTtcCgggTTGGGGGGTCAGGGTGCTGCTGCTGCTGCAGCCGC
TGCTGCGGGAGGTGGGGGTCAAGGGGGAGGATATGGAGGATTAGGGTCGCAGGCTGGAAGAGGAGG

FIG. 22 - SEQ ID NO: 35 Continued

```
AGGAAGCGGACGAGGAGGATTAGGAGGACAAGGAGCTGCTGCTGCTGCAGCCGCTGCTGCTGGAGGA
GGCGGACAAGGTGGGTTAGGAGGTCAAGGTGCTGCGGCTGCTGCTGCTGCTGCTGCTGGAGGAGGAG
GACAAGGCGGAGGATATGGGGGTTTAGGAAGTCAGGCAGGAAGAGGAGGAGGGGGAAGAGGAGGAT
TGGGGGGACAAGGAGCTGCTGCTGCTGCAGCCGCTGCTGCTGGAGGAGGAGGTCAGGGAGGAGGATA
TGGTGGATTAGGAAGCCAAGCTGGAAGGGGAGGATTAGGAGGACAGGGTGCTGCAGCTGCTGCTGCG
GCCGCGGCTGGAGGGGGGGGTCAGGGAGGTGGATATGGAGGATTAGGATCACAAGCTGGAAGAGGA
GGATTAGGAGGACAGGGAGCTGCTGCAGCTGCTGCCGCTGCTGCTGGAGGAGGAGGACAAGGTGGAG
GATACGGTGGGTTGGGGAGTCAAGCAGGTAGAGGAGGAGGTTATGGAGGATTGGGAAGTCAAGCTGG
     AAGAGGGGGAGGTAGTGGTCGAGGAGGAGGAGGACAAGGTGCGGCTGCTGCGGCCGCGGCT
     GCTGCAGGTGGAGGAGGTCAGGGAGGATTAGGAGGTCAGGGTGGAGGACAGGGAGGTCAAG
     GTGCTGCTGCAGCCGCTGCAGCCGCTGCTGGAGGGGGAGGTCAGGGAGGTGGTTATGGAGGT
     TTAGGAAGTCAAGCAGGAAGAGGGGGATTAGGTGGTCAAGGAGCTGCTGCTGCTGCTGCTGC
     CGCAGCGGGTGGAGGAGGGCAAGGTGGAAGTCAGGCAGGTAGAGGAGGGTTAGGTccCgggAT
     GGTGAGCAAGGGCGAGGAGCTGTTCACCGGGGTGGTGCCCATCCTGGTCGAGCTGGACGGCG
     ACGTAAACGGCCACAAGTTCAGCGTGTCCGGCGAGGGCGAGGGCGATGCCACCTACGGCAAG
     CTGACCCTGAAGTTCATCTCCACCACCGGCAAGCTGCCCGTGCCCTGGCCCACCCTCGTGACC
     ACCCTCACCTACGGCGTGCAGGTCTTCAGCCGCTACCCCGACCACATGAAGCAGCACGACTTC
     TTCAAGTCCGCCATGCCCGAAGGCTACGTCCAGGAGCGCACCATCTCTTTCAAGGACGACGGC
     AACTACAAGACCCGCGCCGAGGTGAAGTTCGAGGGCGACACCCTGGTGAACCGCATCGAGCT
     GAAGGGCATCGACTTCAAGGAGGACGGCAACATCCTGGGGCACAAGCTGGAGTACAACTACA
     ACCCCCACAACGTCTATATCATGGCCGACAAGCAGAAGAACGGCATCAAGGTGAACTTCAAG
     ACCGGTCACAACATCGAGGACGGCAGCGTGCAGCTCGCCGACCACTACCAGCAGAACACCCC
     CATCGGCGACGGCCCCGTGCTGCTGCCCGACAACCACTACCTGAGCACCCAGTCCAAGCTGCT
     CAAAGACCCCAACGAGAAGCGCGATCACATGGTCCTGCTGGAGTTCGTGACCGCCGCCGGGA
     TCACTCTCGGCATGGACGAGCTGTACAAGGGTGTGTCATCTGCTTCATCTCGCAGTTACGACT
     ATTCTCGTCGTAACGTCCGCAAAAACTGTGGAATTCCTAGAAGACAACTAGTTGTTAAATTCA
     GAGCACTGCCTTGTGTGAATTGCTAATTTTTAATATAAAATAACCCTTGTTTCTTACTTCGTCC
     TGGATACATCTATGTTTTTTTTTCGTTAATAAATGAGAGCATTTAAGTTATTGTTTTTAATTAC
     TTTTTTTTAGAAAACAGATTTCGGATTTTTTGTATGCATTTTATTTGAATGTACTAATATAATCA
     ATTAATCAATGAATTCATTTATTTAAGGGATAACAATAATCCATGAATTCACATGCACATTTA
     AAACAAAACTAAATTACAATAGGTTCATATAAAAACAACAAGTATGCCTTCTCAACTAAGAA
     TACTATATTGTTTAAACCGTAAAAAAAGTCATATTTCTGTATATCAAAACACATCTAATATTAA
     AAAAACAGTCAGCAAGCACTTACAAGTGTGGGCTCGGACAGCAATTACCTGGTCTCAGGAGA
     CACTTGAAGAACGAGAAGCACGTCTCTCTGTCGATTGCGAGGCTCATGCACTATCGCTTGAGT
     CTGAGACCTTTACTGATAGGGAAATCCGTTTGAGCTCTCAGAGGGTTCGGACAGCAAAAGCTT
     GCCCGGTCTCAGGAGACATTAGAAGAACGGGAAGCATAACTCAATACCGATCGCGTTTCCATT
     GAGCCTATGCTTCGTGATAATAATAAATAAAGCCCAAGGTCAGACGCTAAAAGAAAGGAGAT
     AGGATCCAAGCTTGGCGTAATCATGGTCATAGCTGTTTCCTGTGTGAAATTGTTATCCGCTCAC
     AATTCCACACAACATACGAGCCGGAAGCATAAAGTGTAAAGCCTGGGGTGCCTAATGAGTGA
     GCTAACTCACATTAATTGCGTTGCGCTCACTGCCCGCTTTCCAGTCGGGAAACCTGTCGTGCCA
     GCTGCATTAATGAATCGGCCAACGCGCGGGGAGAGGCGGTTTGCGTATTGGGCGCT
```

METHODS, COMPOSITIONS AND SYSTEMS FOR PRODUCTION OF RECOMBINANT SPIDER SILK POLYPEPTIDES

PRIORITY CLAIM TO RELATED APPLICATIONS

The present application is a continuation of U.S. application Ser. No. 14/843,363, filed Sep. 2, 2015, which is a division of U.S. application Ser. No. 12/363,326, filed Jan. 30, 2009, now U.S. Pat. No. 9,131,671, which claims priority under 35 U.S.C. § 119(e) of Provisional Application No. 61/025,616, filed Feb. 1, 2008, and Provisional Application No. 61/037,937, filed Mar. 19, 2008. The entire contents of each of these applications are incorporated herein by reference.

FIELD OF THE INVENTION

The present invention relates to methods, compositions and systems for production of recombinant spider silk polypeptides.

BACKGROUND OF THE INVENTION

Spider silk is a natural fiber with exceptional properties. Dragline silks in particular possess tensile strength equal to, and a toughness that exceeds, KEVLAR™ (Gosline et al., Endeavour, 10, 37-43, (1986); Denny, M. W. J. Exp. Biol., 65, 483-506 (1976); and Lucas, F. Discovery, 25, 20-26 (1964)). As a silk fiber, spider silk has the texture and flexibility of silk produced by silkworms (e.g., Bombyx mori). Thus, spider silk can be processed, woven, and dyed in the same manner and using the same equipment used for the processing of silkworm silk. However, spider silk has much more strength and elasticity than silk derived from the silkworm, giving textiles derived from spider silk unique properties. Spider silk can be used as a direct replacement for KEVLAR™, Spectra™, and other high strength fibers giving stronger, lighter, and more flexible products.

Spider silk is composed of large proteins, made up of alternating beta sheets and amorphous domains (Lucase, F. et al, J. Text Inst., 46, T440-T452 (1985); Hepburn, H. R. et al. Insect BioChem., 9, 69-77 (1979); and Warwicker, J. O., J. Mol. Biol., 2, 350-362 (1960)). The beta sheet domains are believed to be responsible for the strength of silks. It has been suggested that similar to rubber, the elasticity of spider silk is entropy driven, and that the amorphous sections between the beta sheets are responsible for much of the elasticity (Gosline et al, Nature, 309, 551-552, (1984); Hepburn, H. R. et al, Insect Biochem., 9, 69-77 (1979)).

The formation of silk from the precursor dope solution is a complex biological, chemical, and physical process. This complex interaction has apparently been maximized in arthropods such as spiders and moths, but has yet to be replicated artificially by humans.

For example, the genes for several spider silks have been identified and cloned. Also, attempts have been made to design peptides that display similar biological and physiological characteristics to spider silk (i.e., "spider silk analogs). Expression of such native spider silk peptides and potential spider silk analog peptides in bacteria, insect cell lines, goats, and plants has been achieved. However, attempts to spin silk from the purified precursors have not met with success, in part because the resulting fiber(s) did not properly replicate the qualities of native spider silk.

Spiders are solitary, cannibalistic arthropods and as such, are not particularly well suited for use as bioreactors. Additionally, spiders only produce short segments of fiber in limited quantities. Silkworms, on the other hand, produce filaments exceeding 1000 meters in length. Additionally, silkworms produce large quantities of silk; the annual world production approaches 100 million kilograms. Bombyx mori silkworms have been used as a bioreactor to produce a number of proteins and peptides, but the expression systems have generally been found to be relatively unstable and of short duration. Also, the exact mechanisms for the synthesis, modification, internal transport, and spinning of the silk fiber in Bombyx mori are not clearly known. Until these mechanisms are elucidated, the use of the natural genetic, cellular, and organelle/organ systems are most likely to give large quantities of high quality silk fiber.

Production of transgenic silkworms by use of piggyBac transposons is described in U.S. Pat. No. 6,872,869, where a portion of a spider silk gene was fused with a portion of the light chain fibroin of Bombyx under the control of the promoter of the light chain fibroin. The in-frame fusion gene was linked to a reporter gene and then the construct was ligated in between two inverted terminal repeats of the piggyback transposon. The first plasmid having the fusion gene and insertion sequences was transfected with a second plasmid encoding the transposase into silkworm eggs. These insertions produced silk reported to be 30% spider silk mixed with normal Bombyx silk. As the silkworm heavy fibroin chain is approximately 340 kilodaltons (kD), and the fusion protein was about 30 kD, a 30% level of spider silk should in fact, correspond to a weight percent of about 5-15%. Thus, because the natural genes are still present and active, the silk produced using these systems includes a significant amount of the less desirous Bombyx silk. Similar results of 10% levels of spider silk in silkworms have been informally reported by another group (see e.g., Zhang et al, Mol Biol Rep. 2007 May 25; 17525867, and the Times (UK) 10 December, 2007).

Thus, there is a significant problem in producing high strength spider silk, or spider silk analogs, from silkworms. It would be beneficial to produce silkworms that can generate significant amounts of spider silk, or a spider silk analog, that exhibits the characteristics of spider silk. The present invention addresses this problem by using the Bombyx silkworm, which is well-suited as a bioreactor, to produce a silk that solely or primarily consists of spider silk, or a spider silk analog, with little or no contamination by the lower strength natural Bombyx silk.

SUMMARY OF THE INVENTION

Embodiments of the present invention comprise methods, compositions and systems for transforming a first organism to produce silk polypeptides, or silk polypeptide analogs, from a second organism. For example, in certain embodiments, the present invention comprises methods to generate silkworms such as Bombyx mori that produce spider silk, and/or analogs of spider silk.

Embodiments of the present invention also comprise recombinant DNA constructs that provide for the production of such silk. In certain embodiments, the spider silk polypeptide, or spider silk polypeptide analog, is encoded by a recombinant DNA comprising DNA encoding a spider silk polypeptide (or analog thereof) fused to 5' and 3' DNA sequences from the silkworm silk gene so as to allow the recombinant DNA to insert into the silkworm silk gene locus by homologous recombination. Thus in certain embodiments of the methods, compositions and systems of the present invention, the spider silk gene or analog thereof encoded by the recombinant DNA construct replaces a silkworm gene in genome of the silkworm.

For example, in one embodiment, the method comprises ligating a DNA sequence coding for at least a portion of a spider silk fibroin polypeptide, or an analog of a spider silk fibroin polypeptide, between at least a portion of the 5' and 3' ends of a silkworm fibroin gene to generate a fused gene having a sequence that encodes for a polypeptide comprising both spider silk fibroin and silkworm silk fibroin amino acid sequences (i.e., a spider silk/silkworm silk fusion gene). In some embodiments, both the 5' end of the silkworm fibroin gene and the 3' end of the silkworm fibroin gene are long enough to allow for homologous recombination to take place, such that when the genetically modified fibroin gene comprising a fused spider/silk silkworm gene is inserted into a silkworm, it is able to replace the native gene present in the silkworm.

The DNA sequence encoding a spider silk polypeptide or an analog thereof may be inserted into the genomic locus for the silkworm silk light fibroin gene, and/or the silkworm silk heavy fibroin gene. Or, a first DNA sequence encoding a spider silk fibroin, or analog thereof, may be inserted into the genomic locus for the silkworm silk light fibroin gene, and a second DNA encoding a second (i.e., distinct) spider silk fibroin, or analog thereof, may be inserted into the locus for the silkworm silk heavy fibroin gene the silkworm. Thus, in some cases, a plurality of spider silk polypeptides may be used, such that different silkworm transformants express different spider silk polypeptides, or analogs thereof. Embodiments of the present invention therefore can combine the best of both producers, the expression machinery of the *Bombyx* silkworm, and the silk produced by the spider.

Other embodiments and further details regarding various aspects of the present invention are set forth in the following description and claims. It is to be understood that the invention is not limited in its application to the details set forth in the following description and claims, but is capable of other embodiments and of being practiced or carried out in various ways.

BRIEF DESCRIPTION OF THE FIGURES

FIGS. 4A and 4B show a DNA sequence of a spider silk derived internal repeat segment in accordance with alternate embodiments of the present invention; FIG. 4A shows the DNA sequence (SEQ ID NO:1) and amino acid sequence (SEQ ID NO: 2) of a spider silk internal repeat comprising a spider silk analog polypeptide of the present invention; FIG. 4B illustrates the mutation made to an engineered construct of native spider silk DNA sequences (SEQ ID NO: 3) encoding an alternate spider silk polypeptide (SEQ ID NO: 4) so as to generate nucleotides 1 to 63 of SEQ ID NO: 1 encoding amino acids 1 to 21 of SEQ ID NO: 2.

FIG. 5 shows the DNA sequence (SEQ ID NO: 5) of a 5' end of a *Bombyx mori* silk gene that encodes the first exon (SEQ ID NO: 6) and a portion of the second exon (SEQ ID NO: 7) and that may be used to create a spider silk/silkworm silk fusion construct for insertion at a silkworm heavy chain fibroin locus in accordance with one embodiment of the present invention. The start and end of the intron is shown as bold font.

FIG. 6 shows the DNA sequence (SEQ ID NO: 8) of a 3' end of a *Bombyx mori* silk gene that encodes the C-terminal portion of the heavy chain (SEQ ID NO: 9) and that may be used to create a spider silk/silkworm silk fusion construct for insertion at a heavy chain fibroin locus in accordance with one embodiment of the present invention.

FIG. 7 shows the DNA sequence of an *Antheraea pernyi* (silkworm) 5' homologous segment (SEQ ID NO: 10) that encodes the first exon (SEQ ID NO: 11) and a portion of the second exon (SEQ ID NO: 12) and that may be used to create a spider silk/silkworm silk fusion construct for insertion at a heavy chain fibroin locus in accordance with one embodiment of the present invention. The start and end of the intron is shown as bold font.

FIG. 8 shows the DNA sequence of an *Antheraea pernyi* (silkworm) 3' homologous segment (SEQ ID NO: 13) that encodes the C-terminal portion of the heavy chain (SEQ ID NO: 14) and that may be used to create a spider silk/silkworm silk fusion construct for insertion at a heavy chain fibroin locus in accordance with one embodiment of the present invention.

FIG. 9 shows the DNA sequence of an *Antheraea yamamai* (silkworm) 5' homologous segment (SEQ ID NO: 15) that encodes the first exon (SEQ ID NO: 16) and a portion of the second exon (SEQ ID NO: 17) and that may be used to create a spider silk/silkworm silk fusion construct for insertion at a heavy chain fibroin locus in accordance with one embodiment of the present invention. The start and end of the intron is shown as bold font.

FIG. 10 shows the DNA sequence of an *Antheraea yamamai* (silkworm) 3' homologous segment (SEQ ID NO: 18) that encodes the C-terminal portion of the heavy chain (SEQ ID NO: 19) and that may be used to create a spider silk/silkworm silk fusion construct for insertion at a heavy chain fibroin locus in accordance with one embodiment of the present invention.

FIG. 11 shows the DNA sequence (SEQ ID NO: 20) encoding a polypeptide (SEQ ID NO: 21) for the 5' end of a *Bombyx mori* light fibroin silk gene and that may be used to create a spider silk/silkworm silk fusion construct for insertion at a light chain fibroin locus in accordance with one embodiment of the present invention.

FIG. 12 shows a DNA sequence (SEQ ID NO: 22) encoding a polypeptide (SEQ ID NO: 23) for the 3' end of a *Bombyx mori* light fibroin silk gene and that may be used to create a spider silk/silkworm silk fusion construct for insertion at a light chain fibroin locus in accordance with one embodiment of the present invention. The polyA recognition site is shown as bold font.

FIG. 15 shows a DNA sequence (SEQ ID NO: 24) that encodes a *Bombyx* fibroin intron GFP insert polypeptide (SEQ ID NO: 25) in accordance with one embodiment of the present invention.

FIG. 16 shows a DNA sequence (SEQ ID NO: 26) encoding 5' *Bombyx mori* homologous sequence with a knockout insertion and associated polypeptides SEQ ID NOS: 27, 28 and 29 in accordance with one embodiment of the present invention.

FIG. 17 shows the DNA sequences of a recombinant DNA construct (SEQ ID NO: 30) that encodes from 5' to 3'—a *Bombyx mori* silkworm 5' sequence (5'), one repeat of a spider silk analog (I), and a silkworm 3' sequence (3') in accordance with one embodiment of the present invention.

FIG. 18 shows the DNA sequences of a recombinant DNA construct (SEQ ID NO: 31) that encodes from 5' to 3'—a *Bombyx mori* silkworm 5' sequence (5'); one repeat of a spider silk analog (I); a green fluorescent protein (GFP) polypeptide (E) and a silkworm 3' sequence (3') in accordance with one embodiment of the present invention.

FIG. 19 shows the DNA sequences of a recombinant DNA construct (SEQ ID NO: 32) that encodes from 5' to 3'—a *Bombyx mori* silkworm 5' sequence (5'), two repeats of a spider silk analog ($I_2$), and a silkworm 3' sequence (3') in accordance with one embodiment of the present invention.

FIG. 20 shows the DNA sequences of a recombinant DNA construct (SEQ ID NO: 33) that encodes from 5' to 3'—a *Bombyx mori* silkworm 5' sequence (5'), two repeats of a spider silk analog ($I_2$), a green fluorescent protein (GFP) polypeptide (E), and a silkworm 3' sequence (3') in accordance with one embodiment of the present invention.

FIG. 21 shows the DNA sequences of a recombinant DNA construct (SEQ ID NO: 34) that encodes from 5' to 3'—a *Bombyx mori* silkworm 5' sequence (5'), three repeats of a spider silk analog (13), and a silkworm 3' sequence (3') in accordance with one embodiment of the present invention.

FIG. 22 shows the DNA sequences of a recombinant DNA construct (SEQ ID NO: 35) that encodes from 5' to 3'—a *Bombyx mori* silkworm 5' sequence (5'), three repeats of a spider silk analog (13), a green fluorescent protein (GFP) polypeptide (E), and a silkworm 3' sequence (3') in accordance with one embodiment of the present invention.

DETAILED DESCRIPTION OF THE INVENTION

Definitions

Figure 1:
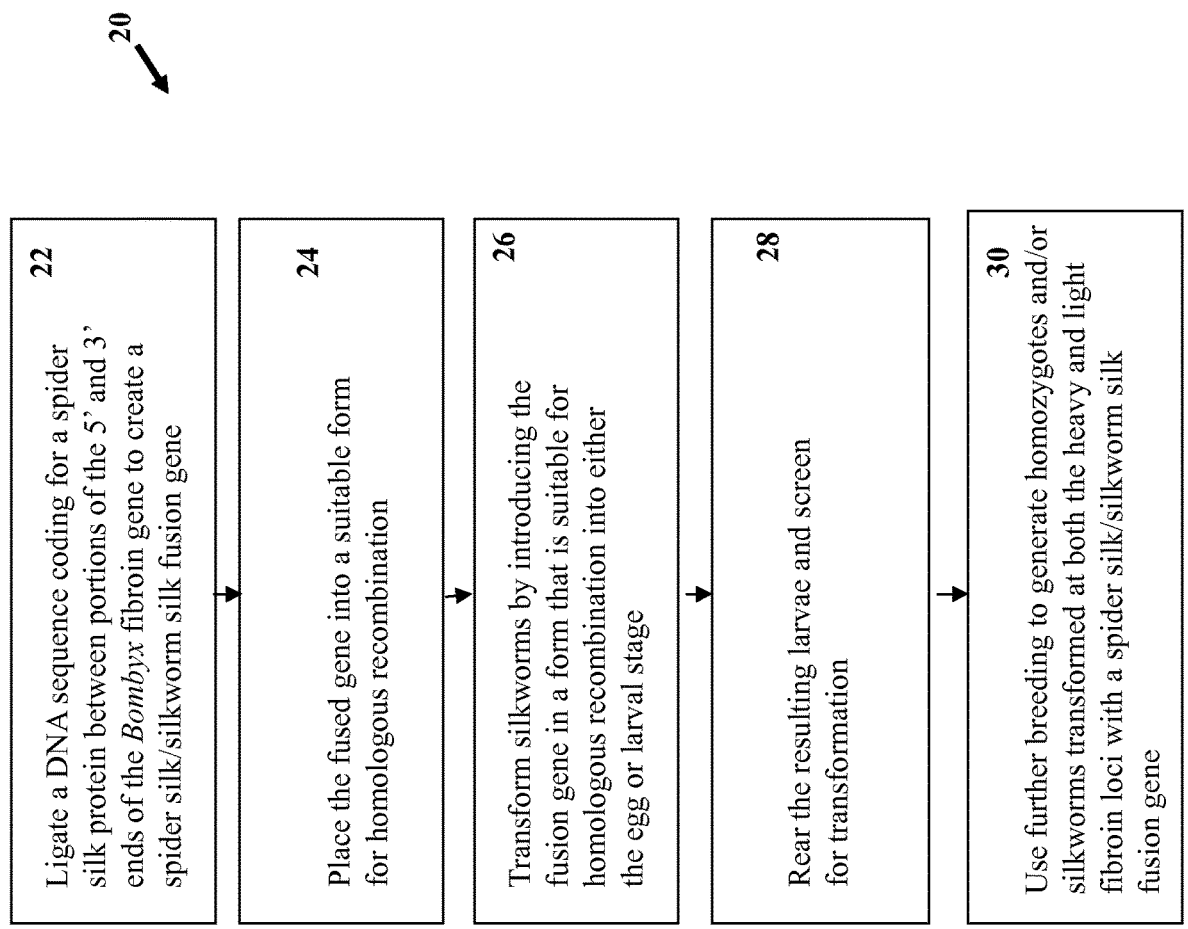
FIG. 1 shows a flow-chart of a method to transform silkworms with a recombinant DNA construct that comprises a silkworm silk/spider silk fusion gene by homologous recombination in accordance with one embodiment of the present invention.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more, e.g. 1 to 6.1, and ending with a maximum value of 10 or less, e.g., 5.5 to 10. Additionally, any reference referred to as being "incorporated herein" is to be understood as being incorporated in its entirety.

It is further noted that, as used in this specification, the singular forms "a," "an," and "the" include plural referents unless expressly and unequivocally limited to one referent. The term "or" is used interchangeably with the term "and/or" unless the context clearly indicates otherwise.

Unless defined otherwise, all technical and scientific terms used herein have the same meaning as commonly understood by one of ordinary skill in the art. Practitioners are particularly directed to *Current Protocols in Molecular Biology* (Ansubel) for definitions and terms of the art. Abbreviations for amino acid residues are the standard 3-letter and/or 1-letter codes used in the art to refer to one of the 20 common L-amino acids.

The term "recombinant" as used herein in relation to a polynucleotide intends a polynucleotide of semisynthetic, or synthetic origin, or encoded by cDNA or genomic DNA ("gDNA") such that it is not entirely associated with all or a portion of a polynucleotide with which it is associated in nature.

As used herein, the term "polypeptide" refers to a polymer of amino acids and does not refer to a specific length of the product. Thus, peptides, oligopeptides, and proteins are included within the definition of polypeptide. This term also does not exclude post-expression modifications of the polypeptide, for example, glycosylations, acetylations, phosphorylations and the like. Included within the definition are, for example, polypeptides containing one or more analogs of an amino acid (including, for example, unnatural amino acids), polypeptides with substituted linkages, as well as other modifications known in the art, both naturally occurring and non-naturally occurring. As is known in the art, "proteins", "peptides," "polypeptides" and "oligopeptides" are chains of amino acids (typically L-amino acids) whose alpha carbons are linked through peptide bonds formed by a condensation reaction between the carboxyl group of the alpha carbon of one amino acid and the amino group of the alpha carbon of another amino acid. Typically, the amino acids making up a protein are numbered in order, starting at the amino terminal residue and increasing in the direction toward the carboxy terminal residue of the protein.

As used herein, a polypeptide or protein "domain" comprises a region along a polypeptide or protein that comprises an independent unit. Domains may be defined in terms of structure, sequence and/or biological activity. In one embodiment, a polypeptide domain may comprise a region of a protein that folds in a manner that is substantially independent from the rest of the protein. Domains may be identified using domain databases such as, but not limited to PFAM, PRODOM, PROSITE, BLOCKS, PRINTS, SBASE, ISREC PROFILES, SAMRT, and PROCLASS.

A "nucleic acid" is a polynucleotide such as deoxyribonucleic acid (DNA) or ribonucleic acid (RNA). The term is used to include single-stranded nucleic acids, double-stranded nucleic acids, and RNA and DNA made from nucleotide or nucleoside analogues. The term "polynucleotide" as used herein refers to a DNA molecule, a RNA molecule or its complementary strand thereof. A polynucleotide molecule can be single or double stranded.

DNA molecules may be identified by their nucleic acid sequences, which are generally presented in the 5' to 3' direction, wherein 5' and 3' indicate the linkages formed between the 5'-phosphate group of one nucleotide and the 3'-hydroxyl group of the next. For a sequence presented in the 5' to 3' direction, its complement is the DNA strand which hybridizes to that sequence according to the Watson-Crick base pairing model. Thus, the sequence of the complement is defined by the sequence of the original strand, such that adenine base-pairs with thymine, and cytosine base-pairs with guanine.

As used herein, a small inhibitory RNA is a double-stranded RNA of about 20-30 nucleotides that associates with proteins to form an RNAi-induced silencing complex (RISC) that may direct the siRNA to the target RNA sequence. The ds siRNA may then unwind, leaving the antisense strand to signal degradation of the mRNA sequence by endonucleases and exonucleases. In order to obtain lasting therapeutic effects, the RNAi sequence may be expressed long term, preferably under a constitutive promoter. To obtain dsRNA from a vector, it may be expressed as a short hairpin RNA (shRNA), in which there is a sense strand, a hairpin loop region and an antisense strand (Miyagishi et al., *J Gene Med* 6:715-723, 2004).

As used herein, the term "upstream" refers to a residue that is N-terminal to a second residue where the molecule is a protein, or 5' to a second residue where the molecule is a nucleic acid. Also as used herein, the term "downstream" refers to a residue that is C-terminal to a second residue where the molecule is a protein, or 3' to a second residue where the molecule is a nucleic acid. Also, the terms "portion" and "fragment" are used interchangeably to refer to parts of a polypeptide, nucleic acid, or other molecular construct.

The term "vector" refers to a nucleic acid molecule that may be used to transport a second nucleic acid molecule into a cell. In one embodiment, the vector allows for replication of DNA sequences inserted into the vector. The vector may comprise a promoter to enhance and/or maintain expression of the nucleic acid molecule in at least some host cells. Vectors may replicate autonomously (extrachromasomally) or may be integrated into a host cell chromosome. In one embodiment, the vector may comprise an expression vector capable of producing a protein or a nucleic acid derived from at least part of a nucleic acid sequence inserted into the vector.

As is known in the art, conditions for hybridizing nucleic acid sequences to each other can be described as ranging from low to high stringency. Generally, highly stringent hybridization conditions refer to washing hybrids in low salt buffer at high temperatures. Hybridization may be to filter bound DNA using hybridization solutions standard in the art such as 0.5M $NaHPO_4$, 7% sodium dodecyl sulfate (SDS), at 65° C., and washing in 0.25 M $NaHPO_4$, 3.5% SDS followed by washing 0.1×SSC/0.1% SDS at a temperature ranging from room temperature to 68° C. depending on the length of the probe (see e.g. Ausubel, F. M. et al., *Short Protocols in Molecular Biology*, 4th Ed., Chapter 2, John Wiley & Sons, N.Y.). For example, a high stringency wash comprises washing in 6×SSC/0.05% sodium pyrophosphate at 37° C. for a 14 base oligonucleotide probe, or at 48° C. for a 17 base oligonucleotide probe, or at 55° C. for a 20 base oligonucleotide probe, or at 60° C. for a 25 base oligonucleotide probe, or at 65° C. for a nucleotide probe about 250 nucleotides in length. Nucleic acid probes may be labeled with radionucleotides by end-labeling with, for example, [gamma-$^{32}$P]ATP, or incorporation of radiolabeled nucleotides such as [alpha-$^{32}$P]dCTP by random primer labeling. Alternatively, probes may be labeled by incorporation of biotinylated or fluorescein labeled nucleotides, and the probe detected using Streptavidin or anti-fluorescein antibodies.

The terms "identity" or "percent identical" refer to sequence identity between two amino acid sequences or between two nucleic acid sequences. Percent identity can be determined by aligning two sequences and refers to the number of identical residues (i.e., amino acid or nucleotide) at positions shared by the compared sequences. Sequence alignment and comparison may be conducted using the algorithms standard in the art (e.g. Smith and Waterman, 1981, *Adv. Appl. Math.* 2:482; Needleman and Wunsch, 1970, *J. Mol. Biol.* 48:443; Pearson and Lipman, 1988, *Proc. Natl. Acad. Sci., USA*, 85:2444) or by computerized versions of these algorithms (Wisconsin Genetics Software Package Release 7.0, Genetics Computer Group, 575 Science Drive, Madison, Wis.) publicly available as BLAST and FASTA. Also, ENTREZ, available through the National Institutes of Health, Bethesda Md., may be used for sequence comparison. In one embodiment, the percent identity of two sequences may be determined using GCG with a gap weight of 1, such that each amino acid gap is weighted as if it were a single amino acid mismatch between the two sequences. For example, the term at least 90% identical thereto includes sequences that range from 90 to 100% identity to the indicated sequences and includes all ranges in between. Thus, the term at least 90% identical thereto includes sequences that are 91, 91.5, 92, 92.5, 93, 93.5, 94, 94.5, 95, 95.5, 96, 96.5, 97, 97.5, 98, 98.5, 99, 99.5 percent identical to the indicated sequence. Similarly the term "at least 70% identical includes sequences that range from 70 to 100% identical, with all ranges in between. The determination of percent identity is determined using the algorithms described here.

As used herein, "homology" refers to the degree of similarity between two proteins and or nucleic acid sequences. Homologous proteins are those that are similar in sequence and function. Typically, the sequence identity between two homologous sequences will be at least 50%. Also, homologous proteins will have conservative substitutions for non-identical sequences. In alternate embodiments, the sequence identity between two homologous sequences will be at least 60%; or at least 75%; or at least 80%; or at least 90%, or at least 95%, or at least 96%, or at least 97%, or at least 98%, or at least 99%. Also, as used herein, the term "homologue" means a polypeptide having a degree of homology with the wild-type amino acid sequence. Homology comparisons can be conducted by eye, or more usually, with the aid of readily available sequence comparison programs. These commercially available computer programs can calculate percent homology between two or more sequences (e.g. Wilbur, W. J. and Lipman, D. J., 1983, *Proc. Natl. Acad. Sci. USA*, 80:726-730).

As used herein, the term "silkworm" refers to a larvae of any member of the Saturniids, more typically the genus *Bombyx*, especially if used without modifier (e.g. *Antheraea* silkworm). Less formally, silkworm may also refer to adults of Lepidoptera most typically the Saturniids, and especially the genera *Bombyx* and *Antheraea*.

As used herein, the term "spider" refers to air-breathing chelicerate arthropods that have two body segments, eight legs, no chewing parts and that make silk. Spiders of the present invention are from the Arachnida class, the Araneae order, and include for example Nephilidae (especially *Nephila* species, like *clavipes*), and Araneidae such as *Araneus* and *Argiopes*, among many other suitable species.

As used herein, "silk" includes proteins and peptides produced by arthropods, typically by spiders, or by Lepidoptera, that display properties typical of native silk peptides. Lepidopteran silk generally is made up of a heavy fibroin polypeptide and a light chain fibroin peptide that are joined by a disulfide bond. In spiders there are two or more peptides not joined by a disulfide bond. Thus, silk includes proteinaceous filaments produced by insects or spiders, typically (but not necessarily) of two or more polypeptides. These may be chemically linked, and are typically very long polypeptides.

A native silkworm silk polypeptide is one several proteins or polypeptides, or fragments thereof, produced by silkworm silk glands. As used herein, a native silkworm silk polypeptide is a polypeptide having at least 99% identity to a native silkworm silk heavy and/or light fibroin polypeptide. For example, silkworm silk comprises and may consist of the silk polypeptides produced by members of the genus *Bombyx*.

A native spider silk polypeptide is one of the proteins or polypeptides, or fragments thereof, produced by spider silk glands. As used herein, a native spider silk polypeptide is a polypeptide having at least 99% identity, or in some cases 100% identity, to a native spider silk heavy and/or light fibroin polypeptide. Spider silk is a protein based fiber. It is known for its high strength and elasticity. Each species of spider produces several kinds of silk, and the silks vary in sequence between the species. Each of these types of silk is encompassed by the present invention. Some of the varieties of silk produced by spiders for which either the natural peptides, or peptide analogs are encompassed by the methods, compositions and systems of the invention are: (a) major ampullate silk—a tough, strong, and elastic silk that is used for the webs and spokes of webs as well as draglines; (b) flagelliform silk—a very stretchy, sticky silk that is used to capture insects; (c) tubiliform silk—a very stiff spider silk that is used to produce egg cases; (d) aciniform silk—a tough and elastic silk that is used to wrap captured prey; and (e) minor-ampullate silk—a silk that is somewhat less tough and elastic compared to dragline silk.

As used herein, an "analog of a spider silk" or an "analog of a spider silk polypeptide" comprises or consists of a polypeptide having amino acid domains, such as beta-sheets and alpha helices that are derived from, or homologous to, those domains as found in spider silk proteins. In certain embodiments, a spider silk analog polypeptide is comprised of peptide domains that are at least 50%, 60%, 70%, 80%, 90%, 95%, 96%, 97%, or 98% identical to native spider silk. For example, the spider silk analog may comprise, or consist of, a sequence made up of a plurality of alternating spider silk beta-sheet sequences and alpha helices as described herein. In certain embodiments, the spider silk polypeptide may comprise from 4 to 1000, or 4 to 800, or 4 to 500, or 5 to 200, or 5 to 100, or 5 to 50, or 6 to 40, or 6 to 30, or 6 to 15 or 6 to 12, or about 9 beta-sheet domains. The beta sheet regions may comprise a plurality of consecutive alanine residues, or a plurality of other amino acids that can form hydrogen bonds and that are typically arranged in consecutive order in beta sheet regions, and may range from about or 3 to 50, or 4 to 40, or 4 to 30, or 4 to 15, or 4 to 12, or 6 to 10, or about 9 consecutive hydrogen bonding amino acids (e.g., (Ala-Ala-Ala-Ala-Ala-Ala-Ala-Ala-Ala)). In certain embodiments, the spider silk polypeptide may comprise from 4 to 1000, or 4 to 800, or 4 to 500, or 5 to 200, or 5 to 100, or 5 to 50, or 6 to 40, or 6 to 30, or 6 to 15 or 6 to 12, or about 9 or 10 alpha helix domains. The alpha helix domains may comprise a plurality of glycine residues interspersed with other amino acids (e.g., Q, Y, L, S. R, A or P) typically found in alpha helix domains, and may range from about 4 to 200, or 5 to 100, 5 to 50, or 6 to 45, or 12 to 40, or 12 to 45 amino acids in length.

In certain embodiments, the spider silk peptide domains are derived from, i.e., are at least 50%, 60%, 70%, 80%, 90%, 95%, 96%, 97%, or 98% identical to spider silk fibroin sequences. Also, a spider silk analog may comprise a single polypeptide having a mixture of different spider silk polypeptide domains, or analogs thereof, either from the same or different species. Example domains that may be used to generate a spider silk polypeptide of SEQ ID NO: 2 include the following peptides: LGGQGAAAAAAAAAGGGG-QGG (SEQ ID NO 36), GYGGLGSQAGRGG (SEQ ID NO: 37), LGGQGGGQ (SEQ ID NO: 38), GSGRGG (SEQ ID NO: 39), LGGQGAAAAAAAAAGAGGQGG (SEQ ID NO 40), and LGGQGAGQ (SEQ ID NO: 41).

The analogs may further include peptides having one or more peptide mimetics, also known as peptoids, that possess the bioactivity of the protein. Included within the definition are also polypeptides containing one or more amino acid analogs (including, for example, unnatural amino acids, etc.), polypeptides with substituted linkages, as well as other modifications known in the art, both naturally occurring and non-naturally occurring. The term polypeptide also does not exclude post-expression modifications of the polypeptide, for example, glycosylations, acetylations, phosphorylations and the like.

Spider silk analogs may be generated using molecular techniques. For example, PCR mutagenesis of DNA encoding the spider silk peptide analogs can be used. Or RNA based mutagenesis techniques may be used. An example of a PCR technique for making mutations in DNA is described in WO 92/22653. Another method for making analogs, muteins, and derivatives, is cassette mutagenesis based on the technique described by Wells, Gene, (1985) 34:315. Or, chemical modification of the peptides may be performed.

Thus, the analogs of spider silk polypeptides may contain amino acid substitutions, deletions, or insertions. The amino acid substitutions can be conservative amino acid substitutions or substitutions to eliminate non-essential amino acid residues such as to alter a glycosylation site, a phosphorylation site, an acetylation site, or to minimize misfolding by substitution or deletion of one or more cysteine residues that are not necessary for function.

As used herein, the term "conserved residues" refers to amino acids that are the same among a plurality of proteins having the same structure and/or function. A region of conserved residues may be important for protein structure or function. Thus, contiguous conserved residues as identified in a three-dimensional protein may be important for protein structure or function. To find conserved residues, or conserved regions of 3-D structure, a comparison of sequences for the same or similar proteins from different species, or of individuals of the same species, may be made. Conservative amino acid substitutions are generally those that preserve the general charge, hydrophobicity/hydrophilicity and/or steric bulk of the amino acid substituted, for example, substitutions between the members of the following groups are conservative substitutions: Gly/Ala, Val/Ile/Leu, Asp/Glu, Lys/Arg, Asn/Gln, Ser/Cys/Thr and Phe/Trp/Tyr.

As used herein, a homozygous transformant includes silkworms that have both native silkworm light fibroin or heavy fibroin loci replaced by a DNA that encodes for a spider silk gene or analog thereof, and include transformants in which the spider silk sequences at each of the loci are not the same, but encode distinct spider silk polypeptides or analogs thereof.

An "expression vector" is a polynucleotide that is operable in a desired host cell and capable of causing the expression of a gene of interest in that host cell.

A "regulatory sequence" refers to a polynucleotide sequence that is necessary for regulation of expression of a coding sequence to which the polynucleotide sequence is operably linked. The nature of such regulatory sequences may differ depending upon the host organism. Such regulatory sequences generally include, for example, a promoter, and/or a transcription termination sequence. The term "regulatory sequence" may also include additional components the presence of which are advantageous, for example, a secretory leader sequence for secretion of the polypeptide attached thereto.

"Operably linked" refers to a juxtaposition wherein the components so described are in a relationship permitting them to function in their intended manner. A regulatory sequence is "operably linked" to a coding sequence when it is joined in such a way that expression of the coding sequence is achieved under conditions compatible with the regulatory sequence. Operably linked sequences may have additional nucleotides (or amino acids in a peptide) positioned between the two components of interest.

As used herein, "terminators" are regulatory sequences, such as polyadenylation and transcription termination sequences, located 3' or downstream of the stop codon of the coding sequences.

As used herein, "recombinant host cells," "host cells," "cells," "cell cultures," and other such terms denote, for example silkworm eggs or cells derived therefrom that have been used as recipients for introduction of recombinant vector or other transfer DNA, and include the progeny of the cell that has been transformed.

"Transformation" or "transfection," as used herein, refers to the transfer of an exogenous polynucleotide into a host cell, irrespective of the method used for the transfer, which can be, for example, by infection, direct uptake, transduction, F-mating, injection, microinjection or electroporation. The exogenous polynucleotide may be maintained as a non-integrated vector, for example, in some cases, a plasmid, or alternatively, may be integrated into the host genome.

"Purified" and "isolated" in reference to a polypeptide or a nucleotide sequence means that the indicated molecule is present in substantial absence of other biological macromolecules of the same species or type. In alternate embodiments, the term "purified" as used herein refers to at least 75% by weight; or at least 85% by weight, or at least 95% by weight or at least 98% by weight, of biological macromolecules of the same type.

An adjuvant is a chemical or biological agent that modifies or enhances the effect of other agents (e.g., drugs, vaccines, plasmids) while having few if any direct effects when given by themselves. Roughly analogous to chemical catalysts, they may have the effect of enhancing the entry into a host cell of DNA segments or plasmids, or enhancing the recombination of such DNA with the host cell DNA.

Methods, Compositions and Systems for Production of Recombinant Silk

Embodiments of the present invention comprise methods, compositions and systems for producing high-quality silk. The present invention may be embodied in a variety of ways.

In certain embodiments, the present invention comprises methods, compositions and systems for expressing a recombinant silk polypeptide by inserting DNA encoding the recombinant silk into the genomic locus for a native silk polypeptide in a silk-producing organism. In certain embodiments, the present invention comprises methods, compositions, and/or systems to express in a first organism, a silk polypeptide, or analog thereof, from a second organism. In certain embodiments, a recombinant DNA construct comprising sequences that encode for a silk polypeptide, or analog thereof, from the second organism is inserted into the genome of the first organism such that the sequences encoding for the silk polypeptide, or an analog thereof, from the second organism are expressed in the first organism. In certain embodiments, the DNA construct comprising sequences that encode for a silk polypeptide, or an analog thereof, from the second organism is inserted into the genome of the first organism such that the sequences encoding for the silk polypeptide, or analog thereof, from the second organism replace genomic sequences for native silk in the first organism, such that the silk polypeptide from the second organism replaces a silk polypeptide made by the first organism.

In one embodiment, the first organism is a silkworm. For example, *Bombyx mori* silkworms may be used as the first organism. Or, other types of silk-producing organisms may be used, such as *Antheraea pernyi*, *assamensis*, or *yamami; Samia cynthia*; or *Gonometa* species, such as *postica* or *rufobrunnea*; among other suitable species.

In certain embodiments, the silk polypeptide, or analog thereof, is derived from spider silk. Or silk from other organisms such as Trichoptera may be used. Thus, certain embodiments of the present invention comprise replacing silkworm silk genomic sequences with sequences that encode for a spider silk polypeptide or analog thereof. For example, in certain embodiments, the silk polypeptide is spider dragline silk or an analog thereof. Or, other types of spider silk, such as: (a) major ampullate silk; (b) flagelliform silk; (c) tubiliform silk; (d) aciniform silk; or (e) minor-ampullate silk, or analogs thereof, may be produced. It is understood, however, that in certain embodiments, organisms other than silkworm may be used as silk bioreactors, and peptides derived from organisms other than spiders may be used in the methods, systems and compositions of the present invention.

The spider silk polypeptide used in the methods, compositions and systems of the present invention may be a native spider silk polypeptide, or may be an analog of a native spider silk polypeptide. In certain embodiments, an analog of a spider silk polypeptide comprises a peptide having amino acid domains, such as beta sheets and alpha helices that are derived from, or homologous to, those domains as found in spider silk proteins. In certain embodiments, the spider silk polypeptide domains are derived from spider silk fibroin sequences. Or a mixture of spider silk polypeptide domains may be used.

For example, in certain embodiments, the present invention provides methods, compositions and systems for expression of native spider silk (e.g., such as dragline silk), or analogs of spider silk in silkworms (e.g., *Bombyx mori*). In certain embodiments, the present invention reduces or eliminates the dilution of spider silk by natural *Bombyx* silk in the transformed *Bombyx mori*.

Thus, embodiments of the present invention may comprise methods to make a silkworm that is capable of producing a silk comprising a spider silk polypeptide, or an analog of a spider silk polypeptide. In certain embodiments, the spider silk polypeptide is encoded by a recombinant DNA.

For example, in one embodiment, the invention may comprise a method comprising inserting a DNA sequence coding for at least a portion of a spider silk fibroin polypeptide, or an analog of a spider silk fibroin polypeptide, into the genome of a silkworm. In certain embodiments, the transformed silkworm expresses a polypeptide comprising a spider silk fibroin, or an analog thereof, and does not express substantial amounts of the light chain and/or heavy chain native silkworm silk fibroin polypeptide.

In certain embodiments, the native silkworm fibroin genes are genetically modified such that at least one native silkworm fibroin peptide that is normally used to form silkworm silk is not expressed to a level that is sufficient to generate silkworm silk. The genetic modification of the silkworm fibroin gene or genes may comprise the step of eliminating expression of at least one native silkworm fibroin gene. Genetic techniques that are known in the art for knocking out gene expression may be used to eliminate expression of the native (i.e., wildtype) silkworm gene or genes.

For example, homologous recombination may be used to knock-out the native silkworm gene and/or to replace the silkworm gene with a recombinant DNA encoding a spider silk polypeptide or analog thereof. Embodiments of methods and constructs that may be used to generate silkworm knockouts are provided in the Examples herein. In this way, the spider silk polypeptide or analog thereof, will be expressed, but the native silkworm silk polypeptide is not expressed in substantial amounts. In certain embodiments, a plasmid vector is used to insert a recombinant DNA construct encoding a spider silk polypeptide, or analog thereof, into the silkworm genome. For example, a baculovirus vector, or other vectors known in the art, may be used to insert the spider silk sequences into the silkworm genome.

In some embodiments, the DNA encoding for a spider silk peptide, or analog thereof, may be inserted anywhere in the silkworm genome such that expression of the spider silk polypeptide occurs. In this embodiment, however, there may be production of both the native silkworm polypeptide and the spider silk polypeptide or analog thereof. Thus, to prevent the native silkworm silk polypeptide (e.g., heavy or light silkworm fibroin) from competing with the recombinant spider silk polypeptide, this embodiment may include the step of knocking out expression of the native silkworm gene as discussed herein. In that way, the spider silk polypeptide, or analog thereof is preferentially expressed.

In other embodiments, site-specific recombination is used such that the DNA encoding a spider silk polypeptide or analog thereof is inserted into the silkworm silk genomic locus so as to replace the gene encoding either the light or heavy chain silkworm fibroin (e.g., a spider silk fibroin replacing a silkworm heavy fibroin). In some embodiments, the gene introduced into the silkworm is a fusion gene that encodes a polypeptide comprising spider silk and silkworm silk sequences.

Thus, in certain embodiments, the methods of the present invention may be used to introduce spider silk sequences, or analogs thereof, into silkworms, or other natural producers of silk. In one embodiment, the methods and/or compositions are used to replace a native silk gene (e.g., heavy or light fibroin) with a recombinant gene that encodes for the desired silk analog polypeptide.

For example, in one embodiment, the method may comprise a method to make a silkworm that is capable of producing a silk comprising a spider silk polypeptide, or an analog of a spider silk polypeptide, where the method comprises ligating a DNA sequence coding for at least a portion of a spider silk fibroin polypeptide, or an analog of a spider silk fibroin polypeptide, between at least a portion of the 5' and 3' ends of a silkworm fibroin gene to generate a fusion gene construct (i.e., a fused gene) having a sequence that encodes for a polypeptide comprising both spider silk fibroin and silkworm silk fibroin amino acid sequences (i.e., a spider silk/silkworm silk gene). In certain embodiments, the 5' and 3' ends of a silkworm fibroin gene are long enough such that when the recombinant DNA is inserted into the nucleus of a silkworm, site-specific homologous recombination can occur such that the fusion gene replaces the native silk worm gene.

Thus, in certain embodiments, the present invention comprises a method to make a silkworm that is capable of producing a silk comprising a spider silk polypeptide, or analog thereof, comprising the steps of ligating a DNA sequence coding for at least a portion of a spider silk fibroin polypeptide or an analog thereof, between at least a portion of the 5' and 3' ends of a silkworm fibroin gene to generate a fusion gene construct having a sequence that encodes for a polypeptide comprising both spider silk fibroin and silkworm silk fibroin amino acid sequences, wherein the 5' and 3' ends of a silkworm fibroin gene are long enough to allow for site-specific homologous recombination such that when the fusion gene is inserted into a silkworm, it is able to replace the native gene present in the silkworm.

The method may further comprise transforming a first population of silkworms with a fusion gene construct encoding a spider silk fibroin gene, or analog thereof, and transforming a second population of silkworms with a fusion gene construct encoding a second (i.e., different) spider silk fibroin gene. The DNA sequence encoding a spider silk polypeptide or an analog thereof may be inserted into the genomic locus for the silkworm silk light fibroin gene, and/or the silkworm silk heavy fibroin gene. Or, a first DNA sequence encoding a spider silk fibroin, or analog thereof, may be inserted into the genomic locus for the silkworm silk light fibroin gene, and a second DNA encoding a second (i.e., distinct) spider silk fibroin, or analog thereof, may be inserted into the locus for the silkworm silk heavy fibroin gene. Thus, in some cases, a plurality of spider silk polypeptides may be used, such that different silkworm transformants express different spider silk polypeptides, or analogs thereof.

The method may comprise breeding the recombinant silkworms to generate silkworms that are homozygous at a fibroin loci for the fused gene construct. In alternate embodiments, the methods may thus comprise breeding the recombinant silkworms to generate silkworms that are either homozygous at a single silkworm loci and/or homozygous at two or more silkworm loci and/or that contain a spider silk/silkworm silk fusion construct at multiple loci as described herein. In certain embodiments at least one of light fibroin loci and one heavy fibroin chain in a recipient silkworm are replaced by a fusion gene construct encoding a spider silk fibroin polypeptide or an analog of a spider silk fibroin polypeptide. For example in certain embodiments, a silkworm having a first DNA sequence encoding a spider silk fibroin, or analog thereof, inserted into the genomic locus for the silkworm silk light fibroin gene, can be bred with a second silkworm having the same or a second DNA encoding a second (i.e., distinct) spider silk fibroin, or analog thereof, inserted into the locus for the silkworm silk heavy fibroin gene the silkworm so as to generate silkworms that express spider silk polypeptides, or analogs thereof, at both the light and heavy chain loci in a recipient silkworm.

In other embodiments, the present invention comprises compositions comprising a DNA sequence encoding a recombinant spider silk fibroin gene or a portion of a recombinant spider silk fibroin gene that encodes for an analog of a spider silk polypeptide.

For example, in one embodiment, the present invention comprises an isolated and/or recombinant DNA molecule having a nucleic acid sequence encoding an analog of a spider silk polypeptide. In one embodiment, the recombinant construct encodes both spider silk fibroin and silkworm silk fibroin amino acid sequences. In this embodiment, the recombinant construct may comprise a fusion gene. For example in one embodiment, the present invention comprises a composition comprising a DNA sequence encoding both spider silk fibroin and silkworm silk fibroin amino acid sequences, the composition comprising a recombinant DNA construct coding for at least a portion of a spider silk fibroin polypeptide, or an analog of a spider silk fibroin polypeptide, or a biological equivalent thereof, positioned between at least a portion of the 5' and 3' ends of a silkworm fibroin gene to generate a fusion gene construct having a sequence that encodes for a polypeptide comprising both spider silk fibroin and silkworm silk fibroin amino acid sequences.

The constructs of the present invention may allow for a native silkworm gene for either light or heavy chain fibroin to be replaced by a construct encoding the spider silk fibroin polypeptide or analog thereof. For example, the present invention may comprise a DNA molecule encoding for both spider silk fibroin and silkworm silk fibroin sequences. In certain embodiments, the recombinant DNA construct encodes for at least a portion of a spider silk fibroin polypeptide or an analog thereof, positioned between at least a portion of the 5' and 3' ends of a silkworm fibroin gene to generate a fusion gene construct having a sequence that encodes for a polypeptide comprising both spider silk fibroin and silkworm silk fibroin, wherein the 5' and 3' ends of a silkworm fibroin gene are long enough to allow for site-specific homologous recombination to occur, such that when the DNA construct is inserted into the nucleus of a silkworm, it is able to replace the native gene present in the silkworm.

In other embodiments, the present invention comprises systems, such as a silkworm or a silkworm egg or larvae, that expresses or encodes a spider silk polypeptide sequences or an analog thereof.

In one embodiment, the silkworms or silkworm eggs or larvae, may comprise a recombinant DNA construct comprising at least a portion of a spider silk fibroin polypeptide, or an analog of a spider silk fibroin polypeptide, or a biological equivalent thereof, operably linked (e.g., positioned between) at least a portion of the 5' and 3' ends of a silkworm fibroin gene to generate a fusion gene construct having a sequence that encodes for a polypeptide comprising both spider silk fibroin and silkworm silk fibroin amino acid sequences. In certain embodiments, the silkworm 5' and 3' sequences are directly linked to the sequences encoding a spider silk polypeptide or analog thereof. In certain embodiments, the transformed silkworm is generated using a recombinant DNA construct encoding for at least a portion of a spider silk fibroin polypeptide or an analog thereof, positioned between at least a portion of the 5' and 3' ends of a silkworm fibroin gene to generate a fused gene having a sequence that encodes for a polypeptide comprising both spider silk fibroin and silkworm silk fibroin, wherein the 5' and 3' ends of a silkworm fibroin gene are long enough to allow for site-specific homologous recombination to occur when the DNA construct is inserted into the nucleus of a silkworm.

The spider silk polypeptide, or analog thereof, used in the methods, compositions and systems of the present invention may comprise or consist of a polypeptide having amino acid domains, such as beta-sheets and alpha helices that are derived from, or homologous to, those domains as found in spider silk proteins. In certain embodiments, a spider silk analog polypeptide is comprised of peptide domains that are at least 50%, 60%, 70%, 80%, 90%, 95%, 96%, 97%, or 98% identical to native spider silk.

For example, the spider silk polypeptide, or analog thereof, may comprise, or consist of, a plurality of alternating beta-sheet sequences and alpha helices that are derived from spider silk sequences as described herein. In some embodiments, the spider silk analog polypeptide comprises a plurality of such domains, wherein each domain comprises a plurality of alternating beta sheet domains and alpha helix domains. In an embodiment, the domains comprising a plurality of alternating beta sheet domains and alpha helix domains comprises a unit that may be designated as a spider silk analog internal repeat (I).

For example, in certain embodiments, the spider silk polypeptide or analog thereof may comprise a single spider silk internal repeat domain (I). Or, the spider silk polypeptide or analog thereof may comprise a plurality of the same or different single spider silk internal repeat domains (e.g., IA, IB, IC, ID and the like) linked end to end in various arrangements as described in more detail herein. For example, the various internal repeat regions may vary from each other in having different beta sheet regions (i.e., domains) and/or different alpha helix domains and/or different numbers of each of these domains.

In certain embodiments, the spider silk polypeptide, or a spider silk polypeptide internal repeat (I), may comprise from 4 to 1000, or 4 to 800, or 4 to 500, or 5 to 200, or 5 to 100, or 5 to 50, or 6 to 40, or 6 to 30, or 6 to 15 or 6 to 12, or about 9 beta-sheet domains. The beta sheet regions may comprise a plurality of consecutive alanine residues, or a plurality of other amino acids that can form hydrogen bonds and that are typically arranged in consecutive order in beta sheet regions, and may range from about or 3 to 50, or 4 to 40, or 4 to 30, or 4 to 15, or 4 to 12, or 6 to 10, or about 9 consecutive hydrogen bonding amino acids (e.g., (Ala-Ala-Ala-Ala-Ala-Ala-Ala-Ala-Ala). In certain embodiments, the spider silk polypeptide may comprise from 4 to 1000, or 4 to 800, or 4 to 500, or 5 to 200, or 5 to 100, or 5 to 50, or 6 to 40, or 6 to 30, or 6 to 15 or 6 to 12, or about 9 or 10 alpha helix domains. The alpha helix domains may comprise a plurality of glycine residues interspersed with other amino acids (e.g., Q, Y, L, S. R, A or P) typically found in alpha helix domains, and may range from about 4 to 200, or 5 to 100, 5 to 50, or 6 to 45, or 12 to 40, or 12 to 45 amino acids in length. Thus, in alternate embodiments, the spider silk analog may comprise a sequence made up of about 4 to 1000, or 4 to 800, or 4 to 500, or 5 to 200, or 5 to 100, or 5 to 50, or 6 to 40, or 6 to 30, or 6 to 15 or 6 to 12, or about 9 spider silk beta-sheet domains alternating with about 4 to 1000, or 4 to 800, or 4 to 500, or 5 to 200, or 5 to 100, or 5 to 50, or 6 to 40, or 6 to 30, or 6 to 15 or 6 to 12, or about 9 to10 spider silk alpha helix domains.

For example, in certain embodiments of the methods, compositions and systems of the present invention, the spider silk peptide domains are derived from, i.e., are at least 50%, 60%, 70%, 80%, 90%, 95%, 96%, 97%, or 98% identical to spider silk fibroin sequences. Also, a spider silk analog may comprise a single polypeptide having a mixture of different spider silk polypeptide domains, or analogs thereof, either from the same or different species. Thus, in certain embodiments, the fusion gene construct comprises a nucleic acid that encodes for a peptide having the amino acid sequence as set forth in at least one of SEQ ID NO: 36, SEQ ID NO: 37, SEQ ID NO: 38, SEQ ID NO: 39, SEQ ID NO: 40, or SEQ ID NO: 41. Or, the fusion gene construct may comprise a nucleic acid that encodes for a spider silk analog peptide having the amino acid sequence as set forth in SEQ ID NO: 2.

Example domains that may be used to generate a spider silk polypeptide analog include the following peptides: LGGQGAAAAAAAAAGGGGQGG (SEQ ID NO 36), GYGGLGSQAGRGG (SEQ ID NO: 37), LGGQGGGQ (SEQ ID NO: 38), GSRGG (SEQ ID NO: 39), LGGQGAAAAAAAAGAGGGQGG (SEQ ID NO 40), and LGGQGAGQ (SEQ ID NO: 41). Thus, as discussed in more detail herein, the spider silk sequences, or an analog thereof, (e.g., SEQ ID NO: 2) of the methods, compositions and systems of the present invention may comprise a single internal repeat unit (I) which is made up of smaller units: SEQ ID NO: 36, SEQ ID NO: 37, SEQ ID NO: 38, SEQ ID NO: 39, SEQ ID NO: 40 and/or SEQ ID NO: 41. However, various embodiments of the methods, compositions and systems of the present invention comprise one or more of these internal repeats ligated to various silkworm 5' and 3' ends. Also, the recombinant constructs may comprise a reporter gene, such as a green fluorescent protein to facilitate determination of whether successful transformation has occurred.

Thus, in certain embodiments the construct may comprise at least one of the following:
(a) a recombinant DNA construct (SEQ ID NO: 30) that encodes from 5' to 3'—a *Bombyx mori* silkworm 5' sequence (5'), one repeat of a spider silk analog (I), and a silkworm 3' sequence (3');
(b) a recombinant DNA construct (SEQ ID NO: 31) that encodes from 5' to 3'—a *Bombyx mori* silkworm 5' sequence (5'); one repeat of a spider silk analog (I); a green fluorescent protein (GFP) polypeptide (E) and a silkworm 3' sequence (3');
(c) a recombinant DNA construct (SEQ ID NO: 32) that encodes from 5' to 3'—a *Bombyx mori* silkworm 5' sequence (5'), two repeats of a spider silk analog ($I_2$), and a silkworm 3' sequence (3');
(d) a recombinant DNA construct (SEQ ID NO: 33) that encodes from 5' to 3'—a *Bombyx mori* silkworm 5' sequence (5'), two repeats of a spider silk analog ($I_2$), a green fluorescent protein (GFP) polypeptide (E), and a silkworm 3' sequence (3');
(e) a recombinant DNA construct (SEQ ID NO: 34) that encodes from 5' to 3'—a *Bombyx mori* silkworm 5' sequence (5'), three repeats of a spider silk analog (I), and a silkworm 3' sequence (3'); or
(f) a recombinant DNA construct (SEQ ID NO: 35) that encodes from 5' to 3'—a *Bombyx mori* silkworm 5' sequence (5'), three repeats of a spider silk analog (13), a green fluorescent protein (GFP) polypeptide (E), and a silkworm 3' sequence (3').

Additional sequences having multiple copies of the internal repeat (I) ranging from 2 to 1000 or more may be generated using the sequence disclosed herein as embodiments of the spider silk analog constructs of the present invention. Or sequences at least 70%, or 75%, or 80%, or 85%, or 90%, or 95%, or 96%, or 97%, or 98% or 99% identical to each of these sequences may be used.

As detailed herein, the DNA encoding a spider silk polypeptide, or analog thereof, used in the methods, compositions and systems of the present invention may be operably linked to silkworm sequences so as to promote site-specific insertion of the DNA encoding the spider silk peptide or analog thereof into the silkworm genome. The length of the 5' and 3' ends of the silkworm gene should be long enough such that homologous recombination between the recombinant spider silk/silkworm silk fusion gene can occur. In alternate embodiments, the 5' and/or 3' ends may comprise at least 200, or at least 300, or at least 400, or at least 500, or at least 600, or at least 700, or at least 800, or at least 900, or at least 1000, or at least 1100, or at least 1200, or at least 1300, or at least 1400, or at least 1500, or at least 1600, or at least 1700, or at least 1800, or at least 1900, or at least 2000 nucleotides of the silkworm genomic DNA. Also, in alternate embodiments, the 5' and/or 3' ends may comprise about 100 to 3000, or 200 to 2500, or 300 to 2000, or 400 to 1800, or 500 to 1600, or 500 to 1500, or 500 to 1400, or 500 to 1200, or 500 to 1100 nucleotides of the silkworm genomic DNA. Or, ranges within these ranges may be used. For example, in certain embodiments the fusion gene construct comprises a nucleic acid that encodes for a silkworm silk gene 5' end having a sequence as set forth in at least one of SEQ ID NO: 5, 10, 15 or 20. Also in certain embodiments, the fusion gene construct comprises a nucleic acid that encodes for a silkworm silk gene 3' end having a sequence as set forth in at least one of SEQ ID NO: 8, 13, 18 or 22.

In other embodiments, the present invention comprises recombinant and/or isolated DNA and/or polypeptides comprising silkworm sequences as set forth in at least one of SEQ ID NOS: 1-41, or a sequence at least 70% or 75%, or 80%, or 85%, or 90%, or 95%, or 96%, or 97%, or 98% or 99% identical thereto. Thus, in certain embodiments, the present invention comprises an isolated DNA comprising at least one of the sequences as set forth in SEQ ID NOS: 1, 3, 5, 8, 10, 13, 15, 18, 20, 22 and 30-35. Or, the present invention may comprise an isolated DNA encoding a peptide comprising the amino acid sequence as set forth in SEQ ID NO: 36, SEQ ID NO: 37, SEQ ID NO: 38, SEQ ID NO: 39, SEQ ID NO: 40, or SEQ ID NO: 41. Also, in certain embodiments, the present invention comprises recombinant and/or isolated DNA and/or polypeptides comprising sequences as set forth in any of the sequences disclosed herein or combinations thereof as described herein.

The present invention comprises silkworm eggs or larvae that have been transformed using the methods or constructs of the present invention. Thus, the silkworm eggs or larvae may comprise any of the sequences described herein.

In certain embodiments, the recombinant construct is combined with an adjuvant to increase transformation of silkworm eggs. The adjuvants may comprise any of a number of cationic lipid preparations used for transfection (e.g. Transfectin from Bio-Rad Laboratories, or Gene Juice from EMD Chemicals), but may also or alternatively include calcium phosphate preparations, or dendrimers (e.g. SuperFect from Qiagen), or high velocity coated nanoparticles (e.g. Gene Gun from Bio-Rad Laboratories). Or, other transfection preparations and techniques known to the art may be used.

To generate recombinant silkworms of the present invention, the method may comprise transforming silkworms by introducing the recombinant spider silk/silkworm silk fusion gene into a silkworm during either the egg or larval stage. Once the eggs are transformed, the method may further comprise rearing the resulting larvae, and screening the silkworms for transformation with the spider silk/silkworm silk fusion gene.

In one embodiment, the silkworm made using the methods, compositions and systems of the present invention is capable of producing a silk comprising a spider silk polypeptide, or an analog of a spider silk polypeptide. In certain embodiments, the spider silk polypeptide is encoded by a recombinant DNA. In one embodiment, the spider silk gene or analog thereof replaces a silkworm gene for silk. In one embodiment, the gene introduced into the silkworm is a fusion gene that encodes a polypeptide comprising spider silk and silkworm silk sequences (i.e., a spider silk/silkworm silk fusion). The methods may be used to introduce spider silk fibroin sequences or analogs thereof into a silkworm or other producer.

In alternate embodiments, the spider silk analog may be inserted into the silkworm heavy chain fibroin gene and/or the light chain silkworm fibroin gene. For example, in some embodiments, a spider silk chain is inserted into both the light and heavy chain loci in the silkworm. In this way a silk of increased strength may be produced. Or, in some embodiments, a spider silk fibroin analog is inserted into the heavy chain loci in the silkworm and a different spider silk fibroin analog is inserted into the silkworm light chain loci to produce a more flexible silk.

In certain embodiments, recombination occurs at a single genetic locus for fibroin. For example, recombination may occur such that a single silkworm light fibroin gene is excised and replaced by a spider silk/silkworm silk fusion gene construct of the invention. Additionally or alternatively, recombination may occur such that a single silkworm heavy fibroin gene is excised and replaced by a spider silk/silkworm silk fusion gene construct of the invention. The present invention may further comprise breeding such heterozygote to generate homozygotes at either locus. For example, two light fibroin heterozygotes may be mated to generate offspring that are homozygous at the silkworm light chain loci for a spider silk/silkworm silk fusion gene that encodes a spider silk fibroin, or two different spider silk fibroins, or analogs thereof. Or, two heavy fibroin heterozygotes may be mated to generate offspring that are homozygous at the silkworm heavy chain loci for a fusion gene that encodes a spider silk fibroin, or two different spider silk fibroins, or analogs thereof.

In certain embodiments, the present invention may further comprise breeding the recombinant silkworms to generate silkworms with recombinant genes in both silkworm heavy loci or both silkworm light fibroin loci by cross-breeding individuals transformed with a spider silk/silkworm fusion gene for the silkworm light fibroin with individuals that are transformed with a spider silk/silkworm silk fusion gene for the silkworm heavy fibroin. Or, silkworms that are heterologous at both the light and heavy chain loci (e.g., by heterologous recombination at both the silkworm heavy and light chain genomic loci) can be mated to generate offspring that are homozygous for spider silk fusion genes for both the light and heavy fibroin loci.

Embodiments of the methods, compositions and systems of the present invention can thus allow for expression of spider silk analog polypeptides in silkworms without dilution by native silkworm silk polypeptides. Thus, in certain embodiments, at least one of the light fibroin chain or the heavy fibroin chain in a recipient silkworm are replaced, respectively, by a fusion gene constructs encoding a spider silk analogs at both the light fibroin and heavy fibroin loci. In certain embodiments, the fused gene is able to replace a native gene present in the silkworm such that the transformed silkworm expresses a polypeptide comprising a spider silk fibroin polypeptide, or an analog thereof, and expresses significantly less of the native silkworm silk. For example, embodiments of the transformants of the present invention may produce not more than 80%, not more than 70%, or not more than 60%, or not more than 50%, or not more than 40%, or not more than 30%, or not more than 20%, or not more than 10% of the native silkworm silk. In some cases, the transformants only produce silk comprising spider silk polypeptides, or analogs thereof.

In certain embodiments of the methods, compositions and systems of the present invention, the recombinant DNA comprising a spider silk/silkworm silk gene includes DNA that encodes for a non-silk polypeptide. For example, in certain embodiments, the recombinant DNA may include sequences that encode for a detectable protein (i.e., a reporter gene). In this way, the presence of the spider silk/silkworm silk fusion gene may be detected by monitoring the detectable protein. In one embodiment, the detectable protein may be a fluorescent protein (e.g., green fluorescent protein) inserted downstream of the spider silk sequences and upstream of the 3' silkworm silk DNA sequences. Or, other fluorescent proteins may be inserted in the same or other locations in the polypeptide chain.

The spider silk analog peptides of the methods, compositions and systems of the present invention may have improved characteristics as compared to either silkworm silk or native spider silk. Thus, in certain embodiments, the methods, compositions and/or systems of the present invention are used to produce silkworms that express spider silk analog peptides that are stronger, or more flexible, or more elastic, or tougher than silkworm silk. In certain embodiments, the methods, compositions and/or systems of the present invention are use to produce silkworms that express spider silk analog peptides that are stronger, or more flexible, or more elastic or tougher than native spider silk.

For example, the spider silk analogs of the present invention may exhibit increased strength and/or durability. In alternate embodiments, the transformed silkworm may produce a silk that is at least 10%, or 15%, or 25%, or 40%, or 50%, or 75%, or 100%, or 2-fold, or 5-fold, 10-fold, or 20-fold stronger than native silkworm silk. Strength is defined as Pascals/square meter, or how much weight a given fiber can support.

Or, a silk having increased flexibility may be produced using the methods, compositions and systems of the present invention. In alternate embodiments, the transformed silkworm may produce a silk that is at least 10%, or 15%, or 25%, or 40%, or 50%, or 75%, or 100% or 2-fold, or 5-fold, 10-fold, or 20-fold more elastic than silkworm silk.

Additionally or alternatively, the transformed silkworm may produce a silk that is at least 10%, or 15%, or 25%, or 40%, or 50%, or 75%, or 100%, or 2-fold, or 5-fold, 10-fold, or 20-fold tougher than native silkworm silk. As used herein, toughness is defined as the amount of energy that can be absorbed, or Pascals/cubic meter.

Or, the transformed silkworm may produce a silk that has at least a 10%, or 15%, or 25%, or 40%, or 50%, or 75%, or 100%, or 2-fold, or 5-fold, 10-fold, or 20-fold higher breaking energy than native silkworm silk. As used herein, breaking energy is joules/kg as opposed to toughness in joules/cubic meter.

The methods, compositions and systems of the present invention may comprise using a single type of silkworm, or a variety of different types of silkworms. In an embodiment, the silkworm comprises a silkworm of the *Bombyx* genus. A variety of *Bombyx* strains may be used including, but not limited to, *Bombyx mori, Bombyx mandarina*, or hybrids thereof. Or, the silkworm may comprise a silkworm of the *Antheraea* genus or any other Saturniid. Also, the method may comprise transferring the recombinant fibroin genes into a plurality of varieties of silkworms by breeding the recombinant silkworms.

For example, in one embodiment, the method may comprise a method as outlined in FIG. 1. Thus, the method 20 may comprise the step of ligating a DNA sequence coding for a spider silk polypeptide, or an analog thereof, between portions of the 5' and 3' ends of the *Bombyx* fibroin gene to create a fusion gene 22. The 5' and 3' ends of the *Bombyx* fibroin gene should be long enough (i.e., provide sufficient DNA sequence from the native *Bombyx* gene) to allow for homologous recombination to take place when the recombinant gene is placed in a silkworm host such that the native *Bombyx* light or heavy fibroin gene is replaced with the corresponding light or heavy fusion (i.e., spider silk protein/silkworm silk) gene. Either the heavy fibroin chain, the light chain, or both, can be replaced by this procedure.

The method may also comprise the step of placing the fused gene into a suitable form for homologous recombination 24. In these embodiments, the recombinant gene may be delivered to the silkworm as a plasmid, viral vector, or naked DNA with, or without, adjuvants. The method may also comprise transforming silkworms by introducing the fusion gene in a form that is suitable for homologous recombination into the silkworms either the egg or larval stage 26. The method may further comprise rearing the resulting larvae and screening for transformation 28.

A variety of methods may be used to screen the eggs or larvae for transformation. In an embodiment, a portion of the eggs or larvae are isolated and the presence of the spider silk sequences determined by detection of the spider silk DNA (e.g., by PCR using spider silk primers and/or Southern blotting). Also, the eggs and/or larvae may be assayed for the production of protein having the biochemical characteristics of silk, such as molecular weight, a silk-like appearance, and/or other biophysical parameters such as strength or elasticity. Or the silk or insects can be examined for visible markers such as a fluorescent protein included as part of the spider silk/silkworm silk construct. For example, measurements of physical characteristics of silk produced by recombinant silkworms is described in the Examples herein.

The method may further comprise using standard breeding techniques to generate silkworms homozygous for the engineered fibroin 30. Further breeding can be used to generate silkworms with both the light fibroin and/or the heavy fibroin loci transformed, so as to generate homozygotes for expression of spider silk sequences in place of either the heavy and light chains. Additionally or alternatively, the method may comprise cross-breeding individuals having a fusion gene for a first spider silk fibroin at the light chain locus with individuals that have been transformed with the same, or more likely, a different spider silk gene at the heavy fibroin fusion gene. The recombinant fibroin genes can also be moved into more desirable varieties of silkworms by standard breeding techniques.

For example, the *Bombyx mori* silkworm has a single locus for the heavy fibroin gene on chromosome 25, and another single locus for the light chain fibroin on chromosome 14 (Hyodo et al, The Japanese Journal of Genetics, 59 (3): pp. 285-296 (1984)). There are two copies of each gene in diploid cells. A transformation event would most likely occur only in one of the fibroin alleles, thus the offspring of that transformation event would be heterozygous at that locus. Breeding such heterozygotes would yield offspring in the ratio of 1:2:1 homozygous transformants, heterozygous transformants, homozygous wild type respectively. Testing of offspring (e.g. PCR of a few microliters of hemolymph) allows for selection of the desired homozygous individuals for further breeding. Crossing individuals homozygous for transformed heavy chain fibroin with a homozygote for transformed light chain fibroin would yield double heterozygotes. Crossing these offspring would yield a mix of genotypes in the ratio 1:1:2:2:4:2:2:1:1. Selection of the appropriate individuals would allow establishing a breeding population of double homozygous transformants.

Figure 2:
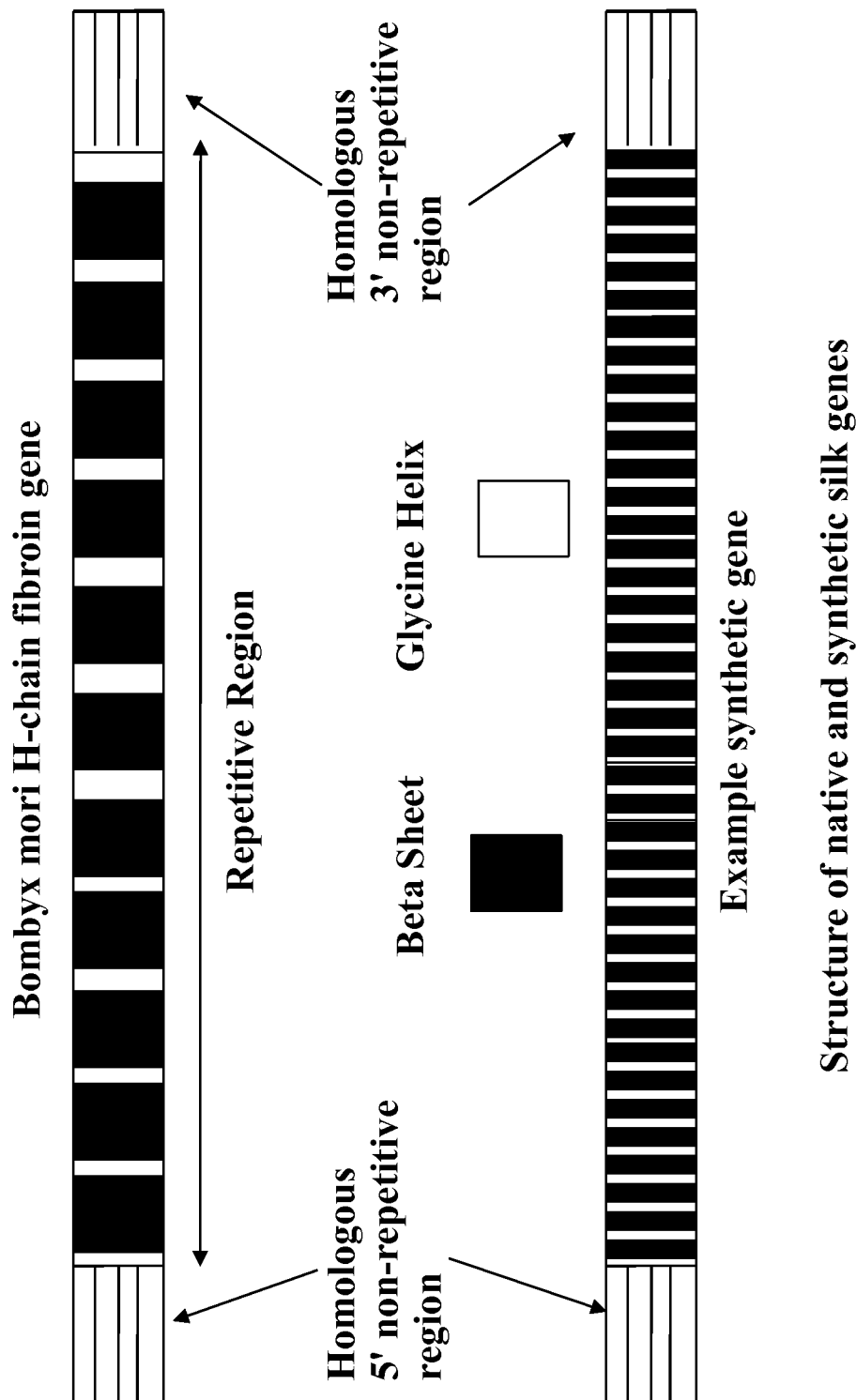
FIG. 2 shows a schematic comparison of the structural organization of the *Bombyx mori* fibroin gene and the synthetic spider silk gene of the invention.

FIG. 2 shows a schematic comparison of the structural organization of the *Bombyx mori* fibroin gene (upper DNA molecule) and a synthetic spider silk gene of the invention (lower DNA molecule). As described in more detail herein, the spider silk analog polypeptide of the present invention comprises a repeated unit (denoted herein as an "internal repeat" or I) of about 316 amino acids. The 316 amino acid internal repeat may include 4 domains having the following sequences: LGGQGAAAAAAAAAGGGGQGG (SEQ ID NO 36), GYGGLGSQAGRGG (SEQ ID NO: 37), LGGQGAGQ (SEQ ID NO: 38), and GSGRGG (SEQ ID NO: 39) which are derived as spider silk polypeptide consensus sequences. Or, in certain embodiments, SEQ ID NO: 38 is changed to SEQ ID NO: 41, and SEQ ID NO: 36 is changed to SEQ ID NO: 40, to remove GAG regions, as described herein.

As further described below, multiple repeats of the 316 amino acid unit may be linked together to form a synthetic spider silk gene comprised of beta sheet sequences interspersed between glycine helices. The native *Bombyx* silk also comprises beta sheet sequences and glycine helices, but that the organization is different. For example, spider silks are different than silkworm silk in having short beta sheets interspersed with alpha helix or random coil sections. Thus, as compared to the spider silk analogs of the present invention, *Bombyx* silk has substantially more beta sheet domain. In other embodiments, spider silk analogs may be designed to have proline residues so as to make them extremely elastic. Or other modifications may be made.

Figure 3:
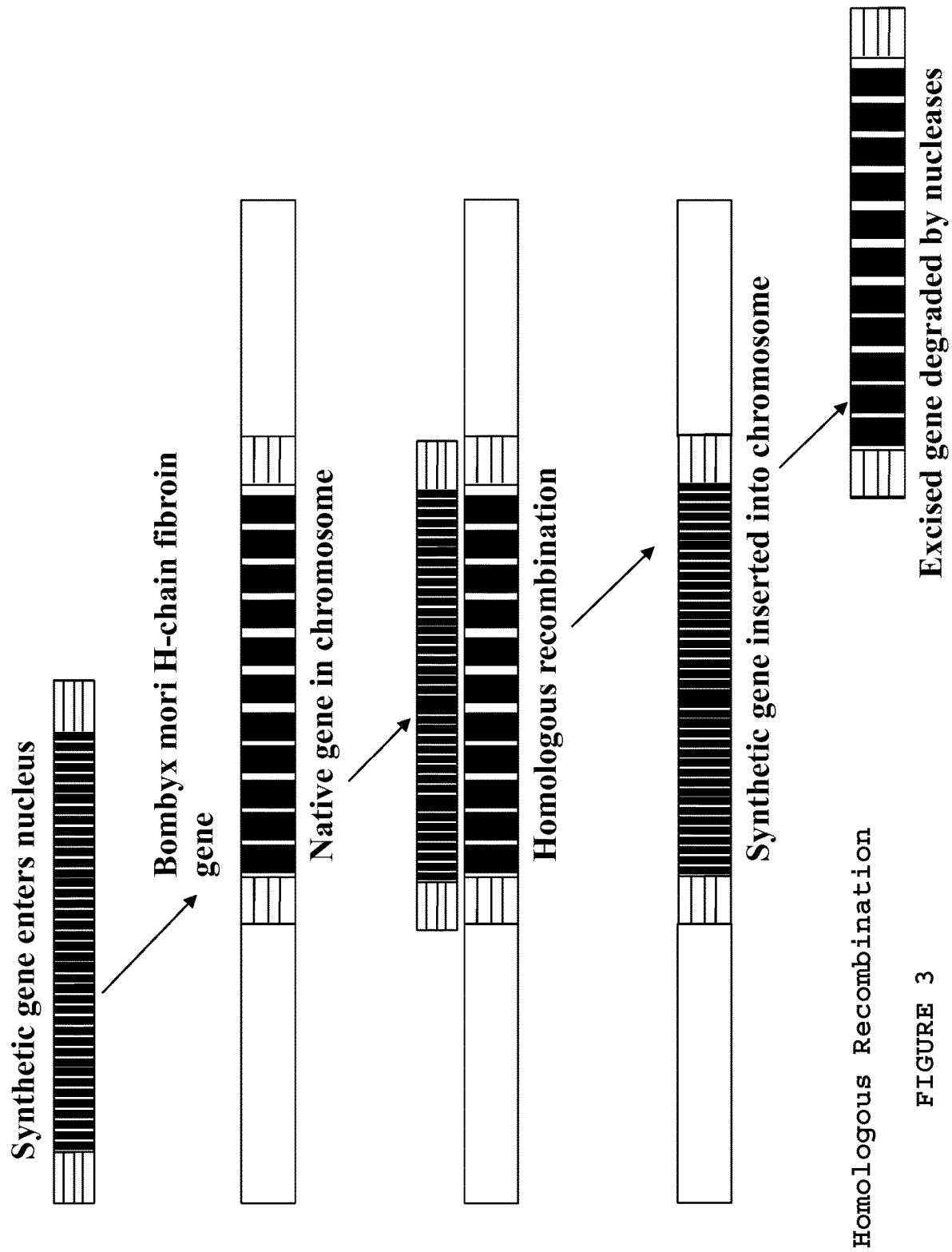
FIG. 3 shows a schematic representation of the method used to introduce the spider silk gene into *Bombyx* silkworms.

FIG. 3 shows a schematic representation of the method used to introduce the spider silk gene into a *Bombyx* silkworm. As described in more detail herein, the synthetic fusion gene is constructed to include 5' and 3' ends that are the same sequence as the 5' and 3' sequence of the *Bombyx* fibroin gene. Thus, the synthetic fusion gene can insert itself into the locus of the native *Bombyx* fibroin gene by site-specific homologous recombination, thereby excising the fibroin gene. The excised gene is then be degraded by nucleases.

The silkworm genes for heavy and light chain fibroin are controlled by a number of factors. For the heavy chain there are five promoters within the 200 base pairs (bp) upstream of the TATA box. Also, 67 bp downstream of the start site is an intron that appears to influence transcriptional regulation (Takyia, F., et al., *BioChem* 1, 321, 645-653 (1997)). The 3' end of the heavy chain also appears to contain an essential cysteine for bonding with the light chain. The light chain has similar essential elements in the 5' and 3' region (Yamaguchi, K., et al., *J. Mol. Biol.* 210, 127-139 (1989)). By replacing the repetitive portion of the silk genes and leaving the 5' and 3' regulating regions and essential cysteine residues unchanged, optimal production of the recombinant protein can occur. Further, by removing the native gene's repetitive regions that encode for the majority of the silkworm silk structural polypeptide, there should be no production of native silkworm silk. This is in contrast to other systems which employ insertion of a spider silk gene at a separate location in the silkworm genome, leaving the native silkworm gene unaltered; in these systems, the spider silk polypeptide is expressed in combination with the silkworm silk polypeptide. In the system of the present invention, the spider silk peptide effectively replaces the silkworm silk polypeptide.

In certain embodiments, the spider sequence is modified so as to comprise an analog or a biological equivalent of the native sequence. There are many published sequences for protein fibers, and which elucidate the structural properties that make for strong or very elastic fibers. Thus, the present invention includes making modifications to the structure of the spider silk polypeptide that may enhance the function and/or strength of the fiber.

FIG. 4A shows an embodiment of a DNA sequence (SEQ ID NO: 1) that encodes for a spider silk polypeptide analog (SEQ ID NO: 2) which can be denoted as an internal repeat I of the present invention. The repetitive region of the spider silk analog used for production of the spider silk/silkworm silk fusion gene may be designed by comparing published sequences of *Nephila clavipes* dragline silk and determining commonly repeated motifs. In one embodiment, the spider silk amino acid repeat units were combined into a 316 amino acid sequence with nine beta sheet forming regions interspersed between glycine helices, and the peptide sequences were used to derive a corresponding DNA sequence. Also, as illustrated by the embodiment shown in FIGS. 4A and 4B, the DNA sequence may be edited to reduce repeated codons, and/or to remove selected restriction sites, and/or to reflect *Bombyx* codon biases. Also, the sequence may be modified to insert restriction endonuclease sites that are useful for cloning. In one embodiment, a BspEI site may be added at the 5' end, and an XmaI site added at the 3' end (see e.g., FIG. 4).

Spider silk undergoes a phenomenon called supercontraction. When wetted, spider silk greatly reduces its length, and becomes more plastic (Work, R. W., *J. exp. Biol.,* 118, 379-404 (1985)). It is believed that the ability of spider silk to exhibit supercontraction is due to the presence of specific alanine residues that are encoded as GAG repeats at the end of the polyalanine runs (Lewis, *Chem. Rev.,* 106 (9), 3762-3774, (2006)). As increased plasticity may be an undesirable characteristic for high strength fabrics, the GAG motifs may be edited out of the DNA sequence used to generate the synthetic fusion gene. For example, for the sequence shown in FIG. 4A (SEQ ID NO: 2), GAG regions at the 5' end of the beta sheet domain were converted to GAA, and GAG regions at the 5' end of the alpha helix domain were converted to GGG by modifying the native sequence domains (SEQ ID NO: 3) to generate the alternate spider silk peptide (SEQ ID NO: 4) as shown in FIG. 4B.

Figure 4C:
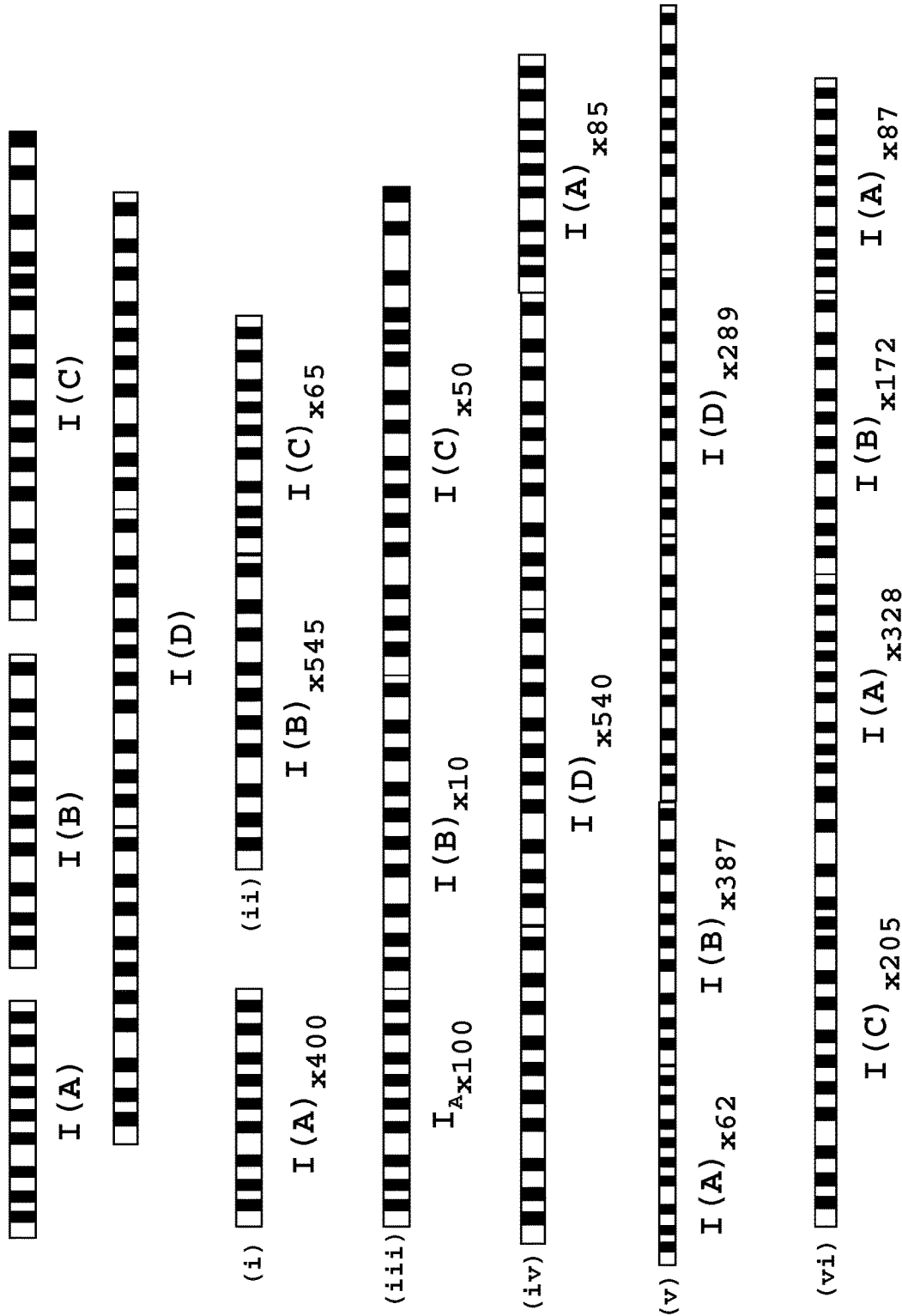
FIG. 4C shows an illustration of how a plurality of internal repeat segments, each of which comprise a plurality of beta sheet (dark regions) and alpha helix domains (light regions), may be combined to generate a spider silk analog polypeptide.

In certain embodiments, the spider silk polypeptide, or analog thereof may comprise a single spider silk internal repeat domain (I) of alternating beta sheet domains (dark regions) alternating with alpha helix domains (light colored regions) such as IA, IB, IC, or ID shown in FIG. 4C. Thus, the beta sheet regions, alpha helix regions and/or number of each may be varied to produce different internal repeats that can encode a spider silk polypeptide or analog thereof. Or, the spider silk polypeptide or analog thereof may comprise a plurality of the same or different single spider silk internal repeat domains (e.g., IA, IB, IC, ID and the like) linked end to end in various arrangements as depicted in FIG. 4C for constructs (i)-(vi).

In one embodiment, the 5' genomic sequence from the silkworm gene starts at the ATG start codon, and ends 33 nucleotides after the end of the first intron. Or, shorter or longer 5' regions may be used. In certain embodiments, however, the 5' non-repetitive silkworm sequence is long enough such that homologous recombination with the 5' end of the native silkworm gene can occur. Embodiments of 5' heavy chain DNA sequences for various species of silkworm are shown as SEQ ID NOS: 5, 10 and 15 in FIGS. 5, 7 and 9, respectively. Also, an embodiment of a 5' light chain fibroin sequence is shown as SEQ ID NO: 20 (FIG. 11). The 5' heavy chain fibroin sequences as shown as SEQ ID NO: 5, 10, and 15 have the upstream promoters intact, and the intron in its normal position. Thus, these sequences (promoter and intron) will still be in the correct position in the silkworm genome after homologous recombination.

In one embodiment, the sequence used as the 5' sequence may be modified to include a restriction endonuclease site at the 3' end of the sequence. In an embodiment, the restriction endonuclease site matches the restriction endonuclease site at the 5' end of the internal repeat sequences. For example, in one embodiment, the 5' heavy or light chain sequence comprises a BspEI restriction site at the 3' end to match with the internal repeat sequence 5' restriction site (SEQ ID NOS: 5, 10, 15 and 20).

As described herein, the fusion gene construct may also include a sequence to promote homologous recombination of the 3' end of the construct with the native silkworm gene. An example of 3' sequences from various silkworm species that may be used is shown as SEQ ID NOS: 8, 13, and 18 in FIGS. 6, 8, and 10, respectively. Also, an embodiment of a 3' light chain fibroin sequence is shown as SEQ ID NO: 22 (FIG. 12). In an embodiment, the 3' sequence may start 57 nucleotides upstream of the critical cysteine residue found in the native silkworm gene, and continue for about 664 nucleotides downstream of the terminal cysteine. The sequence may also comprise an in-frame XmaI site at the 5' end to match a 3' restriction site present on the internal repeat sequence (i.e., SEQ ID NOS: 8, 13, 18 and 22).

Figure 13:
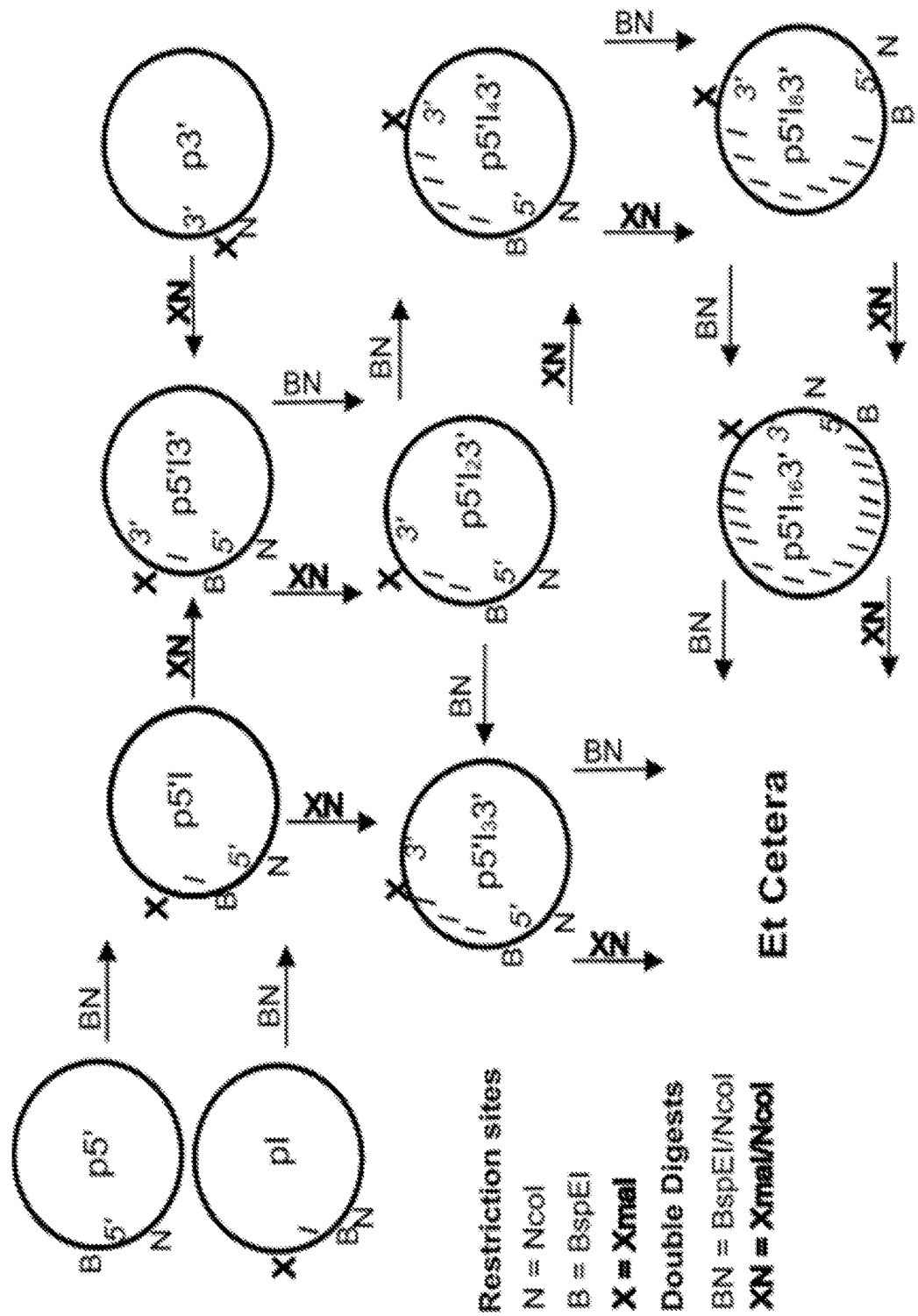
FIG. 13 shows a gene assembly route to generate recombinant plasmid constructs that include multiple numbers of the spider silk analog sequence, i.e., the spider silk internal repeat (I) linked to the silkworm 5' sequence (5'), and a silkworm 3' sequence (3') in accordance with one embodiment of the present invention.

In an embodiment, the gene sections may be inserted into a vector. In certain embodiments, the sections are combined in a manner such that multiple repeats of the spider silk polypeptide (e.g., multiple repeats of SEQ ID NO: 1) are linked end to end. For example, the gene sections may be inserted into pUCminus (pUC⁻) plasmids (Blue Heron Bio). The assembly of the synthetic fusion gene may then employ a series of ligation reactions as outlined in FIG. 13. First, the plasmids containing the 5' section (p5') and the internal repeating section (pI) may each be double digested with NcoI and BspEI. The resulting DNA fragments may then be gel purified, and the 5' DNA sequence ligated with the digested pI' to produce plasmid p5I' (FIG. 13).

Next, a plasmid with the 3' section (i.e., p3') may be digested with XmaI and NcoI, and plasmid P5'I may be digested with BspEI and NcoI. After gel purification, the digested p3' and the 5I segment may be ligated to form plasmid p5'I3' (FIG. 13). Purified p5'I3' may then be split into two fractions and digested with NcoI/BspEI and NcoI/XmaI. The NcoI/BspEI digested plasmid contains the 3'I section of the gene with a sticky end recognized by an XmaI digest; the digested plasmid may therefore be ligated with the purified XmaI/NcoI digested section to give a plasmid with the 5' section, two internal repeats, and the 3' section (p5'I$^2$3') (FIG. 13). This method of joining the sections destroys the restriction site between the repeating sections. Repeating the dual double digests and ligation allows the repeats to be generated in any number from 1 to as large as the vector and recombinase-minus host are able handle, or p5'I$^x$3' with x being any number from 1 to the limit of the vector/host. To produce repeat numbers outside of the series 1, 2, 4, 8, 16, 32 and so forth, would require using two plasmid having the required number of repeats such that the sum of the repeats provides the desired end-product. For example, to produce p5'I$^3$3', plasmid p5'I$^2$3' (containing 2 insert repeats) could be digested with BspEI/NcoI, and p5'I3' (containing 1 insert repeat) digested with XmaI/NcoI. Alternatively and/or additionally, different plasmids having different internal repeats (e.g., such as are depicted as IA, IB, IC, and ID of FIG. 4C) may be used to generate concatamers of different repeat units ligated together (e.g., p5'IA$_4$IB$_{50}$IC$_2$3' and the like). Ligation of the appropriate DNA pieces would produce the desired plasmid. This method of concantenation using a combination of isoschizomers and a common restriction site is broadly applicable to assembling repetitive gene constructs.

After construction of the gene, injection into either eggs or larvae can result in homologous recombination in some of the individuals. These can be identified with PCR screening, and used to establish colonies of transformed silkworms. Methods of injection and adjuvants that encourage DNA uptake and transformation/recombination are known in the art, as are methods of raising the silkworms and using PCR to screen for the new genes.

Figure 14:
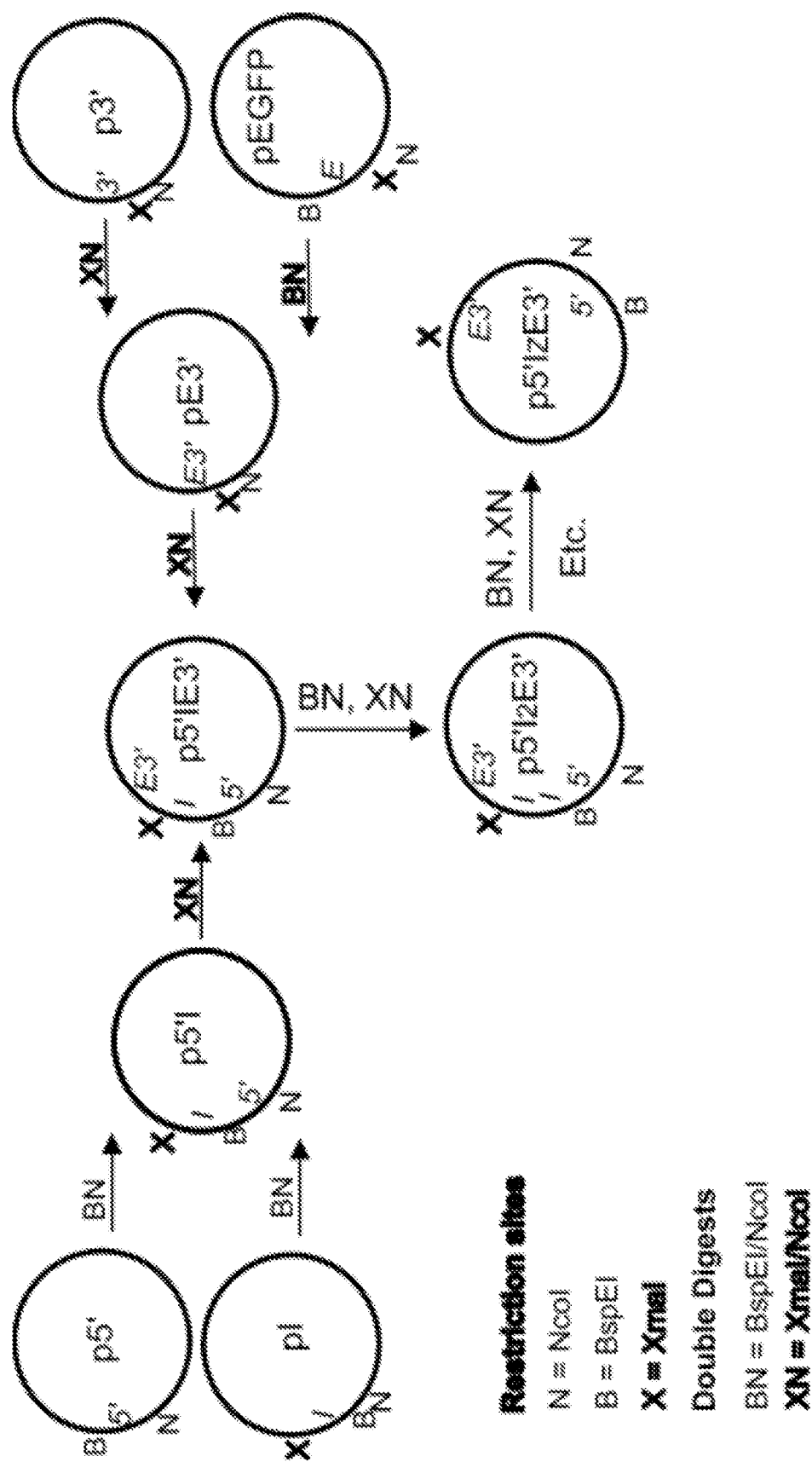
FIG. 14 shows a gene assembly route to generate recombinant plasmid constructs that include multiple numbers (z) of a spider silk analog sequence, i.e., a spider silk internal repeat (I), linked to the silkworm 5' sequence (5'), and a silkworm 3' sequence (3'), and including an eGFP marker gene (E) in accordance with one embodiment of the present invention.

Also, there are abundant marker genes that can be used to identify a transformation event. Many fluorescent proteins are readily available in plasmid form, and can be inserted in-frame into the silk sequence. For example to insert a GFP gene in-frame, a plasmid can be created with a GFP gene flanked 3' with a BspEI site and a combined XmaI/NcoI site on the 5' end. This can then be used in a scheme similar to that in FIG. 14 to produce a construct with multiple repeats (e.g., the same I, or different I, such as IA, IB, IC or ID) linked to a reporter gene. The silk gland in the larvae and the spun silk can then fluoresce green under appropriate illumination. Alternatively, the fluorescent protein can be paired with a promoter and inserted into the intron located at the 5' end of Saturniid fibroin genes. As an example, a GFP gene using a sericin promoter and 3' polyadenylation sequence is in FIG. 15. Use of BglII and XhoI restriction enzymes will allow the insertion of this construct into the intron of *Bombyx mori* fibroin, and result in GFP expression in the sericin layer of silk. This will be visible in the larvae and the silk. It will also be removable from the spun silk during the washing process, unlike the in-frame insertion.

The same process used to replace native fibroin genes with a new silk gene can also be used to knockout expression of the native gene. Homologous recombination that removes promoters, start sequences, a major portion of the gene, or introduces stop codons, will result in non-production of silk from that location on the chromosome. If other transformation processes such as random insertion using baculovirus and/or transposase mediated insertion are used to insert functional silk genes elsewhere in the genome, these would be produced without dilution by native silk molecules. The 5' portion of a knockout homologous recombination gene for the heavy chain fibroin is shown in FIG. 16.

EXAMPLES

The invention will be illustrated in further detail with the following examples.

Example 1—Design of the 5' and 3' Homologous Ends

The NCBI Entrez database was used to determine the sequence of the *Bombyx mori* heavy chain fibroin gene. Wu and Cao (J Zheijian Univ Sci., (2004) 5(6):644-650) had success using homologous sections of about 1 kb, Rubnitz and Subramani (Mol Cell Biol. 1984 November; 4(11): 2253-2258) report a sharp drop in efficiency below 214 bp. The 5' homologous section contains an intron of about 1 kb, and ~30 bp was added to each end to avoid possible effects on post-translational processing. To facilitate possible further use of the gene construct with other promoters, organisms, etc., the decision was made to begin the 5' sequence with the ATG start codon. This leaves the upstream promoters untouched and the intron in its normal place after homologous recombination. The 5' sequence was modified to have a BspEI restriction site at the 3' end to match with the internal repeat sequence 5' restriction site (FIG. 5).

The 3' sequence was chosen to start 57 nucleotides upstream of the critical cysteine residue, and continued 661 nucleotides downstream of the stop codon. The 3' sequence has an in-frame XmaI site at the 5' end to match the internal repeat sequence 3' restriction site (FIG. 6). Thus, both the 5' sequence and the 3' sequence include the essential elements while coding for a minimal amount of the peptide sequence. The gene constructs were ordered from Blue Heron Biotechnology, (Bothel W A 98021 USA) inserted into their pUC Minus plasmid.

Example 2—Design of the Internal Repeat Segment

NCBI Entrez was consulted to obtain published sequences of *Nephila* dragline silk which were used to determine commonly repeated motifs. These were reduced to 13 commonly occurring sequences, 4 of which are heavily represented in the highly repetitive portion of the gene: LGGQGAGAAAAAAAGGAGQGG (SEQ ID NO: 40), GYGGLGSQAGRGG (SEQ ID NO: 37), LGGQGAGQ (SEQ ID NO: 38), and GSGRGG (SEQ ID NO: 39). The sequences (SEQ ID NOS: 37, 38, and 39) were arranged into higher order motifs to reflect an approximation of the natural gene. The 316 amino acid sequence with nine beta sheet forming regions (shown in FIG. 4A) was translated into a DNA sequence and edited to reduce repeated codons, remove selected restriction sites, and reflect *Bombyx* codon biases. A BspEI site was added at the 5' end, and an XmaI site at the 3' end.

Spider silk undergoes a phenomenon called supercontraction. When wetted, it greatly reduces its length, and becomes more plastic Work, R. W., *J. exp. Biol.*, 118, 379-404 (1985).

Lewis, *Chem. Rev.*, 106 (9), 3762-3774, (2006), reports this is probably due to specific alanine residues, found in GAG repeats at the end of the polyalanine runs. As increased plasticity when wet can be an undesirable characteristic for high strength fabrics, the GAG motifs were edited out by single base changes. In general, 5' GAG repeats found in the spider silk beta sheet domain (see e.g., SEQ ID NO: 40) were converted to GAA, and 3' GAG were converted to GGG as shown in FIG. 4B (see e.g., SEQ ID NO: 36). Also, a similar change can be made to SEQ ID NO: 38 to generate SEQ ID NO: 41 for use in spider silk internal repeat constructs. The DNA sequence used as the spider silk repeat unit is shown as FIG. 4A (SEQ ID NO: 1).

Example 3—Assembling the Gene

The three gene segments had NcoI, BspEI, or XmaI restriction sites added so that they would remain in-frame when joined end to end, i.e., the 5' end (SEQ ID NO: 5) joined to the spider silk internal repeat (I) (SEQ ID NO: 1) joined to the 3' sequence (SEQ ID NO: 8). Plasmid p5' containing the *Bombyx* 5' homologous end (5' end, or 5') (SEQ ID NO: 5) and plasmid pI containing the internal repetitive section (I) (SEQ ID NO: 1) were digested with BspEI and NcoI. The digests were then run on agarose gel. The cut pI and 5' end bands were extracted with a glassmilk procedure and 0.1 µg of each were ligated and transformed into NEB's 10-beta *E. coli* to produce plasmid p5'I. Plasmids p5'I and p3' (containing the *Bombyx* 3' homologous end) were digested with XmaI and NcoI. The 5'I section and the cut p3' plasmid were gel purified and 0.1 µg of each were ligated and transformed into 10-beta *E. coli*, to generate plasmid p5'I3'. A preparation of p5'I3' was split and half digested with XmaI/NcoI, and the other half digested with BspEI/NcoI. The 5'I section produced by the XmaI/NcoI digest and the cut pI3' were again gel purified, ligated, and transformed to produce p5'I$^2$3' (shown as SEQ ID NO: 32 in FIG. 19).

As indicated in FIG. 13, the process of dual double digests and ligating can continue to produce a plasmid with the 5' and 3' ends and any number of insert repeats. To produce repeat numbers outside of the series 1, 2, 4, 8, 16, 32 and so forth, would require using two plasmid having the required number of repeats such that the sum of the repeats provides the desired end-product. For example, to produce p5'I$^3$3', plasmid p5'I$^2$3' (containing 2 insert repeats) could be digested with BspEI/NcoI, and p5'I3' (containing 1 insert repeat) digested with XmaI/NcoI. Ligation of the appropriate DNA pieces would produce the desired plasmid.

Example 4—Transformation of Silkworms with p5'I$^2$3' p5'I$^2$3' was prepared using Novagen's Insect Gene Juice as per the manufacturer's directions, using Bio-Whitaker's Insect X-press serum free media for dilution. One hundred late third instar larvae were injected with 25 µl of transfection mix; about 300 ng plasmid per insect. A Hamilton 50 µl syringe with a 30 gauge #4 point needle was inserted laterally near the 5$^{th}$ abdominal segment, run up to near the 4$^{th}$ abdominal segment, and the media injected slowly. The needle was kept in for about 5 seconds after the injection was complete to allow for equilibration: too early a removal resulted in some of the media being expelled.

The injected larvae were placed in a 27° C. incubator at ~70% humidity and fed on artificial diet until pupation. There was a 98% survival rate during the two weeks to pupation, but 20% died during the wandering or spinning stages, and 30% of the survivors failed to emerge on their own. The surviving enclosed adults were paired on starch paper and allowed to mate. After two hours the males were separated and the females allowed to lay eggs. Twenty-two egg masses resulted and were given sequential batch numbers.

Four days after laying, the egg masses had approximately 25% of their eggs removed and the genomic DNA extracted with a cartridge based kit. PCR using primers specific to the inserted repetitive region or the native sequence revealed two strong transformation events, that is, a positive PCR for the transgene and a weak or absent response to the genomic primers. Three others indicated a more balanced mixture of transgenic and native sequence, and four others showed anomalous banding, not clearly one or the other. All eggs masses were placed in a 4° C. chamber to complete diapause.

After one month four egg masses were selected and brought to room temperature for three hours. They were then soaked in 4.5 M HCl at 48° C. for five minutes, washed three times with water and allowed to air-dry. The eggs were placed in a humid 27° C. incubator. At 10-12 days the eggs began to hatch, and emergence over three days was essentially 100%. The larvae were fed on artificial diet and placed in pupation containers when they reached the wandering stage. After one week the cocoons were carefully removed, the floss gently stripped off, and the strength and elasticity measured with a tensiometer. This was accomplished by carefully stripping single fibers of 20-30 cm from the cocoon. These were fastened to the tensiometer and a ten cm section strained at approximately 3%/sec. Five to ten segments were tested from each cocoon. Silk from untreated larvae was used as the control. The cocoons were placed in labeled individual containers in the incubator and left to emerge.

Results

Figure 23:
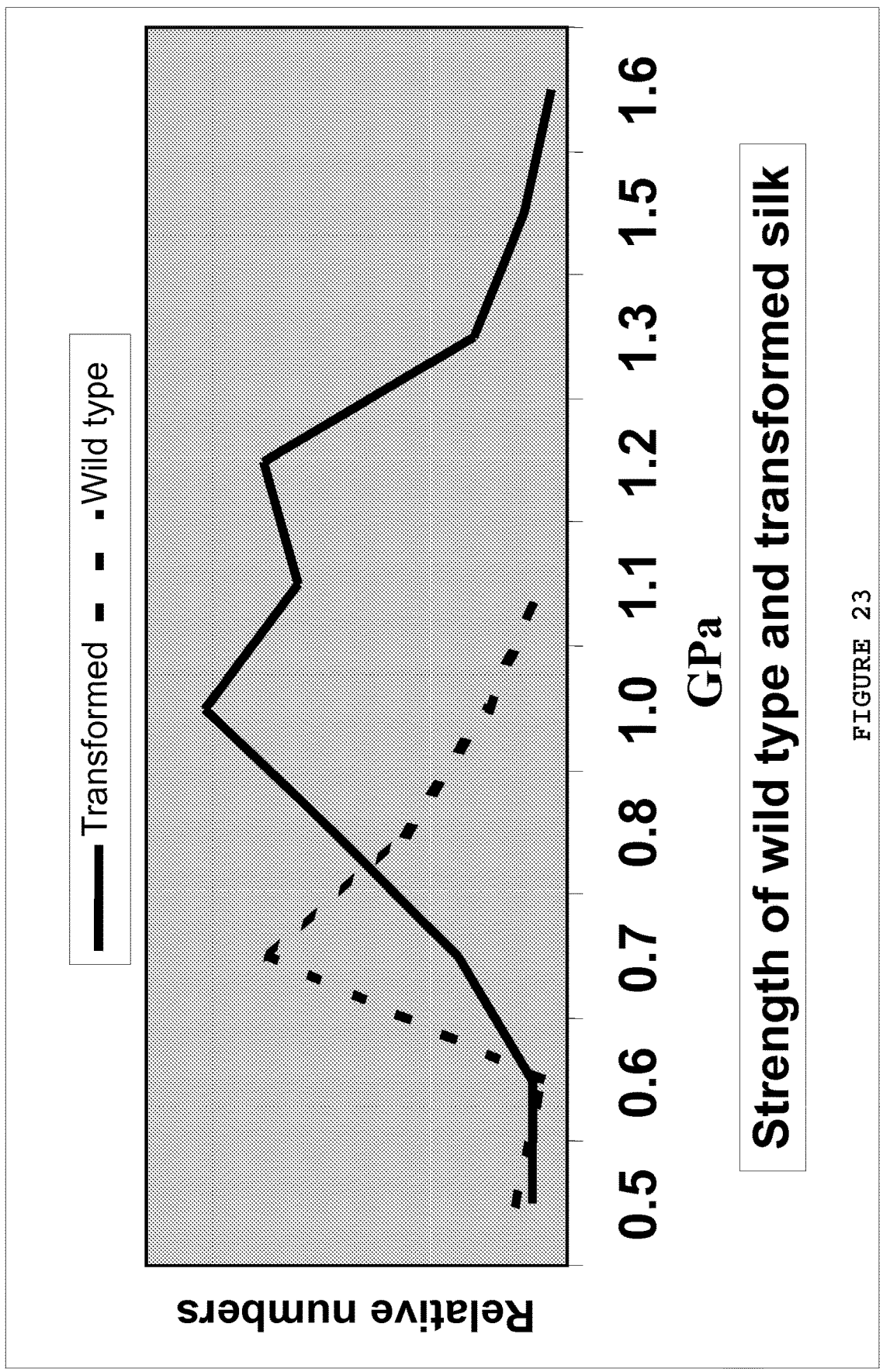
FIG. 23 shows a comparison of the strength of wild-type (wild type) silkworm silk and the silk of the progeny of silkworms transformed with an embodiments of a construct of the invention (i.e., SEQ ID NO: 32) (transformed); for the transformed silkworms, a portion of the eggs from silkworms that had been injected with the recombinant DNA and then mated were tested for the presence of the altered silk gene (i.e., the spider silk construct) and silk was isolated from cocoons that developed from a remainder of the eggs.

The transformed silk was significantly different from natural silk. The strength of natural silk was measured at 0.78±0.06 GPa. The transformed silk showed two curves (FIG. 23), with means of 1.02±0.04 GPa and 1.095±0.03 GPa. Elasticity was also significantly different. Natural silk had an elasticity of 14±1.5%, while the transformed silk could be divided into two groups, high and low elasticity, measuring 22±0.7% and 33±1.0%, respectively (Table 1). It can be seen that for both types of transformants (high and low elasticity) the strength was about the same, and significantly greater than the native silk.

Table 2 shows a comparison of the strength, elasticity, toughness and breaking energy for wild-type silkworm silk (i.e., *Bombyx* silk), and the silk of silkworms transformed with two different constructs of the invention: the 5'-I$^2$-3' construct (SEQ ID NO: 32) (Trans/Silk 2 rpt) and the 5'-I$^2$-3' construct (SEQ ID NO: 34) (Trans/Silk 3 rpt), as compared to literature values for spider silk, silkworm silk (*Bombyx* silk), and KEVLAR™. The transformed silk compares very closely with natural spider silk in toughness and elasticity. The two ranges of strength and elasticity for the transformed silk seems to indicate that mating of the G0 transformed insects resulted in a number of homozygous transformed individuals in the G1 generation; about 21%, or close to the expected Mendelian result for two heterozygous parents. This result may be due to selecting egg masses that showed strong PCR evidence of transformation for rearing.

TABLE 1

|  | Elasticity (%) | SD* | 95% Confidence |
|---|---|---|---|
| Natural Silk | 14.059 | 3.85 | ±1.54 |
| Low Transformed | 21.562 | 4.00 | ±0.69 |
| High Transformed | 32.718 | 2.86 | ±0.91 |

|  | Strength (GPa) | SD | 95% Confidence |
|---|---|---|---|
| Natural Silk | 0.776 | 0.142 | ±0.60 |
| Low Transformed | 1.016 | 0.219 | ±0.04 |
| High Transformed | 1.095 | 0.159 | ±0.03 |

*Standard Deviation

TABLE 2

|  | Strength | Elasticity | Toughness | Breaking Energy |
|---|---|---|---|---|
| Literature | Pascals | % | Joule/cubic M | Joules/kg |
| Spider Silk | 1.10E+09 | 35 | 1.60E+08 | 4.00E+05 |
| Bombyx Silk | 6.00E+08 | 18 | 7.00E+07 | 3.00E+04 |
| Kelvar | 3.60E+09 | 3 | 5.00E+07 | 3.30E+04 |
| Measured | Pascals | % | Joule/cubic M | Joules/kg |
| Trans. Silk 2 rpt | 1.09E+09 | 33 | 1.90E+08 | 3.85E+05 |
| Trans. Silk 3 rpt | 1.86E+09 | 36 | 2.68E+08 | 5.31E+05 |
| Bombyx Silk | 7.99E+08 | 14 | 8.40E+07 | 1.68E+05 |

Figure 24A:
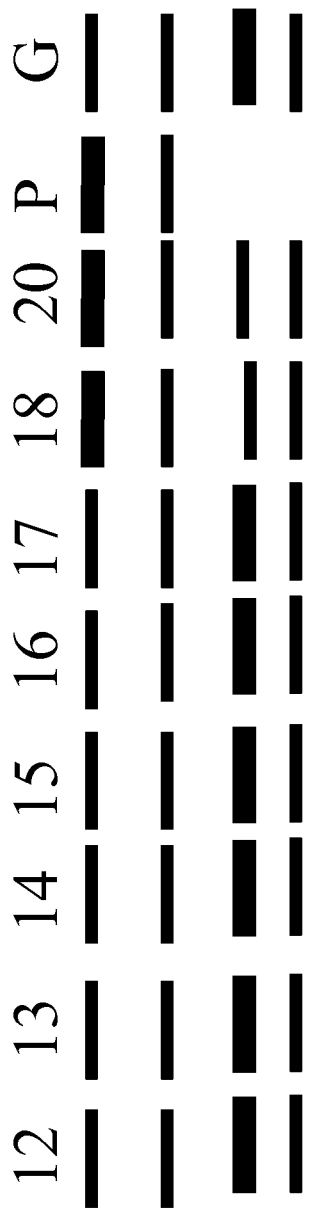
FIGS. 24A and 24B shows a schematic representation of the results of a PCR of DNA extracts from second generation egg masses transformed with a plasmid containing a 5'-$I_2$-3' insert (i.e., SEQ ID NO: 32). The DNA from about 75 eggs from each mating was pooled and PCR conducted using a primer internal to the 3' non-repetitive section of the native silkworm heavy fibroin gene, and a primer specific to either the synthetic spider silk derived internal repetitive region (i.e., spider silk analog) (FIG. 24A) or a primer specific to the native silkworm heavy fibroin gene (FIG. 24B). The PCR products from random samples (14-18, 20) were compared to PCR products generated with DNA corresponding to the plasmid with the silkworm/spider silk gene of SEQ ID NO: 32 (P) and to *Bombyx mori* genomic DNA (G).
Figure 24B:
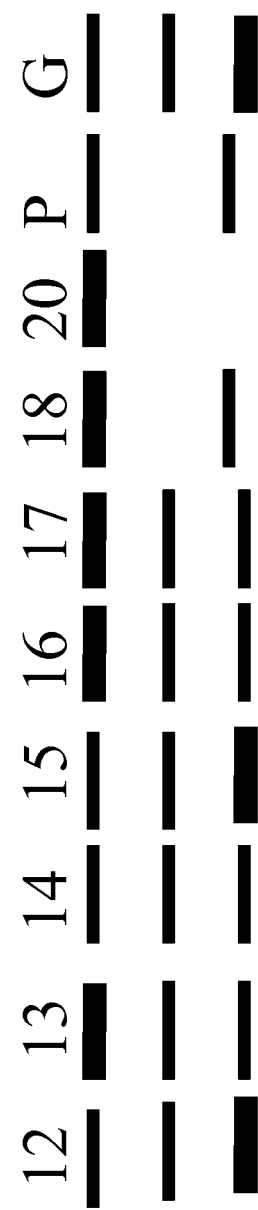

Also, FIG. 24 shows a schematic representation of the results of a PCR of DNA extracts from a portion of some of the second generation egg masses transformed with a pUC-plasmid containing a 5'4$^2$-3' insert (i.e., SEQ ID NO: 32). In these experiments, the DNA from about 75 second generation eggs (25% of the total) from individual matings (i.e., each sample corresponds to a different male-female mating) was pooled and PCR conducted using a primer internal to the 3' non-repetitive section of the native silkworm heavy fibroin gene, and either a primer specific to either the synthetic spider silk derived internal repetitive region (i.e., spider silk analog) (Panel A) or a primer specific to the native silkworm heavy fibroin gene (Panel B). The PCR products from random samples (14-18, and 20) were compared to PCR products generated with DNA corresponding to the plasmid with the silkworm/spider silk gene (P) and *Bombyx mori* genomic DNA (G). It can be seen that samples 18 and 20 show a pattern distinct from both genomic DNA and plasmid DNA indicating successful integration of the silkworm silk/spider silk construct into the silkworm genome.

Example 5—Other Silk Producing Moths

The same process can be used in any silk producing Lepidoptera. *Bombyx mandarina*, the wild form of the common silkworm, has essentially identical 5' and 3' regions on the fibroin genes, and can be transformed using the same reagents constructed to transform *Bombyx mori*. The other Saturniids are also capable of being transformed using this technique, in particular the species in the genera *Antherae* which are also used for silk production. For example to transform *Antheraea peryni*, the Chinese Oak Silkmoth, the 5' and 3' homologous end segments could be changed to the sequences in FIGS. 7 and 8. To transform *Antheraea yamamai*, the Japanese Oak Silkmoth, the sequences in FIGS. 9 and 10 may be used. Similarly, the sequences for light chain fibroin may be inserted into a vector comprising silkworm 5' and 3' sequences (e.g., SEQ ID NOS: 20 and 22) shown as FIGS. 11 and 12. The internal repeat sequences and gene assembly could be the same as the process described above.

The general technique for transforming the Saturniids is to obtain the sequence of the fibroin, typically through cDNA sequencing, and use approximately 500 (range 200-2000) or more base pairs from the 5' and 3' end along with an internal repeat segment to construct the artificial fibroin gene used for homologous recombination.

All patents, publications and abstracts cited above are incorporated herein by reference in their entirety. It should be understood that the foregoing relates only to certain embodiments of the present invention and that numerous modifications or alterations may be made therein without departing from the spirit and the scope of the present invention as defined in the following claims.

That which is claimed is:

1. A method of making a transgenic silkworm that produces a silk comprising a spider silk polypeptide, or an analog of a spider silk polypeptide:
   a) providing a silkworm, wherein the silkworm is *Bombyx mori, Bombyx mandarina, Antheraea peryni,* or *Antheraea yamamai;*
   b) transforming the silkworm of step (a) by inserting a nucleic acid sequence encoding a spider silk fibroin polypeptide, or an analog of a spider silk fibroin polypeptide, into the genome of the silkworm, wherein the nucleic acid comprises at least 2800 nucleotides encoding alternating beta-sheet domains and alpha-helix domains, wherein the amino acid sequence of the beta-sheet domains are each at least 60% identical to at least one of the beta-sheet domains as set forth in SEQ ID NO: 2, and wherein expression of the native silkworm fibroin gene is reduced; and
   c) selecting for a transgenic silkworm from step (b) that produces a silk that is at least 50% stronger than native silkworm silk.

2. The method of claim 1, wherein the silkworm is *Bombyx mori* or *Bombyx mandarina.*

3. The method of claim 1, wherein the silkworm is *Antheraea peryni* or *Antheraea yamamai.*

4. The method of claim 1, wherein the analog of the spider silk fibroin polypeptide comprises about 30 to 1000 spider silk beta-sheet domains alternating with about 30 to 1000 spider silk alpha helix domains.

5. The method of claim 1, wherein the nucleic acid sequence encoding the analog of the spider silk fibroin polypeptide encodes a polypeptide comprising the amino acid sequence as set forth in at least one of SEQ ID NO: 36, SEQ ID NO: 37, SEQ ID NO: 38, SEQ ID NO: 39, SEQ ID NO: 40, or SEQ ID NO: 41.

6. The method of claim 1, wherein the nucleic acid sequence encoding the analog of the spider silk fibroin polypeptide comprises the amino acid sequence as set forth in SEQ ID NO:2.

7. The method of claim 1, wherein the nucleic acid sequence encoding the analog of the spider silk fibroin polypeptide further comprises a reporter gene.

8. The method of claim 1, wherein the transgenic silkworm produces a silk that is at least 40% more elastic than native silkworm silk.

9. The method of claim 1, wherein the method is used to produce a first population of transformed silkworms by transforming a first set of silkworms with a first nucleic acid sequence encoding a first spider silk fibroin polypeptide, or an analog of the first spider silk fibroin polypeptide, and wherein the method is used to produce a second population of silkworms by transforming a second set of silkworms with a second nucleic acid sequence encoding a second spider silk fibroin polypeptide, or an analog of the second spider silk fibroin polypeptide.

10. The method of claim 9, further comprising breeding at least one of the transformed silkworms from each of the first and second populations to generate silkworms heterozygous for the first and second spider silk polypeptides and/or analogs thereof.

11. A transgenic silkworm transformed with an isolated nucleic acid that encodes a spider silk fibroin polypeptide or an analog of a spider silk fibroin polypeptide, wherein the analog of the spider silk fibroin polypeptide is encoded by at least 2800 nucleotides encoding alternating beta-sheet domains and alpha-helix domains, wherein the amino acid sequence of the beta-sheet domains are each at least 60% identical to at least one of the beta-sheet domains as set forth in SEQ ID NO: 2, wherein the transgenic silkworm produces a silk that is at least 50% stronger than native silkworm silk, and wherein the silkworm is *Bombyx mori, Bombyx mandarina, Antheraea peryni*, or *Antheraea yamamai*.

12. A silk produced by the transgenic silkworm of claim 11, wherein the silk is at least 50% stronger than native silkworm silk.

\* \* \* \* \*

SEQUENCE LISTING

```
<160> NUMBER OF SEQ ID NOS: 41

<210> SEQ ID NO 1
<211> LENGTH: 948
<212> TYPE: DNA
<213> ORGANISM: Artificial Sequence
<220> FEATURE:
<223> OTHER INFORMATION: Chemically Synthesized

<400> SEQUENCE: 1
tccggattgg ggggtcaggg tgctgctgct gctgcagccg ctgctgcggg aggtgggggt      60 caaggggag gatatggagg attagggtcg caggctggaa gaggaggagg aagcggacga     120
ggaggattag gaggacaagg agctgctgct gctgcagccg ctgctgctgg aggaggcgga     180
caaggtgggt taggaggtca aggtgctgcg gctgctgctg ctgctgctgc tggaggagga     240
ggacaaggcg gaggatatgg gggtttagga agtcaggcag gaagaggagg aggggggaaga     300 ggaggattgg ggggacaagg agctgctgct gctgcagccg ctgctgctgg aggaggaggt     360
cagggaggag gatatggtgg attaggaagc caagctggaa ggggaggatt aggaggacag     420
ggtgctgcag ctgctgctgc ggccgcggct ggaggggggg gtcaggagg tggatatgga     480
```
ggattaggat cacaagctgg aagaggagga ttaggaggac agggagctgc tgcagctgct    540
gccgctgctg ctggaggagg aggacaaggt ggaggatacg gtgggttggg gagtcaagca    600
ggtagaggag gaggttatgg aggattggga agtcaagctg gaagaggggg aggtagtggt    660
cgaggaggag gaggacaagg tgcggctgct gcggccgcgg ctgctgcagg tggaggaggt    720
cagggaggat taggaggtca gggtggagga cagggaggtc aaggtgctgc tgcagccgct    780
gcagccgctg ctggaggggg aggtcaggga ggtggttatg gaggtttagg aagtcaagca    840
ggaagagggg gattaggtgg tcaaggagct gctgctgctg ctgctgccgc agcgggtgga    900
ggagggcaag gtggaagtca ggcaggtaga ggagggttag gtcccggg    948

<210> SEQ ID NO 2
<211> LENGTH: 316
<212> TYPE: PRT
<213> ORGANISM: Artificial Sequence
<220> FEATURE:
<223> OTHER INFORMATION: Chemically Synthesized

<400> SEQUENCE: 2

Ser Gly Leu Gly Gly Gln Gly Ala Ala Ala Ala Ala Ala Ala Ala Ala
1               5                   10                  15

Gly Gly Gly Gly Gln Gly Gly Gly Tyr Gly Gly Leu Gly Ser Gln Ala
            20                  25                  30

Gly Arg Gly Gly Ser Gly Arg Gly Gly Leu Gly Gly Gln Gly Ala
        35                  40                  45

Ala Ala Ala Ala Ala Ala Ala Gly Gly Gly Gln Gly Gly Leu
    50                  55                  60

Gly Gly Gln Gly Ala Ala Ala Ala Ala Ala Ala Ala Gly Gly Gly
65                  70                  75                  80

Gly Gln Gly Gly Gly Tyr Gly Gly Leu Gly Ser Gln Ala Gly Arg Gly
                85                  90                  95

Gly Gly Arg Gly Gly Leu Gly Gly Gln Gly Ala Ala Ala Ala Ala
            100                 105                 110

Ala Ala Ala Ala Gly Gly Gly Gly Gln Gly Gly Gly Tyr Gly Gly Leu
    115                 120                 125

Gly Ser Gln Ala Gly Arg Gly Gly Leu Gly Gly Gln Gly Ala Ala Ala
    130                 135                 140

Ala Ala Ala Ala Ala Ala Gly Gly Gly Gly Gln Gly Gly Gly Tyr Gly
145                 150                 155                 160

Gly Leu Gly Ser Gln Ala Gly Arg Gly Gly Leu Gly Gly Gln Gly Ala
                165                 170                 175

Ala Ala Ala Ala Ala Ala Ala Gly Gly Gly Gly Gln Gly Gly Gly
            180                 185                 190

Tyr Gly Gly Leu Gly Ser Gln Ala Gly Arg Gly Gly Tyr Gly Gly
        195                 200                 205

Leu Gly Ser Gln Ser Gly Arg Gly Gly Gly Ser Gly Arg Gly Gly Gly
    210                 215                 220

Gly Gln Gly Ala Ala Ala Ala Ala Ala Ala Ala Gly Gly Gly Gly
225                 230                 235                 240

Gln Gly Gly Leu Gly Gly Gln Gly Gly Gln Gly Gly Gln Gly Ala
                245                 250                 255

Ala Ala Ala Ala Ala Ala Ala Gly Gly Gly Gly Gln Gly Gly Gly
            260                 265                 270

Tyr Gly Gly Leu Gly Ser Gln Ala Gly Arg Gly Gly Leu Gly Gly Gln

```
                275                 280                 285
Gly Ala Ala Ala Ala Ala Ala Ala Ala Gly Gly Gly Gln Gly
    290                 295                 300

Gly Ser Gln Ala Gly Arg Gly Gly Leu Gly Pro Gly
305                 310                 315

<210> SEQ ID NO 3
<211> LENGTH: 126
<212> TYPE: DNA
<213> ORGANISM: Artificial Sequence
<220> FEATURE:
<223> OTHER INFORMATION: Chemically Synthesized

<400> SEQUENCE: 3
tccggattgg ggggtcaggg tgctggtgct gctgcagccg ctgctgcggg aggtgcgggt      60
caatccggat tgggggggtca gggtgctgct gctgctgcag ccgctgctgc gggaggtggg    120
ggtcaa                                                               126

<210> SEQ ID NO 4
<211> LENGTH: 42
<212> TYPE: PRT
<213> ORGANISM: Artificial Sequence
<220> FEATURE:
<223> OTHER INFORMATION: Chemically Synthesized

<400> SEQUENCE: 4

Ser Gly Leu Gly Gly Gln Gly Ala Gly Ala Ala Ala Ala Ala Ala
1               5                  10                  15

Gly Gly Ala Gly Gln Ser Gly Leu Gly Gln Gly Ala Ala Ala Ala
            20                  25                  30

Ala Ala Ala Ala Ala Gly Gly Gly Gly Gln
            35                  40

<210> SEQ ID NO 5
<211> LENGTH: 1051
<212> TYPE: DNA
<213> ORGANISM: Artificial Sequence
<220> FEATURE:
<223> OTHER INFORMATION: Chemically Synthesized

<400> SEQUENCE: 5
atgagagtca aaacctttgt gatcttggtc tgcgctctgc aggtgagtta attatttttac     60 tattatttca gaaggtggcc agacgatatc acgggccacc tgataataag tggtcgccaa    120
aacgcacaga tatcgtaaat tgtgccattt gatttgtcac gccctggggg gctacggaat    180
aaactacatt tatttattta aaaaatgaac cttagattat gtaacttgtg atttatttgc    240
gtcaaaagta ggcaagatga atctatgtaa atactgggca gacttgcaat atcctatttc    300
accggtaaaa tcagcattgc aatatgcaat gctaaattca acaatatgta aaacaattcg    360
taaagcatca ttagaaaata gacgaaagaa attgcataaa attataaccg cattattaat    420
ttattatgat atctattaac aattgctatt gcctttttt cgcaaattat aatcattttc     480
ataacctcga ggtagcattc tgtacatttt aatacattgg tatgtgatta aacacgagc     540 tgcccactga gtttctcgcc agatcttctc agtgggtcgc gttaccgatc acgtgataga    600
ttctatgaag cactgctctt gttagggcta gtgttagtaa attctttcag gttgagtctg    660
agagctcacc tacccatcgg agcgtagctg aataggcta ccagctggta ggtagggaaa     720
caaagctcga aacaagctca agtaataaca acataatgtg accataaaat ctcgtggtgt    780
```

```
atgagataca attatgtact ttcccacaaa tgtttacata attagaatgt tgttcaactt        840
gcctaacgcc ccagctagaa cattcaatta ttactattac cactactaag gcagtatgtc        900
ctaactcgtt ccagatcagc gctaacttcg attgaatgtg cgaaatttat agctcaatat        960
tttagcactt atcgtattga tttaagaaaa aattgttaac attttgtttc agtatgtcgc       1020
ttatacaaat gcaaacatca atgattccgg a                                      1051
```

<210> SEQ ID NO 6
<211> LENGTH: 14
<212> TYPE: PRT
<213> ORGANISM: Bombyx mori

<400> SEQUENCE: 6

Met Arg Val Lys Thr Phe Val Ile Leu Val Cys Ala Leu Gln
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 7

Tyr Val Ala Tyr Thr Asn Ala Asn Ile Asn Asp Phe Asp
1               5                   10

<210> SEQ ID NO 8
<211> LENGTH: 786
<212> TYPE: DNA
<213> ORGANISM: Artificial Sequence
<220> FEATURE:
<223> OTHER INFORMATION: Chemically Synthesized

<400> SEQUENCE: 8

```
cccggggtgt catctgcttc atctcgcagt tacgactatt ctcgtcgtaa cgtccgcaaa         60
aactgtggaa ttcctagaag acaactagtt gttaaattca gagcactgcc ttgtgtgaat        120
tgctaatttt taatataaaa taaccccttgt ttcttacttc gtcctggata catctatgtt       180
ttttttttcg ttaataaatg agagcattta agttattgtt tttaattact tttttttaga       240
aaacagattt cggattttttt gtatgcattt tatttgaatg tactaatata atcaattaat       300
caatgaattc atttatttaa gggataacaa taatccatga attcacatgc acatttaaaa       360
caaaactaaa ttacaatagg ttcatataaa acaacaagt atgccttctc aactaagaat        420
actatattgt ttaaaccgta aaaaagtca tatttctgta tatcaaaaca catctaatat        480
taaaaaaaca gtcagcaagc acttacaagt gtgggctcgg acagcaatta cctggtctca       540
ggagacactt gaagaacgag aagcacgtct ctctgtcgat tgcgaggctc atgcactatc       600
gcttgagtct gagaccttta ctgataggga aatccgtttg agctctcaga gggttcggac       660
agcaaaagct tgcccggtct caggagacat tagaagaacg ggaagcataa ctcaataccg       720
atcgcgtttc cattgagcct atgcttcgtg ataataataa ataaagccca aggtcagacg       780
ctaaaa                                                                  786
```

<210> SEQ ID NO 9
<211> LENGTH: 41
<212> TYPE: PRT
<213> ORGANISM: Artificial Sequence
<220> FEATURE:
<223> OTHER INFORMATION: Chemically Synthesized

<400> SEQUENCE: 9

Pro Gly Val Ser Ser Ala Ser Ser Arg Ser Tyr Asp Tyr Ser Arg Arg
1               5                   10                  15

Asn Val Arg Lys Asn Cys Gly Ile Pro Arg Arg Gln Leu Val Val Lys
            20                  25                  30

Phe Arg Ala Leu Pro Cys Val Asn Cys
            35                  40

<210> SEQ ID NO 10
<211> LENGTH: 636
<212> TYPE: DNA
<213> ORGANISM: Artificial Sequence
<220> FEATURE:
<223> OTHER INFORMATION: Chemically Synthesized

<400> SEQUENCE: 10
atgagagtaa tagccttcgt gatcttgtgc tgcgctttgc aggtgagttc caacatttat      60
ttaaatattt tcataatatg caaatgttcc acacgcttat aattttaaat aattattttt     120
taatggtgaa aataaagcaa tataaatttc aattacttac agtatgcaac tgctaaaaat     180
ttacgtcacc acgacgaata cgtagacaat catgggcaat tagtcgaacg attcacaacc     240
cgtaaacatt ttgaaaggaa cgctgcaacg cgcccacatc tttctggtaa tgaacgatta     300
gtcgagacta ttgtcctcga agaggatccg tatggtcatg aagatatcta cgaagaagat     360
gttgttatca agagagtacc aggggctagt tctagcgctg ctgcagcgtc tagtgccagc     420
gccgggtcag gacaaactat tatagttgaa agacaggctt acatggtgc aggcggtgcc      480 gcaggagctg cagcgggagc cgcagctggc tcaagtgcca gacgaggcgg tggattttac     540
gaaacacata tagttacag cagttacgga tcaggctcat catcagcagc agccggctca      600
ggtgctggag gagtaggcgg tggttatgga tccgga                                636

<210> SEQ ID NO 11
<211> LENGTH: 14
<212> TYPE: PRT
<213> ORGANISM: Antheraea pernyi

<400> SEQUENCE: 11

Met Arg Val Ile Ala Phe Val Ile Leu Cys Cys Ala Leu Gln
1               5                   10

<210> SEQ ID NO 12
<211> LENGTH: 158
<212> TYPE: PRT
<213> ORGANISM: Artificial Sequence
<220> FEATURE:
<223> OTHER INFORMATION: Chemically Synthesized

<400> SEQUENCE: 12

Tyr Ala Thr Ala Lys Asn Leu Arg His His Asp Glu Tyr Val Asp Asn
1               5                   10                  15

His Gly Gln Leu Val Glu Arg Phe Thr Thr Arg Lys His Phe Glu Arg
            20                  25                  30

Asn Ala Ala Thr Arg Pro His Leu Ser Gly Asn Glu Arg Leu Val Glu
        35                  40                  45

Thr Ile Val Leu Glu Glu Asp Pro Tyr Gly His Glu Asp Ile Tyr Glu
    50                  55                  60

Glu Asp Val Val Ile Lys Arg Val Pro Gly Ala Ser Ser Ser Ala Ala
65                  70                  75                  80

```
Ala Ala Ser Ser Ala Ser Ala Gly Ser Gly Gln Thr Ile Ile Val Glu
                85                  90                  95

Arg Gln Ala Ser His Gly Ala Gly Gly Ala Ala Ala Ala Ala Ala Gly
            100                 105                 110

Ala Ala Ala Gly Ser Ser Ala Arg Arg Gly Gly Gly Phe Tyr Glu Thr
            115                 120                 125

His Asn Ser Tyr Ser Ser Tyr Gly Ser Gly Ser Ser Ala Ala Ala
    130                 135                 140

Gly Ser Gly Ala Gly Gly Val Gly Gly Gly Tyr Gly Ser Gly
145                 150                 155
```

<210> SEQ ID NO 13
<211> LENGTH: 636
<212> TYPE: DNA
<213> ORGANISM: Artificial Sequence
<220> FEATURE:
<223> OTHER INFORMATION: Chemically Synthesized

<400> SEQUENCE: 13

```
cccgggggtt tcggacgagg tgacggtggt tatggttcag gctcatcggc agcagcagca    60
gcggcggcgg cggcggcggc tgcaagacga gcaggtcacg gacgttctgc aggaagtgca   120
gcagcagcag cagcagctgc agctgcagcg gctgcctcag gtgctggtgg atcaggcggt   180
agttatggat gggactatga agttacggt tctggctcag cggcagcagc agctggctca    240
ggtgctggag gatcaggcgg tggttatgga tggggtgacg gcggttatgg ttcaggttct   300
tctgcggcag cagcagcagc agcggcggcg cggcaggat caagacgctc agggcatgat    360
cgtgcatatg gagcaggaag tgctgcagcc gcagcagcag cagctgccgc tggcgcaggg   420
gctagtcgac aagtcggaat ttatggaaca gacgatggct tcgtattaga tggaggttac    480
gattcagagg gatcagcggc ggcggcggca gcggcagcag cagctgcggc gtcatcaagt    540
ggtagatcta ctgaaggtca tccacttctt tcgatatgct gcaggccgtg ttctcacagt   600
catagctatg aagcttccag aatttccgtc cactaa                              636
```

<210> SEQ ID NO 14
<211> LENGTH: 211
<212> TYPE: PRT
<213> ORGANISM: Artificial Sequence
<220> FEATURE:
<223> OTHER INFORMATION: Chemically Synthesized

<400> SEQUENCE: 14

```
Pro Gly Gly Phe Gly Arg Gly Asp Gly Gly Tyr Gly Ser Gly Ser Ser
1               5                   10                  15

Ala Ala Ala Ala Ala Ala Ala Ala Ala Ala Ala Arg Arg Ala Gly
            20                  25                  30

His Gly Arg Ser Ala Gly Ser Ala Ala Ala Ala Ala Ala Ala Ala
            35                  40                  45

Ala Ala Ala Ser Gly Ala Gly Gly Ser Gly Gly Ser Tyr Gly Trp
        50                  55                  60

Asp Tyr Glu Ser Tyr Gly Ser Gly Ser Ala Ala Ala Ala Gly Ser
65                  70                  75                  80

Gly Ala Gly Gly Ser Gly Gly Gly Tyr Gly Trp Gly Asp Gly Gly Tyr
                85                  90                  95

Gly Ser Gly Ser Ser Ala Ala Ala Ala Ala Ala Ala Ala Ala Ala
            100                 105                 110
```

Gly Ser Arg Arg Ser Gly His Asp Arg Ala Tyr Ala Gly Ser Ala
            115                 120                 125

Ala Ala Ala Ala Ala Ala Ala Gly Ala Gly Ala Ser Arg Gln
        130                 135                 140

Val Gly Ile Tyr Gly Thr Asp Asp Gly Phe Val Leu Asp Gly Tyr
145                 150                 155                 160

Asp Ser Glu Gly Ser Ala Ala Ala Ala Ala Ala Ala Ala Ala
                165                 170                 175

Ala Ser Ser Ser Gly Arg Ser Thr Glu Gly His Pro Leu Leu Ser Ile
            180                 185                 190

Cys Cys Arg Pro Cys Ser His Ser His Ser Tyr Glu Ala Ser Arg Ile
            195                 200                 205

Ser Val His
    210

<210> SEQ ID NO 15
<211> LENGTH: 615
<212> TYPE: DNA
<213> ORGANISM: Artificial Sequence
<220> FEATURE:
<223> OTHER INFORMATION: Chemically Synthesized

<400> SEQUENCE: 15
atgagagtaa cagccttcgt gatcttgtgc tgcgctttgc aggtgagttc caacatttat      60
ttaaataatt tcatggaata atataataat aaataaaaaa ataaataata ataatattgc     120
atacacttat aatttttaaat aattattttt taactgggaa ataaaagcaa tataaaatttc    180 aattacttac agtatgcaac tgctaataat ttacatcacc acgacgaata tgtagataat     240
catgggcaat tagtcgaaag attcacaacc cgtaaacatt atgaaggaa cgccgcaacg      300 cgtccacatc tttctggtaa tgaacgatta gtcgagacta ttgtcctcga agaggatccg     360
tatggtcatg aagatatcta cgaagaagat gttgttatca atagagtacc aggggccagt    420
tctagcgctg ctgcagcgtc tagtgccagc gccgggtcag acaaactat tatagttgaa     480 agacaggctt cacatggagc aggaggtgct gcaggcgctg cagcgggagc tgcagctggc     540
tcaagtgcca gaggaggaag tggattttac gaaacacacg atagttatag cagttacgga    600
tcaggctcgt ccgga                                                     615

<210> SEQ ID NO 16
<211> LENGTH: 14
<212> TYPE: PRT
<213> ORGANISM: Antheraea yamamai

<400> SEQUENCE: 16

Met Arg Val Thr Ala Phe Val Ile Leu Cys Cys Ala Leu Gln
1               5                   10

<210> SEQ ID NO 17
<211> LENGTH: 141
<212> TYPE: PRT
<213> ORGANISM: Artificial Sequence
<220> FEATURE:
<223> OTHER INFORMATION: Chemically Synthesized

<400> SEQUENCE: 17

Tyr Ala Thr Ala Asn Asn Leu His His His Asp Glu Tyr Val Asp Asn
1               5                   10                  15

His Gly Gln Leu Val Glu Arg Phe Thr Thr Arg Lys His Tyr Glu Arg
            20                  25                  30

```
Asn Ala Ala Thr Arg Pro His Leu Ser Gly Asn Glu Arg Leu Val Glu
            35                   40                  45

Thr Ile Val Leu Glu Glu Asp Pro Tyr Gly His Glu Asp Ile Tyr Glu
        50                  55                  60

Glu Asp Val Val Ile Asn Arg Val Pro Gly Ala Ser Ser Ser Ala Ala
65                  70                  75                  80

Ala Ala Ser Ser Ala Ser Ala Gly Ser Gly Gln Thr Ile Ile Val Glu
                85                  90                  95

Arg Gln Ala Ser His Gly Ala Gly Gly Ala Ala Gly Ala Ala Ala Gly
            100                 105                 110

Ala Ala Ala Gly Ser Ser Ala Arg Gly Gly Ser Gly Phe Tyr Glu Thr
            115                 120                 125

His Asp Ser Tyr Ser Ser Tyr Gly Ser Gly Ser Ser Gly
            130                 135                 140
```

```
<210> SEQ ID NO 18
<211> LENGTH: 615
<212> TYPE: DNA
<213> ORGANISM: Artificial Sequence
<220> FEATURE:
<223> OTHER INFORMATION: Chemically Synthesized

<400> SEQUENCE: 18
cccggggcag cagccggctc cggtgctgga ggacgaggcg acggcggtta tggttcaggc    60
tcttcggcag cagcagcagc ggcagcggca gcagcggctg caagacgagc gggccatgac   120
catgctgctg gaagttcagg cggtggttat agctgggatt atagtagtta tggttcagaa   180
tcagcggcag cagcagcagc agcagcagca gcaggctcag gtgctggagg agtaggtgga   240
ggttacggag gaggtgacgg tggttatggt tcaggatctt ctgcggcagc agcagcagca   300
gcggcggcag cagcagcgtc aagacgcgca gggcatgatc gtgcatatgg agctggaagt   360
gctgcagccg cagcagcagc agctgccgct ggcgcaggtg ctagtcgacc agtcggaatt   420
tacggaacag acgatggctt cgtattagat ggcggttacg attcagaggg atcagcggcg   480
gcggcggcag cagcagcggc agctgcggcg tcatcaagtg gtagatctac tgaaggtcat   540
ccacttcttt cgatatgctg caggccgtgt tctcacagac atagctatga agcttccaga   600
atttccgtcc actaa                                                    615
```

```
<210> SEQ ID NO 19
<211> LENGTH: 204
<212> TYPE: PRT
<213> ORGANISM: Artificial Sequence
<220> FEATURE:
<223> OTHER INFORMATION: Chemically Synthesized

<400> SEQUENCE: 19

Pro Gly Ala Ala Ala Gly Ser Gly Ala Gly Gly Arg Gly Asp Gly Gly
1               5                   10                  15

Tyr Gly Ser Gly Ser Ser Ala Ala Ala Ala Ala Ala Ala Ala Ala Ala
                20                  25                  30

Ala Ala Arg Arg Ala Gly His Asp Arg Ala Ala Gly Ser Ser Gly Gly
            35                  40                  45

Gly Tyr Ser Trp Asp Tyr Ser Ser Tyr Gly Ser Glu Ser Ala Ala Ala
        50                  55                  60

Ala Ala Ala Ala Ala Ala Ala Gly Ser Gly Ala Gly Gly Val Gly Gly
65                  70                  75                  80
```

```
Gly Tyr Gly Gly Gly Asp Gly Tyr Ser Gly Ser Ser Ala Ala
                85                  90                  95

Ala Ala Ala Ala Ala Ala Ala Ala Ala Ser Arg Arg Ala Gly His
            100                 105                 110

Asp Arg Ala Tyr Gly Ala Gly Ser Ala Ala Ala Ala Ala Ala
            115                 120                 125

Ala Ala Gly Ala Gly Ala Ser Arg Pro Val Gly Ile Tyr Gly Thr Asp
            130                 135                 140

Asp Gly Phe Val Leu Asp Gly Gly Tyr Asp Ser Glu Gly Ser Ala Ala
145                 150                 155                 160

Ala Ala Ala Ala Ala Ala Ala Ala Ala Ser Ser Ser Gly Arg Ser
                165                 170                 175

Thr Glu Gly His Pro Leu Leu Ser Ile Cys Cys Arg Pro Cys Ser His
            180                 185                 190

Arg His Ser Tyr Glu Ala Ser Arg Ile Ser Val His
            195                 200
```

<210> SEQ ID NO 20
<211> LENGTH: 570
<212> TYPE: DNA
<213> ORGANISM: Artificial Sequence
<220> FEATURE:
<223> OTHER INFORMATION: Chemically Synthesized

<400> SEQUENCE: 20

```
tgcgcgcgca tcgtaaaact tcactctcat agattttca taacgcgcct aaagaagtat    60
aacttcaata atttaaattt aaaaaaaaac atgcatagaa taattatatg aattatttaa   120
aatgtcattt accgacattg acataacaga cgacgttaac actacaaaac attttaattc   180
cacattgtta catattcaac agttaaattt gcgttaattc tcgatgcgaa caaatataag   240
aacaatcgga tcaattagat cgctttgttt cgaacaacac ttagtttaac tagaggcgta   300
cacctcaaga aatcatcttc attagaaact aaaccttaaa atcgcaataa taaagcatag   360
tcaattttaa ctgaaatgca agtctttttg aacgttagat gctgtcagcg ttcgttggta   420
cagttgtttg atatttatt taattgtctt tttatatata aatagtggaa cattaatcac   480
ggaatcctgt atagtatata ccgattggtc acataacaga ccactaaaat gaagcctata   540
tttttggtat tactcgtcgc tacatccgga                                    570
```

<210> SEQ ID NO 21
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 21

```
Met Lys Pro Ile Phe Leu Val Leu Leu Val Ala Thr Ser Gly
1               5                   10
```

<210> SEQ ID NO 22
<211> LENGTH: 572
<212> TYPE: DNA
<213> ORGANISM: Artificial Sequence
<220> FEATURE:
<223> OTHER INFORMATION: Chemically Synthesized

<400> SEQUENCE: 22

```
cccgggctcc tgagaggcgt tggcaacggt aatgacgcga ccggcttagt tgctaatgct    60
```

| | |
|---|---|
| caaagatata ttgcacaagc agccagccag gttcacgtct aaataagaac tgtaaataat | 120 |
| gtatatatat aattatataa aagatatata taaccatata caaacatata tatcattata | 180 |
| agacaatcta cctatataaa aacagactaa aattaataat tatgtatact ttaattgtgt | 240 |
| ttaggacatt ttatgcaaat tgtgtttgcg ttaggatttt ttttggaagt tttttagatt | 300 |
| atttatgaat atataaataa atatacgtta atataatata tattatataa atcaacgaca | 360 |
| cggcttttca ttttggtgat gatcaatctt attgttcttc taattgattt ttttgtacaa | 420 |
| taaagatgta tccagttttc cagataaaga atttagtttg ttatttctgg ccccattaaa | 480 |
| ataagtacgg tattcgacaa taccacatag tatatacccca agacggtgg attggacagt | 540 |
| gggtacatgg atttcggtac tgttgtcatg ct | 572 |

<210> SEQ ID NO 23
<211> LENGTH: 33
<212> TYPE: PRT
<213> ORGANISM: Artificial Sequence
<220> FEATURE:
<223> OTHER INFORMATION: Chemically Synthesized

<400> SEQUENCE: 23

Pro Gly Leu Leu Arg Gly Val Gly Asn Gly Asn Asp Ala Thr Gly Leu
1               5                   10                  15

Val Ala Asn Ala Gln Arg Tyr Ile Ala Gln Ala Ala Ser Gln Val His
            20                  25                  30

Val

<210> SEQ ID NO 24
<211> LENGTH: 1177
<212> TYPE: DNA
<213> ORGANISM: Artificial Sequence
<220> FEATURE:
<223> OTHER INFORMATION: Chemically Synthesized

<400> SEQUENCE: 24

| | |
|---|---|
| ctcgagctca acgagccatg aataaattag aaatcaatta ataacataaa ataggcaaac | 60 |
| aaaataaaac catttacata gagaacgttt gttgaacaaa aacaataact tgtatacatt | 120 |
| gtttgcacaa atgtttgaag cgaaaattta ttactctcta cgtaagcttg atcaaacttc | 180 |
| gttttcgtat aaaacgcgtt ggcccaagca ctttggcata gtcgtcttat catcgggtct | 240 |
| ctaaggatca aacgatccaa agaccgccaa atggtgagca agggcgagga gctgttcacc | 300 |
| ggggtggtgc ccatcctggt cgagctggac ggcgacgtaa acggccacaa gttcagcgtg | 360 |
| tccggcgagg gcgagggcga tgccacctac ggcaagctga ccctgaagtt catctgcacc | 420 |
| accggcaagc tgcccgtgcc ctggcccacc ctcgtgacca ccctcaccta cggcgtgcag | 480 |
| tgcttcagcc gctaccccga ccacatgaag cagcacgact tcttcaagtc cgccatgccc | 540 |
| gaaggctacg tccaggagcg caccatcttc ttcaaggacg acggcaacta caagacccgc | 600 |
| gccgaggtga agttcgaggg cgacaccctg gtgaaccgca tcgagctgaa gggcatcgac | 660 |
| ttcaaggagg acggcaacat cctggggcac aagctggagt acaactacaa cagccacaac | 720 |
| gtctatatca tggccgacaa gcagaagaac ggcatcaagg tgaacttcaa gatccgccac | 780 |
| aacatcgagg acggcagcgt gcagctcgcc gaccactacc agcagaacac ccccatcggc | 840 |
| gacggccccg tgctgctgcc cgacaaccac tacctgagca cccagtccgc cctgagcaaa | 900 |
| gaccccaacg agaagcgcga tcacatggtc ctgctggagt tcgtgaccgc cgccgggatc | 960 |
| actctcggca tggacgagct gtacaagtaa atacaacaaa caggagtatt ccttgtagtg | 1020 |

```
tttaagattt taaatcttac ttaatgactt cgaacgattt aacgataact ttctctttgt    1080
ttaactttaa tcagcataca taaaaagccc cggttttgta ccgggaagaa aaaaaatgta    1140
attgtgttgc ctagataata aacgtattat cagatct                             1177
```

<210> SEQ ID NO 25
<211> LENGTH: 239
<212> TYPE: PRT
<213> ORGANISM: Artificial Sequence
<220> FEATURE:
<223> OTHER INFORMATION: Chemically Synthesized

<400> SEQUENCE: 25

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235
```

<210> SEQ ID NO 26
<211> LENGTH: 1080
<212> TYPE: DNA
<213> ORGANISM: Artificial Sequence
<220> FEATURE:
<223> OTHER INFORMATION: Chemically Synthesized

<400> SEQUENCE: 26

```
atgagagtca aaacctttgt gatcttggtc taatagtgag taatagtgag taatagtgat      60
gcgctctgca ggtgagttaa ttattttact attattttcag aaggtggcca gacgatatca    120
cgggccacct gataataagt ggtcgccaaa acgcacagat atcgtaaatt gtgccatttg    180
atttgtcacg ccctgggggg ctacggaata aactacattt atttatttaa aaaatgaacc    240
```

-continued

```
ttagattatg taacttgtga tttatttgcg tcaaaagtag gcaagatgaa tctatgtaaa      300
tactgggcag acttgcaata tcctatttca ccggtaaaat cagcattgca atatgcaatg      360
ctaaattcaa caatatgtaa aacaattcgt aaagcatcat tagaaaatag acgaaagaaa      420
ttgcataaaa ttataaccgc attattaatt tattatgata tctattaaca attgctattg      480
cctttttttc gcaaattata atcattttca taacctcgag gtagcattct gtacatttta      540
atacattggt atgtgattat aacacgagct gcccactgaa tttctcgcca gatcttctca      600
gtgggtcgcg ttaccgatca cgtgatagat tctatgaagc actgctcttg ttagggctag      660
tgttagtaaa ttctttcagg ttgagtctga gagctcacct acccatcgga gcgtagctgg      720
aataggctac cagctggtag gtagggaaac aaagctcgaa acaagctcaa gtaataacaa      780
cataatgtga ccataaaatc tcgtggtgta tgagatacaa ttatgtactt tcccacaaat      840
gtttacataa ttagaatgtt gttcaacttg cctaacgccc cagctagaac attcaattat      900
tactattacc actactaagg cagtatgtcc taactcgttc cagatcagcg ctaacttcga      960
ttgaatgtgc gaaatttata gctcaatatt ttagcactta tcgtattgat ttaagaaaaa     1020
attgttaaca ttttgtttca gtatgtcgct tatacaaatg caaacatcaa tgattccgga     1080
```

<210> SEQ ID NO 27
<211> LENGTH: 10
<212> TYPE: PRT
<213> ORGANISM: Bombyx mori

<400> SEQUENCE: 27

Met Arg Val Lys Thr Phe Val Ile Leu Val
1               5                   10

<210> SEQ ID NO 28
<211> LENGTH: 4
<212> TYPE: PRT
<213> ORGANISM: Bombyx mori

<400> SEQUENCE: 28

Cys Ala Leu Gln
1

<210> SEQ ID NO 29
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 29

Tyr Val Ala Tyr Thr Asn Ala Asn Ile Asn Asp Phe Asp
1               5                   10

<210> SEQ ID NO 30
<211> LENGTH: 3029
<212> TYPE: DNA
<213> ORGANISM: Artificial Sequence
<220> FEATURE:
<223> OTHER INFORMATION: Chemically synthesized

<400> SEQUENCE: 30

```
atgagagtca aacctttgt gatcttggtc tgcgctctgc aggtgagtta attattttac       60
tattatttca gaaggtggcc agacgatatc acgggccacc tgataataag tggtcgccaa      120
aacgcacaga tatcgtaaat tgtgccattt gatttgtcac gccctggggg gctacggaat      180
```

```
aaactacatt tatttattta aaaaatgaac cttagattat gtaacttgtg atttatttgc    240
gtcaaaagta ggcaagatga atctatgtaa atactgggca gacttgcaat atcctatttc    300
accggtaaaa tcagcattgc aatatgcaat gctaaattca acaatatgta aaacaattcg    360
taaagcatca ttagaaaata gacgaaagaa attgcataaa attataaccg cattattaat    420
ttattatgat atctattaac aattgctatt gccttttttt cgcaaattat aatcattttc    480
ataacctcga ggtagcattc tgtacatttt aatacattgg tatgtgatta taacacgagc    540
tgcccactga gtttctcgcc agatcttctc agtgggtcgc gttaccgatc acgtgataga    600
ttctatgaag cactgctctt gttagggcta gtgttagtaa attctttcag gttgagtctg    660
agagctcacc tacccatcgg agcgtagctg aataggcta ccagctggta ggtagggaaa    720
caaagctcga aacaagctca agtaataaca acataatgtg accataaaat ctcgtggtgt    780
atgagataca attatgtact ttcccacaaa tgtttacata attagaatgt tgttcaactt    840
gcctaacgcc ccagctagaa cattcaatta ttactattac cactactaag gcagtatgtc    900
ctaactcgtt ccagatcagc gctaacttcg attgaatgtg cgaaatttat agctcaatat    960
tttagcactt atcgtattga tttaagaaaa aattgttaac attttgtttc agtatgtcgc   1020
ttatacaaat gcaaacatca atgattccgg attgggggt cagggtgctg ctgctgctgc   1080
agccgctgct gcgggaggtg ggggtcaagg gggaggatat ggaggattag gtcgcaggc   1140 tggaagagga ggaggaagcg gacgaggagg attaggagga caaggagctg ctgctgctgc   1200
agccgctgct gctggaggag gcggacaagg tgggttagga ggtcaaggtg ctgcggctgc   1260
tgctgctgct gctgctggag gaggaggaca aggcggagga tatgggggtt taggaagtca   1320
ggcaggaaga ggaggagggg gaagaggagg attgggggga caaggagctg ctgctgctgc   1380
agccgctgct gctggaggag gaggtcaggg aggaggatat ggtggattag gaagccaagc   1440
tggaagggga ggattaggag gacagggtgc tgcagctgct gctgcggccg cggctggagg   1500 gggggggtcag ggaggtggat atggaggatt aggatcacaa gctggaagag gaggattagg   1560
aggacaggga gctgctgcag ctgctgccgc tgctgctgga ggaggaggac aaggtggagg   1620
atacggtggg ttggggagtc aagcaggtag aggaggaggt tatggaggat tgggaagtca   1680
agctggaaga gggggaggta gtggtcgagg aggaggagga caaggtgcgg ctgctgcggc   1740
cgcggctgct gcaggtggag gaggtcaggg aggattagga ggtcagggtg gaggacaggg   1800
aggtcaaggt gctgctgcag ccgctgcagc cgctgctgga ggggaggtc agggaggtgg   1860 ttatggaggt ttaggaagtc aagcaggaag aggggattag gtggtcaag gagctgctgc   1920 tgctgctgct gccgcagcgg gtggaggagg gcaaggtgga agtcaggcag gtagaggagg   1980
gttaggtccc ggggtgtcat ctgcttcatc tcgcagttac gactattctc gtcgtaacgt   2040
ccgcaaaaac tgtggaattc ctagaagaca actagttgtt aaattcagag cactgccttg   2100
tgtgaattgc taattttta tataaaataa ccccttgtttc ttacttcgtc ctggatacat   2160
ctatgttttt tttttcgtta ataaatgaga gcatttaagt tattgttttt aattactttt   2220
ttttagaaaa cagatttcgg attttttgta tgcattttat ttgaatgtac taatataatc   2280
aattaatcaa tgaattcatt tatttaaggg ataacaataa tccatgaatt cacatgcaca   2340
tttaaaacaa aactaaatta caataggttc atataaaaac aacaagtatg ccttctcaac   2400
taagaatact atattgttta aaccgtaaaa aaagtcatat ttctgtatat caaaacacat   2460
ctaatattaa aaaaacagtc agcaagcact tacaagtgtg ggctcggaca gcaattacct   2520
```

| | |
|---|---|
| ggtctcagga gacacttgaa gaacgagaag cacgtctctc tgtcgattgc gaggctcatg | 2580 |
| cactatcgct tgagtctgag acctttactg atagggaaat ccgtttgagc tctcagaggg | 2640 |
| ttcggacagc aaaagcttgc ccggtctcag gagacattag aagaacggga agcataactc | 2700 |
| aataccgatc gcgtttccat tgagcctatg cttcgtgata ataataaata aagcccaagg | 2760 |
| tcagacgcta aaagaaagga gataggatcc aagcttggcg taatcatggt catagctgtt | 2820 |
| tcctgtgtga aattgttatc cgctcacaat tccacacaac atacgagccg aagcataaa | 2880 |
| gtgtaaagcc tggggtgcct aatgagtgag ctaactcaca ttaattgcgt tgcgctcact | 2940 |
| gcccgctttc cagtcgggaa acctgtcgtg ccagctgcat taatgaatcg gccaacgcgc | 3000 |
| ggggagaggc ggtttgcgta ttgggcgct | 3029 |

<210> SEQ ID NO 31
<211> LENGTH: 3749
<212> TYPE: DNA
<213> ORGANISM: Artificial Sequence
<220> FEATURE:
<223> OTHER INFORMATION: Chemically synthesized

<400> SEQUENCE: 31

| | |
|---|---|
| atgagagtca aaacctttgt gatcttggtc tgcgctctgc aggtgagtta attattttac | 60 |
| tattatttca gaaggtggcc agacgatatc acgggccacc tgataataag tggtcgccaa | 120 |
| aacgcacaga tatcgtaaat tgtgccattt gatttgtcac gccctggggg gctacgaat | 180 |
| aaactacatt tatttattta aaaaatgaac cttagattat gtaacttgtg atttatttgc | 240 |
| gtcaaaagta ggcaagatga atctatgtaa atactgggca gacttgcaat atcctatttc | 300 |
| accggtaaaa tcagcattgc aatatgcaat gctaaattca acaatatgta aaacaattcg | 360 |
| taaagcatca ttagaaaata gacgaaagaa attgcataaa attataaccg cattattaat | 420 |
| ttattatgat atctattaac aattgctatt gccttttttt cgcaaattat aatcattttc | 480 |
| ataacctcga ggtagcattc tgtacatttt aatacattgg tatgtgatta aacacgagc | 540 |
| tgcccactga gtttctcgcc agatcttctc agtgggtcgc gttaccgatc acgtgataga | 600 |
| ttctatgaag cactgctctt gttagggcta gtgttagtaa attctttcag gttgagtctg | 660 |
| agagctcacc tacccatcgg agcgtagctg aataggcta ccagctggta ggtagggaaa | 720 |
| caaagctcga aacaagctca gtaataaca acataatgtg accataaaat ctcgtggtgt | 780 |
| atgagataca attatgtact ttcccacaaa tgtttacata ttagaatgt tgttcaactt | 840 |
| gcctaacgcc ccagctagaa cattcaatta ttactattac cactactaag gcagtatgtc | 900 |
| ctaactcgtt ccagatcagc gctaacttcg attgaatgtg cgaaatttat agctcaatat | 960 |
| tttagcactt atcgtattga tttaagaaaa aattgttaac atttttgtttc agtatgtcgc | 1020 |
| ttatacaaat gcaaacatca atgattccgg attgggggt cagggtgctg ctgctgctgc | 1080 |
| agccgctgct gcgggaggtg ggggtcaagg gggaggatat ggaggattag gtcgcaggc | 1140 |
| tggaagagga ggaggaagcg gacgaggagg attaggagga caaggagctg ctgctgctgc | 1200 |
| agccgctgct gctggaggag gcggacaagg tgggttagga ggtcaaggtg ctgcggctgc | 1260 |
| tgctgctgct gctgctggag gaggaggaca aggcggagga tatgggggtt taggaagtca | 1320 |
| ggcaggaaga ggaggagggg gaagaggagg attgggggga caaggagctg ctgctgctgc | 1380 |
| agccgctgct gctggaggag gaggtcaggg aggaggatat ggtggattag gaagccaagc | 1440 |
| tggaaggga ggattaggag gacagggtgc tgcagctgct gctgcggccg cggctggagg | 1500 |
| gggggggtcag ggaggtggat atggaggatt aggatcacaa gctggaagag gaggattagg | 1560 |

```
aggacaggga gctgctgcag ctgctgccgc tgctgctgga ggaggaggac aaggtggagg   1620
atacggtggg ttggggagtc aagcaggtag aggaggaggt tatggaggat tgggaagtca   1680
agctggaaga gggggaggta gtggtcgagg aggaggagga caaggtgcgg ctgctgcggc   1740
cgcggctgct gcaggtggag gaggtcaggg aggattagga ggtcagggtg aggacaggga   1800
aggtcaaggt gctgctgcag ccgctgcagc cgctgctgga gggggaggtc agggaggtgg   1860
ttatggaggt ttaggaagtc aagcaggaag aggggattag gtggtcaag gagctgctgc    1920 tgctgctgct gccgcagcgg gtggaggagg gcaaggtgga agtcaggcag gtagaggagg   1980
gttaggtccc gggatggtga gcaagggcga ggagctgttc accggggtgg tgcccatcct   2040
ggtcgagctg gacggcgacg taaacggcca caagttcagc gtgtccggcg agggcgaggg   2100
cgatgccacc tacggcaagc tgaccctgaa gttcatctcc accaccggca agctgcccgt   2160
gccctggccc accctcgtga ccaccctcac ctacggcgtg caggtcttca gccgctaccc   2220
cgaccacatg aagcagcacg acttcttcaa gtccgccatg cccgaaggct acgtccagga   2280
gcgcaccatc tctttcaagg acgacggcaa ctacaagacc cgcgccgagg tgaagttcga   2340
gggcgacacc ctggtgaacc gcatcgagct gaagggcatc gacttcaagg aggacggcaa   2400
catcctgggg cacaagctgg agtacaacta caaccccac aacgtctata tcatggccga    2460
caagcagaag aacggcatca aggtgaactt caagaccggt cacaacatcg aggacggcag   2520
cgtgcagctc gccgaccact accagcagaa cacccccatc ggcgacggcc ccgtgctgct   2580
gcccgacaac cactacctga gcacccagtc caagctgctc aaagacccca acgagaagcg   2640
cgatcacatg gtcctgctgg agttcgtgac cgccgccggg atcactctcg gcatggacga   2700
gctgtacaag ggtgtgtcat ctgcttcatc tcgcagttac gactattctc gtcgtaacgt   2760
ccgcaaaaac tgtggaattc ctagaagaca actagttgtt aaattcagag cactgccttg   2820
tgtgaattgc taatttttaa tataaaataa cccttgtttc ttacttcgtc ctggatacat   2880
ctatgttttt tttttcgtta ataatgaga gcatttaagt tattgttttt aattactttt    2940
ttttagaaaa cagatttcgg atttttttgta tgcattttat ttgaatgtac taatataatc   3000
aattaatcaa tgaattcatt tatttaaggg ataacaataa tccatgaatt cacatgcaca   3060
tttaaaacaa aactaaatta caataggttc atataaaaac aacaagtatg ccttctcaac   3120
taagaatact atattgttta aaccgtaaaa aaagtcatat ttctgtatat caaaacacat   3180
ctaatattaa aaaacagtc agcaagcact tacaagtgtg ggctcggaca gcaattacct    3240
ggtctcagga gacacttgaa gaacgagaag cacgtctctc tgtcgattgc gaggctcatg   3300
cactatcgct tgagtctgag acctttactg atagggaaat ccgtttgagc tctcagaggg   3360
ttcggacagc aaaagcttgc ccggtctcag gagacattag aagaacggga agcataactc   3420
aataccgatc gcgtttccat tgagcctatg cttcgtgata ataataaata aagcccaagg   3480
tcagacgcta aaagaaagga gataggatcc aagcttggcg taatcatggt catagctgtt   3540
tcctgtgtga aattgttatc cgctcacaat tccacacaac atacgagccg aagcataaa    3600 gtgtaaagcc tggggtgcct aatgagtgag ctaactcaca ttaattgcgt tgcgctcact   3660
gcccgctttc cagtcgggaa acctgtcgtg ccagctgcat taatgaatcg ccaacgcgc    3720 ggggagaggc ggtttgcgta ttgggcgct                                    3749
```

<210> SEQ ID NO 32
<211> LENGTH: 3971
<212> TYPE: DNA

<213> ORGANISM: Artificial Sequence
<220> FEATURE:
<223> OTHER INFORMATION: Chemically synthesized

<400> SEQUENCE: 32

```
atgagagtca aaacctttgt gatcttggtc tgcgctctgc aggtgagtta attattttac      60
tattatttca gaaggtggcc agacgatatc acgggccacc tgataataag tggtcgccaa     120
aacgcacaga tatcgtaaat tgtgccattt gatttgtcac gccctgggg  gctacggaat     180
aaactacatt tatttattta aaaaatgaac cttagattat gtaacttgtg atttatttgc     240
gtcaaaagta ggcaagatga atctatgtaa atactgggca gacttgcaat atcctatttc     300
accggtaaaa tcagcattgc aatatgcaat gctaaattca acaatatgta aaacaattcg     360
taaagcatca ttagaaaata gacgaaagaa attgcataaa attataaccg cattattaat     420
ttattatgat atctattaac aattgctatt gccttttttt cgcaaattat aatcattttc     480
ataacctcga ggtagcattc tgtacatttt aatacattgg tatgtgatta taacacgagc     540
tgcccactga gtttctcgcc agatcttctc agtgggtcgc gttaccgatc acgtgataga     600
ttctatgaag cactgctctt gttagggcta gtgttagtaa attctttcag gttgagtctg     660
agagctcacc tacccatcgg agcgtagctg aataggctac ccagctggta ggtagggaaa     720
caaagctcga aacaagctca agtaataaca acataatgtg accataaaat ctcgtggtgt     780
atgagataca attatgtact ttcccacaaa tgtttacata attagaatgt tgttcaactt     840
gcctaacgcc ccagctagaa cattcaatta ttactattac cactactaag gcagtatgtc     900
ctaactcgtt ccagatcagc gctaacttcg attgaatgtg cgaaatttat agctcaatat     960
tttagcactt atcgtattga tttaagaaaa aattgttaac attttgtttc agtatgtcgc    1020
ttatacaaat gcaaacatca atgattccgg attgggggt  cagggtgctg ctgctgctgc    1080
agccgctgct gcgggaggtg ggggtcaagg gggaggatat ggaggattag gtcgcaggc     1140
tggaagagga ggaggaagcg gacgaggagg attaggagga caaggagctg ctgctgctgc    1200
agccgctgct gctggaggag gcggacaagg tgggttagga ggtcaaggtg ctgcggctgc    1260
tgctgctgct gctgctggag gaggaggaca aggcggagga tatgggggtt taggaagtca    1320
ggcaggaaga ggaggagggg gaagaggagg attgggggga caaggagctg ctgctgctgc    1380
agccgctgct gctggaggag gaggtcaggg aggaggatat ggtggattag gaagccaagc    1440
tggaagggga ggattaggag gacagggtgc tgcagctgct gctgcggccg cggctggagg    1500
gggggggtcag ggaggtggat atggaggatt aggatcacaa gctggaagag gaggattagg    1560
aggacaggga gctgctgcag ctgctgccgc tgctgctgga ggaggaggac aaggtggagg    1620
atacggtggg ttgggagtc  aagcaggtag aggaggaggt tatggaggat tgggaagtca    1680
agctggaaga ggggaggta  gtggtcgagg aggaggagga caaggtgcgg ctgctgcggc    1740
cgcggctgct gcaggtggag gaggtcaggg aggattagga ggtcagggtg gaggacaggg    1800
aggtcaaggt gctgctgcag ccgctgcagc cgctgctgga ggggaggtc  agggaggtgg    1860
ttatggaggt ttaggaagtc aagcaggaag aggggattaa ggtggtcaag gagctgctgc    1920
tgctgctgct gccgcagcgg gtggaggagg gcaaggtgga agtcaggcag gtagaggagg    1980
gttaggttcc gggttggggg gtcagggtgc tgctgctgct gcagccgctg ctgcgggagg    2040
tgggggtcaa ggggaggat  atggaggatt agggtcgcag gctggaagag gaggaggaag    2100
cggacgagga ggattaggag gacaaggagc tgctgctgct gcagccgctg ctgctggagg    2160
aggcggacaa ggtgggttag gaggtcaagg tgctgcggct gctgctgctg ctgctgctgg    2220
```

```
aggaggagga caaggcggag gatatggggg tttaggaagt caggcaggaa gaggaggagg    2280
gggaagagga ggattggggg gacaaggagc tgctgctgct gcagccgctg ctgctggagg    2340
aggaggtcag ggaggaggat atggtggatt aggaagccaa gctggaaggg gaggattagg    2400
aggacagggt gctgcagctg ctgctgcggc cgcggctgga gggggggtc agggaggtgg     2460 atatggagga ttaggatcac aagctggaag aggaggatta ggaggacagg gagctgctgc    2520
agctgctgcc gctgctgctg gaggaggagg acaaggtgga ggatacgtg ggttggggag     2580 tcaagcaggt agaggaggag gttatggagg attgggaagt caagctggaa gaggggggagg   2640 tagtggtcga ggaggaggag gacaaggtgc ggctgctgcg gccgcggctg ctgcaggtgg    2700
aggaggtcag ggaggattag gaggtcaggg tggaggacag ggaggtcaag gtgctgctgc    2760
agccgctgca gccgctgctg gaggggggagg tcagggaggt ggttatggag gtttaggaag   2820
tcaagcagga agaggggggat taggtggtca aggagctgct gctgctgctg ctgccgcagc   2880
gggtggagga gggcaaggtg gaagtcaggc aggtagagga gggttaggtc ccggggtgtc    2940
atctgcttca tctcgcagtt acgactattc tcgtcgtaac gtccgcaaaa actgtggaat    3000
tcctagaaga caactagttg ttaaattcag agcactgcct tgtgtgaatt gctaattttt    3060
aatataaaat aacccttgtt tcttacttcg tcctggatac atctatgttt tttttttcgt    3120
taataaatga gagcatttaa gttattgttt ttaattactt tttttagaa acagatttc     3180 ggattttttg tatgcatttt atttgaatgt actaatataa tcaattaatc aatgaattca    3240
tttatttaag ggataacaat aatccatgaa ttcacatgca catttaaaac aaaactaaat    3300
tacaataggt tcatatataaa acaacaagta tgccttctca actaagaata ctatattgtt    3360
taaaccgtaa aaaagtcat atttctgtat atcaaaacac atctaatatt aaaaaaacag    3420
tcagcaagca cttacaagtg tgggctcgga cagcaattac ctggtctcag gagacacttg    3480
aagaacgaga agcacgtctc tctgtcgatt gcgaggctca tgcactatcg cttgagtctg    3540
agacctttac tgatagggaa atccgtttga gctctcagag ggttcggaca gcaaaagctt    3600
gcccggtctc aggagacatt agaagaacgg gaagcataac tcaataccga tcgcgtttcc    3660
attgagccta tgcttcgtga taataataaa taaagcccaa ggtcagacgc taaaagaaag   3720
gagataggat ccaagcttgg cgtaatcatg gtcatagctg tttcctgtgt gaaattgtta    3780
tccgctcaca attccacaca acatacgagc cggaagcata agtgtaaag cctgggtgc      3840 ctaatgagtg agctaactca cattaattgc gttgcgctca ctgcccgctt tccagtcggg    3900
aaacctgtcg tgccagctgc attaatgaat cggccaacgc gcggggagag gcggtttgcg    3960
tattgggcgc t                                                         3971
```

<210> SEQ ID NO 33
<211> LENGTH: 4691
<212> TYPE: DNA
<213> ORGANISM: Artificial Sequence
<220> FEATURE:
<223> OTHER INFORMATION: Chemically synthesized

<400> SEQUENCE: 33

```
atgagagtca aaacctttgt gatcttggtc tgcgctctgc aggtgagtta attattttac      60
tattatttca gaaggtggcc agacgatatc acgggccacc tgataataag tggtcgccaa    120
aacgcacaga tatcgtaaat tgtgccattt gatttgtcac gccctggggg gctacggaat    180
aaactacatt tatttattta aaaaatgaac cttagattat gtaacttgtg atttatttgc    240
```

```
gtcaaaagta ggcaagatga atctatgtaa atactgggca gacttgcaat atcctatttc    300
accggtaaaa tcagcattgc aatatgcaat gctaaattca acaatatgta aaacaattcg    360
taaagcatca ttagaaaata gacgaaagaa attgcataaa attataaccg cattattaat    420
ttattatgat atctattaac aattgctatt gccttttttt cgcaaattat aatcattttc    480
ataacctcga ggtagcattc tgtacatttt aatacattgg tatgtgatta taacacgagc    540
tgcccactga gtttctcgcc agatcttctc agtgggtcgc gttaccgatc acgtgataga    600
ttctatgaag cactgctctt gttagggcta gtgttagtaa attctttcag gttgagtctg    660
agagctcacc tacccatcgg agcgtagctg aataggcta ccagctggta ggtagggaaa    720
caaagctcga aacaagctca agtaataaca acataatgtg accataaaat ctcgtggtgt    780
atgagataca attatgtact ttcccacaaa tgtttacata attagaatgt tgttcaactt    840
gcctaacgcc ccagctagaa cattcaatta ttactattac cactactaag gcagtatgtc    900
ctaactcgtt ccagatcagc gctaacttcg attgaatgtg cgaaatttat agctcaatat    960
tttagcactt atcgtattga tttaagaaaa aattgttaac attttgtttc agtatgtcgc   1020
ttatacaaat gcaaacatca atgattccgg attgggggt caggtgctg ctgctgctgc    1080 agccgctgct gcgggaggtg ggggtcaagg gggaggatat ggaggattag ggtcgcaggc   1140
tggaagagga ggaggaagcg gacgaggagg attaggagga caaggagctg ctgctgctgc   1200
agccgctgct gctggaggag gcggacaagg tgggttagga ggtcaaggtg ctgcggctgc   1260
tgctgctgct gctgctggag gaggaggaca aggcggagga tatgggggtt taggaagtca   1320
ggcaggaaga ggaggagggg gaagaggagg attgggggga caaggagctg ctgctgctgc   1380
agccgctgct gctggaggag gaggtcaggg aggaggatat ggtggattag gaagccaagc   1440
tggaagggga ggattaggag gacagggtgc tgcagctgct gctgcggccg cggctggagg   1500 gggggtcag ggaggtggat atggaggatt aggatcacaa gctggaagag gaggattagg   1560
aggacaggga gctgctgcag ctgctgccgc tgctgctgga ggaggaggac aaggtggagg   1620
atacggtggg ttggggagtc aagcaggtag aggaggaggt tatggaggat tgggaagtca   1680
agctggaaga gggggaggta gtggtcgagg aggaggagga caaggtgcgg ctgctgcggc   1740
cgcggctgct gcaggtggag gaggtcaggg aggattagga ggtcagggtg aggacaggg   1800 aggtcaaggt gctgctgcag ccgctgcagc cgctgctgga ggggaggtc agggaggtgg   1860 ttatggaggt ttaggaagtc aagcaggaag aggggatta ggtggtcaag gagctgctgc    1920
tgctgctgct gccgcagcgg gtggaggagg gcaaggtgga agtcaggcag gtagaggagg   1980
gttaggttcc gggttggggg gtcagggtgc tgctgctgct gcagccgctg ctgcgggagg   2040
tgggggtcaa gggggaggat atggaggatt agggtcgcag gctggaagag gaggaggaag   2100
cggacgagga ggattaggag gacaaggagc tgctgctgct gcagccgctg ctgctggagg   2160
aggcggacaa ggtgggttag gaggtcaagg tgctgcggct gctgctgctg ctgctgctgg   2220
aggaggagga caaggcggag gatatggggg tttaggaagt caggcaggaa gaggaggagg   2280
gggaagagga ggattggggg gacaaggagc tgctgctgct gcagccgctg ctgctggagg   2340
aggaggtcag ggaggaggat atggtggatt aggaagccaa gctggaaggg gaggattagg   2400
aggacagggt gctgcagctg ctgctgcggc cgcggctgga ggggggggtc agggaggtgg   2460
atatggagga ttaggatcac aagctggaag aggaggatta ggaggacagg gagctgctgc   2520
agctgctgcc gctgctgctg gaggaggagg acaaggtgga ggatacggtg ggttggggag   2580
tcaagcaggt agaggaggag gttatggagg attgggaagt caagctggaa gaggggagg   2640
```

```
tagtggtcga ggaggaggag gacaaggtgc ggctgctgcg gccgcggctg ctgcaggtgg    2700
aggaggtcag ggaggattag gaggtcaggg tggaggacag ggaggtcaag gtgctgctgc    2760
agccgctgca gccgctgctg gaggggagg tcagggaggt ggttatggag gtttaggaag     2820
tcaagcagga gagggggat taggtggtca aggagctgct gctgctgctg ctgccgcagc     2880
gggtggagga gggcaaggtg gaagtcaggc aggtagagga gggttaggtc ccgggatggt    2940
gagcaagggc gaggagctgt tcaccggggt ggtgcccatc ctggtcgagc tggacgcgcga   3000 cgtaaacggc cacaagttca gcgtgtccgg cgagggcgag ggcgatgcca cctacggcaa    3060
gctgaccctg aagttcatct ccaccaccgg caagctgccc gtgccctggc ccaccctcgt    3120
gaccaccctc acctacggcg tgcaggtctt cagccgctac cccgaccaca tgaagcagca    3180
cgacttcttc aagtccgcca tgcccgaagg ctacgtccag gagcgcacca tctctttcaa    3240
ggacgacggc aactacaaga cccgcgccga ggtgaagttc gagggcgaca ccctggtgaa    3300
ccgcatcgag ctgaagggca tcgacttcaa ggaggacggc aacatcctgg ggcacaagct    3360
ggagtacaac tacaacccccc acaacgtcta tatcatggcc gacaagcaga gaacggcat    3420 caaggtgaac ttcaagaccc gtcacaacat cgaggacggc agcgtgcagc tcgccgacca    3480
ctaccagcag aacacccccca tcggcgacgg ccccgtgctg ctgcccgaca ccactacct    3540 gagcacccag tccaagctgc tcaaagaccc caacgagaag cgcgatcaca tggtcctgct    3600
ggagttcgtg accgccgccg ggatcactct cggcatggac gagctgtaca agggtgtgtc    3660
atctgcttca tctcgcagtt acgactattc tcgtcgtaac gtccgcaaaa actgtggaat    3720
tcctagaaga caactagttg ttaaattcag agcactgcct tgtgtgaatt gctaattttt    3780
aatataaaat aaccccttgtt tcttacttcg tcctggatac atctatgtttt tttttttcgt   3840 taataaatga gagcatttaa gttattgttt ttaattactt ttttttagaa aacagatttc    3900 ggatttttg tatgcatttt atttgaatgt actaatataa tcaattaatc aatgaattca    3960
tttatttaag ggataacaat aatccatgaa ttcacatgca catttaaaac aaaactaaat    4020
tacaataggt tcatataaaa acaacaagta tgccttctca actaagaata ctatattgtt    4080
taaaccgtaa aaaaagtcat atttctgtat atcaaaacac atctaatatt aaaaaaacag    4140
tcagcaagca cttacaagtg tgggctcgga cagcaattac ctggtctcag gagacacttg    4200
aagaacgaga agcacgtctc tctgtcgatt gcgaggctca tgcactatcg cttgagtctg    4260
agacctttac tgatagggaa atccgtttga gctctcagag ggttcggaca gcaaaagctt    4320
gcccggtctc aggagacatt agaagaacgg gaagcataac tcaataccga tcgcgtttcc    4380
attgagccta tgcttcgtga taataataaa taaagcccaa ggtcagacgc taaaagaaag    4440
gagataggat ccaagcttgg cgtaatcatg gtcatagctg tttcctgtgt gaaattgtta    4500
tccgctcaca attccacaca acatacgagc cggaagcata agtgtaaag cctggggtgc     4560 ctaatgagtg agctaactca cattaattgc gttgcgctca ctgcccgctt tccagtcggg    4620
aaacctgtcg tgccagctgc attaatgaat cggccaacgc gcggggagag gcggtttgcg    4680
tattgggcgc t                                                        4691
```

<210> SEQ ID NO 34
<211> LENGTH: 4913
<212> TYPE: DNA
<213> ORGANISM: Artificial Sequence
<220> FEATURE:
<223> OTHER INFORMATION: Chemically synthesized

```
<400> SEQUENCE: 34
atgagagtca aaacctttgt gatcttggtc tgcgctctgc aggtgagtta attatttac      60 tattatttca gaaggtggcc agacgatatc acgggccacc tgataataag tggtcgccaa     120
aacgcacaga tatcgtaaat tgtgccattt gatttgtcac gccctggggg gctacggaat     180
aaactacatt tatttattta aaaatgaac cttagattat gtaacttgtg atttatttgc      240
gtcaaaagta ggcaagatga atctatgtaa atactgggca gacttgcaat atcctatttc     300
accggtaaaa tcagcattgc aatatgcaat gctaaattca acaatatgta aaacaattcg     360
taaagcatca ttagaaaata gacgaaagaa attgcataaa attataaccg cattattaat     420
ttattatgat atctattaac aattgctatt gccttttttt cgcaaattat aatcattttc     480
ataacctcga ggtagcattc tgtacatttt aatacattgg tatgtgatta taacacgagc     540
tgcccactga gtttctcgcc agatcttctc agtgggtcgc gttaccgatc acgtgataga     600
ttctatgaag cactgctctt gttagggcta gtgttagtaa attctttcag gttgagtctg     660
agagctcacc tacccatcgg agcgtagctg aataggcta ccagctggta ggtagggaaa      720
caaagctcga aacaagctca agtaataaca acataatgtg accataaaat ctcgtggtgt     780
atgagataca attatgtact ttcccacaaa tgtttacata attagaatgt tgttcaactt     840
gcctaacgcc ccagctagaa cattcaatta ttactattac cactactaag gcagtatgtc     900
ctaactcgtt ccagatcagc gctaacttcg attgaatgtg cgaaatttat agctcaatat     960
tttagcactt atcgtattga tttaagaaaa aattgttaac attttgtttc agtatgtcgc    1020
ttatacaaat gcaaacatca atgattccgg attggggggt cagggtgctg ctgctgctgc    1080
agccgctgct gcgggaggtg ggggtcaagg gggaggatat ggaggattag gtcgcaggc     1140 tggaagagga ggaggaagcg gacgaggagg attaggagga caaggagctg ctgctgctgc    1200
agccgctgct gctggaggag gcggacaagg tgggttagga ggtcaaggtg ctgcggctgc    1260
tgctgctgct gctgctggag gaggaggaca aggcggagga tatgggggtt taggaagtca    1320
ggcaggaaga ggaggagggg gaagaggagg attgggggga caaggagctg ctgctgctgc    1380
agccgctgct gctggaggag gaggtcaggg aggaggatat ggtggattag gaagccaagc    1440
tggaagggga ggattaggag gacagggtgc tgcagctgct gctgcggccg cggctggagg    1500 gggggggtcag ggaggtggat atggaggatt aggatcacaa gctggaagag gaggattagg    1560
aggacaggga gctgctgcag ctgctgccgc tgctgctgga ggaggaggac aaggtggagg    1620
atacggtggg ttggggagtc aagcaggtag aggaggaggt tatggaggat tgggaagtca    1680
agctggaaga gggggaggta gtggtcgagg aggaggagga caaggtgcgg ctgctgcggc    1740
cgcggctgct gcaggtggag gaggtcaggg aggattagga ggtcagggtg gaggacaggg    1800
aggtcaaggt gctgctgcag ccgctgcagc cgctgctgga ggggaggtc agggaggtgg     1860 ttatggaggt ttaggaagtc aagcaggaag aggggggatta ggtggtcaag gagctgctgc    1920
tgctgctgct gccgcagcgg gtggaggagg gcaaggtgga agtcaggcag gtagaggagg    1980
gttaggttcc gggttggggg gtcagggtgc tgctgctgct gcagccgctg ctgcgggagg    2040
tgggggtcaa gggggaggat atggaggatt agggtcgcag gctggaagag gaggaggaag    2100
cggacgagga ggattaggag gacaaggagc tgctgctgct gcagccgctg ctgctggagg    2160
aggcggacaa ggtgggttag gaggtcaagg tgctgcggct gctgctgctg ctgctgctgg    2220
aggaggagga caaggcggag gatatggggg tttaggaagt caggcaggaa gaggaggagg    2280
gggaagagga ggattggggg gacaaggagc tgctgctgct gcagccgctg ctgctggagg    2340
```

```
aggaggtcag ggaggaggat atggtggatt aggaagccaa gctggaaggg gaggattagg    2400
aggacagggt gctgcagctg ctgctgcggc cgcggctgga ggggggggtc agggaggtgg    2460
atatggagga ttaggatcac aagctggaag aggaggatta ggaggacagg gagctgctgc    2520
agctgctgcc gctgctgctg gaggaggagg acaaggtgga ggatacggtg ggttggggag    2580
tcaagcaggt agaggaggag gttatggagg attgggaagt caagctggaa gaggggagg     2640 tagtggtcga ggaggaggag gacaaggtgc ggctgctgcg gccgcggctg ctgcaggtgg    2700
aggaggtcag ggaggattag gaggtcaggg tggaggacag ggaggtcaag gtgctgctgc    2760
agccgctgca gccgctgctg gagggggagg tcagggaggt ggttatggag gtttaggaag    2820
tcaagcagga gagggggat  taggtggtca aggagctgct gctgctgctg ctgccgcagc    2880
gggtggagga gggcaaggtg gaagtcaggc aggtagagga gggttaggtt ccggttgg     2940 gggtcagggt gctgctgctg ctgcagccgc tgctgcggga ggtgggggtc aagggggagg    3000
atatggagga ttagggtcgc aggctggaag aggaggagga gcggacgag  gaggattagg    3060 aggacaagga gctgctgctg ctgcagccgc tgctgctgga ggaggcggac aaggtgggtt    3120
aggaggtcaa ggtgctgcgg ctgctgctgc tgctgctgct ggaggaggag gacaaggcgg    3180
aggatatggg ggtttaggaa gtcaggcagg aagaggagga gggggaagag gaggattggg    3240
gggacaagga gctgctgctg ctgcagccgc tgctgctgga ggaggaggtc agggaggagg    3300
atatggtgga ttaggaagcc aagctggaag gggaggatta ggaggacagg gtgctgcagc    3360
tgctgctgcg gccgcggctg gagggggggg tcagggaggt ggatatggag gattaggatc    3420
acaagctgga agaggaggat taggaggaca gggagctgct gcagctgctg ccgctgctgc    3480
tggaggagga ggacaaggtg gaggatacgg tgggttgggg agtcaagcag gtagaggagg    3540
aggttatgga ggattgggaa gtcaagctgg aagagggga  ggtagtggtc gaggaggagg    3600
aggacaaggt gcggctgctg cggccgcggc tgctgcaggt ggaggaggtc agggaggatt    3660
aggaggtcag ggtggaggac agggaggtca aggtgctgct gcagccgctg cagccgctgc    3720 tggagggga  ggtcagggag gtggttatgg aggtttagga agtcaagcag gaagaggggg    3780
attaggtggt caaggagctg ctgctgctgc tgctgccgca gcgggtggag gagggcaagg    3840
tggaagtcag gcaggtagag gagggttagg tcccggggtg tcatctgctt catctcgcag    3900
ttacgactat tctcgtcgta acgtccgcaa aaactgtgga attcctagaa gacaactagt    3960
tgttaaattc agagcactgc cttgtgtgaa ttgctaattt ttaatataaa ataacccttg    4020
tttcttactt cgtcctggat acatctatgt tttttttttc gttaataaat gagagcattt    4080
aagttattgt ttttaattac ttttttttag aaaacagatt tcggattttt tgtatgcatt    4140
ttatttgaat gtactaatat aatcaattaa tcaatgaatt catttatta  agggataaca    4200 ataatccatg aattcacatg cacatttaaa acaaaactaa attacaatag gttcatataa    4260
aaacaacaag tatgccttct caactaagaa tactatattg tttaaaccgt aaaaaaagtc    4320
atatttctgt atatcaaaac acatctaata ttaaaaaaac agtcagcaag cacttacaag    4380
tgtgggctcg acagcaatt  acctggtctc aggagacact tgaagaacga gaagcacgtc    4440
tctctgtcga ttgcgaggct catgcactat cgcttgagtc tgagaccttt actgataggg    4500
aaatccgttt gagctctcag agggttcgga cagcaaaagc ttgcccggtc tcaggagaca    4560
ttagaagaac gggaagcata actcaatacc gatcgcgttt ccattgagcc tatgcttcgt    4620
gataataata aataaagccc aaggtcagac gctaaaagaa aggagatagg atccaagctt    4680
```

```
ggcgtaatca tggtcatagc tgtttcctgt gtgaaattgt tatccgctca caattccaca    4740
caacatacga gccggaagca taaagtgtaa agcctgggt gcctaatgag tgagctaact    4800
cacattaatt gcgttgcgct cactgcccgc tttccagtcg ggaaacctgt cgtgccagct    4860
gcattaatga atcggccaac gcgcggggag aggcggtttg cgtattgggc gct           4913

<210> SEQ ID NO 35
<211> LENGTH: 5633
<212> TYPE: DNA
<213> ORGANISM: Artificial Sequence
<220> FEATURE:
<223> OTHER INFORMATION: Chemically synthesized

<400> SEQUENCE: 35
atgagagtca aaacctttgt gatcttggtc tgcgctctgc aggtgagtta attattttac     60
tattatttca gaaggtggcc agacgatatc acgggccacc tgataataag tggtcgccaa    120
aacgcacaga tatcgtaaat tgtgccattt gatttgtcac gccctggggg gctacggaat    180
aaactacatt tatttattta aaaaatgaac cttagattat gtaacttgtg atttatttgc    240
gtcaaaagta ggcaagatga atctatgtaa atactgggca gacttgcaat atcctatttc    300
accggtaaaa tcagcattgc aatatgcaat gctaaattca acaatatgta aaacaattcg    360
taaagcatca ttagaaaata gacgaaagaa attgcataaa attataaccg cattattaat    420
ttattatgat atctattaac aattgctatt gccttttttt cgcaaattat aatcattttc    480
ataacctcga ggtagcattc tgtacatttt aatacattgg tatgtgatta taacacgagc    540
tgcccactga gtttctcgcc agatcttctc agtgggtcgc gttaccgatc acgtgataga    600
ttctatgaag cactgctctt gttagggcta gtgttagtaa attctttcag gttgagtctg    660
agagctcacc tacccatcgg agcgtagctg aataggcta ccagctggta ggtagggaaa     720
caaagctcga aacaagctca agtaataaca acataatgtg accataaaat ctcgtggtgt    780
atgagataca attatgtact ttcccacaaa tgtttacata attagaatgt tgttcaactt    840
gcctaacgcc ccagctagaa cattcaatta ttactattac cactactaag gcagtatgtc    900
ctaactcgtt ccagatcagc gctaacttcg attgaatgtg cgaaatttat agctcaatat    960
tttagcactt atcgtattga tttaagaaaa aattgttaac attttgtttc agtatgtcgc   1020
ttatacaaat gcaaacatca atgattccgg attggggggt cagggtgctg ctgctgctgc   1080
agccgctgct gcgggaggtg ggggtcaagg ggaggatat ggaggattag ggtcgcaggc   1140
tggaagagga ggaggaagcg gacgaggagg attaggagga caaggagctg ctgctgctgc   1200
agccgctgct gctggaggag gcggacaagg tgggttagga ggtcaaggtg ctgcggctgc   1260
tgctgctgct gctgctggag gaggaggaca aggcggagga tatgggggtt taggaagtca   1320
ggcaggaaga ggaggagggg gaagaggagg attgggggga caaggagctg ctgctgctgc   1380
agccgctgct gctggaggag gaggtcaggg aggaggatat ggtggattag gaagccaagc   1440
tggaagggga ggattaggag gacagggtgc tgcagctgct gctgcggccg cggctggagg   1500 gggggggtcag gaggtggat atggaggatt aggatcacaa gctggaagag gaggattagg   1560
aggacaggga gctgctgcag ctgctgccgc tgctgctgga ggaggaggac aaggtggagg   1620
atacggtggg ttggggagtc aagcaggtag aggaggaggt tatggaggat tgggaagtca   1680
agctggaaga gggggaggta gtggtcgagg aggaggagga caaggtgcgg ctgctgcggc   1740
cgcggctgct gcaggtggag gaggtcaggg aggattagga ggtcagggtg aggacaggg   1800 aggtcaaggt gctgctgcag ccgctgcagc cgctgctgga ggggaggtc agggaggtgg   1860
```

```
ttatggaggt ttaggaagtc aagcaggaag aggggggatta ggtggtcaag gagctgctgc    1920
tgctgctgct gccgcagcgg gtggaggagg gcaaggtgga agtcaggcag gtagaggagg    1980
gttaggttcc gggttggggg gtcagggtgc tgctgctgct gcagccgctg ctgcgggagg    2040
tgggggtcaa gggggaggat atggaggatt agggtcgcag gctggaagag gaggaggaag    2100
cggacgagga ggattaggag gacaaggagc tgctgctgct gcagccgctg ctgctggagg    2160
aggcggacaa ggtgggttag gaggtcaagg tgctgcggct gctgctgctg ctgctgctgg    2220
aggaggagga caaggcggag gatatggggg tttaggaagt caggcaggaa gaggaggagg    2280
gggaagagga ggattggggg gacaaggagc tgctgctgct gcagccgctg ctgctggagg    2340
aggaggtcag ggaggaggat atggtggatt aggaagccaa gctggaaggg gaggattagg    2400
aggacagggt gctgcagctg ctgctgcggc cgcggctgga gggggggtc agggaggtgg    2460 atatggagga ttaggatcac aagctggaag aggaggatta ggaggacagg gagctgctgc    2520
agctgctgcc gctgctgctg gaggaggagg acaaggtgga ggatacggtg ggttggggag    2580
tcaagcaggt agaggaggag gttatggagg attgggaagt caagctggaa gagggggagg    2640
tagtggtcga ggaggaggag gacaaggtgc ggctgctgcg gccgcggctg ctgcaggtgg    2700
aggaggtcag ggaggattag gaggtcaggg tggaggacag ggaggtcaag gtgctgctgc    2760
agccgctgca gccgctgctg gagggggagg tcagggaggt ggttatggag gtttaggaag    2820
tcaagcagga agaggggggat taggtggtca aggagctgct gctgctgctg ctgccgcagc    2880
gggtggagga gggcaaggtg gaagtcaggc aggtagagga gggttaggtt ccgggttggg    2940
gggtcagggt gctgctgctg ctgcagccgc tgctgcggga ggtgggggtc aagggggagg    3000
atatggagga ttagggtcgc aggctggaag aggaggagga agcggacgag gaggattagg    3060
aggacaagga gctgctgctg ctgcagccgc tgctgctgga ggaggcggac aaggtgggtt    3120
aggaggtcaa ggtgctgcgg ctgctgctgc tgctgctgct ggaggaggag gacaaggcgg    3180
aggatatggg ggtttaggaa gtcaggcagg aagaggagga ggggaagag gaggattggg    3240 gggacaagga gctgctgctg ctgcagccgc tgctgctgga ggaggaggtc agggaggagg    3300
atatggtgga ttaggaagcc aagctggaag gggaggatta ggaggacagg gtgctgcagc    3360
tgctgctgcg gccgcggctg gagggggggg tcagggaggt ggatatggag gattaggatc    3420
acaagctgga agaggaggat taggaggaca gggagctgct gcagctgctg ccgctgctgc    3480
tggaggagga ggacaaggtg gaggatacgg tgggttgggg agtcaagcag gtagaggagg    3540
aggttatgga ggattgggaa gtcaagctgg aagaggggga ggtagtggtc gaggaggagg    3600
aggacaaggt gcggctgctg cggccgcggc tgctgcaggt ggaggaggtc agggaggatt    3660
aggaggtcag ggtggaggac agggaggtca aggtgctgct gcagccgctg cagccgctgc    3720
tggaggggga ggtcagggag gtggttatgg aggtttagga agtcaagcag gaagaggggg    3780
attaggtggt caaggagctg ctgctgctgc tgctgccgca gcgggtggag gagggcaagg    3840
tggaagtcag gcaggtagag gagggttagg tcccgggatg gtgagcaagg gcgaggagct    3900
gttcaccggg gtggtgccca tcctggtcga gctggacggc gacgtaaacg gccacaagtt    3960
cagcgtgtcc ggcgagggcg agggcgatgc cacctacggc aagctgaccc tgaagttcat    4020
ctccaccacc ggcaagctgc ccgtgccctg gcccaccctc gtgaccaccc tcacctacgg    4080
cgtgcaggtc ttcagccgct accccgacca catgaagcag cacgacttct tcaagtccgc    4140
catgcccgaa ggctacgtcc aggagcgcac catctctttc aaggacgacg gcaactacaa    4200
```

```
gacccgcgcc gaggtgaagt tcgagggcga caccctggtg aaccgcatcg agctgaaggg    4260
catcgacttc aaggaggacg gcaacatcct ggggcacaag ctggagtaca actacaaccc    4320
ccacaacgtc tatatcatgg ccgacaagca gaagaacggc atcaaggtga acttcaagac    4380
cggtcacaac atcgaggacg gcagcgtgca gctcgccgac cactaccagc agaacacccc    4440
catcggcgac ggccccgtgc tgctgcccga caaccactac ctgagcaccc agtccaagct    4500
gctcaaagac cccaacgaga gcgcgatca catggtcctg ctggagttcg tgaccgccgc    4560
cgggatcact ctcggcatgg acgagctgta caagggtgtg tcatctgctt catctcgcag    4620
ttacgactat tctcgtcgta acgtccgcaa aaactgtgga attcctagaa gacaactagt    4680
tgttaaattc agagcactgc cttgtgtgaa ttgctaattt ttaatataaa ataaccctctg   4740 tttcttactt cgtcctggat acatctatgt tttttttttc gttaataaat gagagcattt    4800
aagttattgt ttttaattac tttttttttag aaaacagatt tcggattttt tgtatgcatt   4860
ttatttgaat gtactaatat aatcaattaa tcaatgaatt catttattta agggataaca    4920
ataatccatg aattcacatg cacatttaaa acaaaactaa attacaatag gttcatataa    4980
aaacaacaag tatgccttct caactaagaa tactatattg tttaaaccgt aaaaaaagtc    5040
atatttctgt atatcaaaac acatctaata ttaaaaaaac agtcagcaag cacttacaag    5100
tgtgggctcg acagcaatt acctggtctc aggagacact tgaagaacga gaagcacgtc    5160
tctctgtcga ttgcgaggct catgcactat cgcttgagtc tgagaccttt actgataggg    5220
aaatccgttt gagctctcag agggttcgga cagcaaaagc ttgcccggtc tcaggagaca    5280
ttagaagaac gggaagcata actcaatacc gatcgcgttt ccattgagcc tatgcttcgt    5340
gataataata aataaagccc aaggtcagac gctaaaagaa aggagatagg atccaagctt    5400
ggcgtaatca tggtcatagc tgtttcctgt gtgaaattgt tatccgctca caattccaca    5460
caacatacga gccggaagca taaagtgtaa agcctggggt gcctaatgag tgagctaact    5520
cacattaatt gcgttgcgct cactgcccgc tttccagtcg ggaaacctgt cgtgccagct    5580
gcattaatga atcggccaac gcgcggggag aggcggtttg cgtattgggc gct           5633
```

<210> SEQ ID NO 36
<211> LENGTH: 21
<212> TYPE: PRT
<213> ORGANISM: Artificial Sequence
<220> FEATURE:
<223> OTHER INFORMATION: Chemically Synthesized

<400> SEQUENCE: 36

Leu Gly Gly Gln Gly Ala Ala Ala Ala Ala Ala Ala Ala Ala Gly Gly
1               5                   10                  15

Gly Gly Gln Gly Gly
            20

<210> SEQ ID NO 37
<211> LENGTH: 13
<212> TYPE: PRT
<213> ORGANISM: Nephila clavipes

<400> SEQUENCE: 37

Gly Tyr Gly Gly Leu Gly Ser Gln Ala Gly Arg Gly Gly
1               5                   10

<210> SEQ ID NO 38
<211> LENGTH: 8
<212> TYPE: PRT

```
<213> ORGANISM: Nephila clavipes

<400> SEQUENCE: 38

Leu Gly Gly Gln Gly Gly Gly Gln
1               5

<210> SEQ ID NO 39
<211> LENGTH: 6
<212> TYPE: PRT
<213> ORGANISM: Nephila clavipes

<400> SEQUENCE: 39

Gly Ser Gly Arg Gly Gly
1               5

<210> SEQ ID NO 40
<211> LENGTH: 21
<212> TYPE: PRT
<213> ORGANISM: Nephila clavipes

<400> SEQUENCE: 40

Leu Gly Gly Gln Gly Ala Gly Ala Ala Ala Ala Ala Ala Ala Gly Gly
1               5                   10                  15

Ala Gly Gln Gly Gly
            20

<210> SEQ ID NO 41
<211> LENGTH: 8
<212> TYPE: PRT
<213> ORGANISM: Artificial Sequence
<220> FEATURE:
<223> OTHER INFORMATION: Chemically synthesized

<400> SEQUENCE: 41

Leu Gly Gly Gln Gly Ala Gly Gln
1               5
```